(12) United States Patent
Coady et al.

(10) Patent No.: US 9,974,303 B2
(45) Date of Patent: May 22, 2018

(54) CATIONIC POLYMERS FOR ANTIMICROBIAL APPLICATIONS AND DELIVERY OF BIOACTIVE MATERIALS

(71) Applicants: International Business Machines Corporation, Armonk, NY (US); Agency For Science, Technology and Research, Singapore (SG)

(72) Inventors: Daniel J. Coady, San Jose, CA (US); Amanda C. Engler, San Jose, CA (US); Kazuki Fukushima, Yonezawa (JP); James L. Hedrick, Pleasanton, CA (US); Jeremy P. K. Tan, Singapore (SG); Yi Yan Yang, Singapore (SG)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 588 days.

(21) Appl. No.: 14/246,045

(22) Filed: Apr. 5, 2014

(65) Prior Publication Data
US 2014/0220093 A1    Aug. 7, 2014

Related U.S. Application Data

(60) Division of application No. 13/333,930, filed on Dec. 21, 2011, now Pat. No. 8,709,466, which is a continuation-in-part of application No. 13/077,005, filed on Mar. 31, 2011, now Pat. No. 8,642,086.

(51) Int. Cl.
| | |
|---|---|
| *A61K 31/357* | (2006.01) |
| *A01N 37/44* | (2006.01) |
| *A61K 48/00* | (2006.01) |
| *C12N 15/88* | (2006.01) |
| *A01N 33/12* | (2006.01) |
| *C08G 83/00* | (2006.01) |

(52) U.S. Cl.
CPC ............. *A01N 37/44* (2013.01); *A01N 33/12* (2013.01); *A61K 48/0041* (2013.01); *C08G 83/004* (2013.01); *C12N 15/88* (2013.01)

(58) Field of Classification Search
None
See application file for complete search history.

(56) References Cited

U.S. PATENT DOCUMENTS

| | | | |
|---|---|---|---|
| 4,981,696 A | 1/1991 | Loomis | |
| 5,616,317 A | 4/1997 | Nagase et al. | |
| 6,251,967 B1 | 6/2001 | Perichaud | |
| 6,361,787 B1 | 3/2002 | Shaheen | |
| 6,413,539 B1 | 7/2002 | Shalaby | |
| 6,541,033 B1 | 4/2003 | Shah | |
| 6,762,162 B1 | 7/2004 | Valpey, III | |
| 6,800,278 B1 | 10/2004 | Perrault | |
| 6,984,393 B2 | 1/2006 | Amsden | |
| 7,345,138 B2 | 3/2008 | Wang et al. | |
| 7,399,804 B2 | 7/2008 | Plummer et al. | |
| 7,666,973 B2 | 2/2010 | Stopek | |
| 7,776,359 B1 | 8/2010 | Hennink | |
| 2005/0038167 A1 | 2/2005 | Plummer et al. | |
| 2007/0048249 A1 | 3/2007 | Youngblood et al. | |
| 2007/0160566 A1 | 7/2007 | Smith et al. | |
| 2007/0185008 A1 | 8/2007 | Hennink | |
| 2008/0118546 A1 | 5/2008 | Thatcher | |
| 2008/0131512 A1 | 6/2008 | Hennink | |
| 2008/0226722 A1 | 9/2008 | Van Tomme | |
| 2008/0260795 A1 | 10/2008 | Baughman et al. | |
| 2009/0117164 A1 | 5/2009 | Toreki et al. | |
| 2009/0118459 A1 | 5/2009 | Feien et al. | |
| 2009/0281249 A1 | 11/2009 | Thatcher | |
| 2010/0003327 A1 | 1/2010 | Thatcher | |

(Continued)

FOREIGN PATENT DOCUMENTS

| | | |
|---|---|---|
| EP | 481042 B1 | 10/1991 |
| EP | 2204397 A2 | 7/2007 |

(Continued)

OTHER PUBLICATIONS

Nunez, C. M.; Chiou, B.; Andrady, A. L.; Khan S.A. Solution Rheology of Hyperbranched Polyesters and Their Blends with Linear Polymers. Macromolecules, 2000, 33, p. 1720-1726.*

Fujiwara, et al., "Novel Thermo-Responsive Formation of a Hydrogel by Stereo-Complexation between PLLA-PEG-PLLA and PDLA-PEG-PDLA Block Copolymers," Macromol. Biosci. 2001, 1, 204-208; published online: Jul. 19, 2001.

Hiemstra, et al., "Stereocomplex Mediated Gelation of PEG-(PLA)2 and PEG-(PLA)8 Block Copolymers," Macromol. Symp. 2005, 224, 119-131. Published online: May 20, 2005.

Ihre, et al., "Fast and Convenient Divergent Synthesis of Aliphatic Ester Dendrimers by Anhydride Coupling", J. Am. Soc. 2001, 123, 5908-5917. Published on Web Jun. 2, 2001.

(Continued)

*Primary Examiner* — Jessica Worsham
(74) *Attorney, Agent, or Firm* — Michael R. Roberts

(57) ABSTRACT

A cationic star polymer is disclosed of the general formula (1):

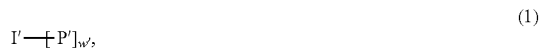

(1)

wherein w' is a positive number greater than or equal to 3, I' is a dendritic polyester core covalently linked to w' independent peripheral linear cationic polymer chains P'. Each of the chains P' comprises a cationic repeat unit comprising i) a backbone functional group selected from the group consisting of aliphatic carbonates, aliphatic esters, aliphatic carbamates, aliphaticureas, aliphatic thiocarbamates, aliphatic dithiocarbonates, and combinations thereof, and ii) a side chain comprising a quaternary amine group. The quaternary amine group comprises a divalent methylene group directly covalently linked to i) a positive charged nitrogen and ii) an aromatic ring.

21 Claims, 8 Drawing Sheets

(56) References Cited

U.S. PATENT DOCUMENTS

| | | | |
|---|---|---|---|
| 2010/0166863 A1 | 7/2010 | Shen | |
| 2010/0196494 A1 | 8/2010 | Van Beek | |
| 2010/0298577 A1* | 11/2010 | Alvarez et al. | 549/370 |
| 2010/0322890 A1 | 12/2010 | Edwards | |
| 2011/0111044 A1 | 5/2011 | Zhao et al. | |
| 2011/0124772 A1* | 5/2011 | Wang et al. | 523/177 |
| 2011/0150977 A1 | 6/2011 | Hedrick et al. | |
| 2011/0151566 A1 | 6/2011 | Hedrick et al. | |
| 2012/0283391 A1 | 11/2012 | Venkatraman et al. | |

FOREIGN PATENT DOCUMENTS

| | | |
|---|---|---|
| WO | 199524221 A1 | 9/1995 |
| WO | 1999060852 A1 | 12/1999 |
| WO | 2008018796 A2 | 2/2008 |

OTHER PUBLICATIONS

Jiang, et al., "Water-Soluble Thermoresponsive Polylactides," Macromolecules 2008, 41, 318-324. Published on Web Apr. 2, 2005.

Li, et al., "Synthesis, Characterization, and Stereocomplex-Induced Gelation of Block Copolymers Prepared by Ring-Opening Polymerization of L(D)-Lactide in the Presence of Poly(ethylene glycol)," Macromolecules 2003, 36, 8008-8014. Published on Web Sep. 27, 2003.

Liu, et al., "Biodegradable poly(ethylene glycol)—peptide hydrogels with well-defined structure and properties for cell delivery," Biomaterials 30 (2009) 1453-1461. Available online Dec. 20, 2008.

Liu, et al., "Synthetic hydrogels for controlled stem cell differentiation," Soft Matter, 2010, 6, 67-81. Published on web Nov. 24, 2009.

Lutolf, et al., "Cell-Responsive Synthetic Hydrogels," Adv. Mater. 15, No. 11, 888-891. Published online: Jun. 2, 2003.

Lutz, et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules 2006, 39, 893-896, Published on Web Dec. 21, 2005.

Malkoch, et al., "Structurally Diverse Dendritic Libraries: A Highly Efficient Functionalization Approach Using Click Chemistry," Macromolecules 2005, 38, 3663-3678, Published on Web Apr. 2, 2005.

Mespouille, et al., Soft Matter, 2009, 5, 4878-4892. Published on web Oct. 1, 2009.

Metters, et al., "Network Formation and Degradation Behavior of Hydrogels Formed by Michael-Type Addition Reactions," Biomacromolecules 2005, 6, 290-301, Published on Web Nov. 13, 2004.

Mukose, et al., "Hydrogel Formation between Enantiomeric B-A-B-Type Block Copolymers of Polylactides (PLLA or PDLA: A) and Polyoxyethylene (PEG: B); PEG-PLLA-PEG and PEG-PDLA-PEG," Macromol. Biosci. 2004, 4, 361-367. Published online: Mar. 23, 2004.

Ong, et al., "Rational design of biodegradable cationic polycarbonates for gene delivery," Journal of Controlled Release 152 (2011) 120-126; Available online Jan. 26, 2011.

Sanders, et al., "A Simple and Efficient Synthesis of Functionalized Cyclic Carbonate Monomers Using a Versatile Pentafluorophenyl Ester Intermediate", J. Am. Chem. Soc. 2010, 132, 14724-14726, Published on Web Sep. 30, 2010.

Shu, et al., "In situ crosslinkable hyaluronan hydrogels for tissue engineering," Biomaterials 25 (2004) 1339-1348. Available online Oct. 14, 2003.

Tan, et al., "Delivery of Anticancer Drugs Using Polymeric Micelles Stabilized by Hydrogen-Bonding Urea Groups," Macromol. Rapid Commun. 2010, 31, 1187-1192. Published online: Jun. 22, 2010.

USPTO, NonFinal Office Action dated Feb. 15, 2013, U.S. Appl. No. 13/077,005 to Coady et al., confirmation No. 4799, application filing date Mar. 31, 2011.

USPTO, Final Office Action dated Sep. 12, 2013, U.S. Appl. No. 13/333,930 to Coady et al., confirmation No. 8777, application filing date Dec. 21, 2011.

USPTO, NonFinal Office Action dated Jun. 20, 2013, U.S. Appl. No. 13/333,930 to Coady et al., confirmation No. 8777, application filing date Dec. 21, 2011.

* cited by examiner

CATIONIC POLYMERS FOR ANTIMICROBIAL APPLICATIONS AND DELIVERY OF BIOACTIVE MATERIALS

CROSS REFERENCE TO RELATED APPLICATIONS

This application is a division of, and claims the benefit of, non-provisional U.S. patent application Ser. No. 13/333,930 entitled "CATIONIC POLYMERS FOR ANTIMICROBIAL APPLICATIONS AND DELIVERY OF BIOACTIVE MATERIALS," filed on Dec. 21, 2011, which is a continuation-in-part of, and claims the benefit of, non-provisional U.S. patent application Ser. No. 13/077,005 entitled "ANTIMICROBIAL COMPOSITIONS, METHODS OF PREPARATION THEREOF, AND USES THEREOF", filed on Mar. 31, 2011, each herein incorporated by reference in its entirety.

PARTIES TO A JOINT RESEARCH AGREEMENT

This invention was made under a joint research agreement between International Business Machines Corporation and the Agency For Science, Technology and Research.

BACKGROUND

The invention relates to cationic antimicrobial polymers for antimicrobial applications and delivery of bioactive materials, and more specifically to unimolecular cationic polycarbonates and/or polyestercarbonates for antimicrobial applications, gene delivery, and/or drug delivery.

Most conventional antibiotics (e.g., ciprofloxacin, doxycycline and ceftazidime) do not physically damage the cell wall but rather penetrate into the target microorganism and act specifically on targets such as double-stranded DNA breakage, inhibition of DNA gyrase, blockage of mitotic factors or the triggering of intrinsic autolysins. As a consequence, the bacterial morphology is preserved and the bacteria can readily develop resistance. In contrast, most cationic peptides (e.g., magainins, cecropins, protegrins and defensins) do not have a specific target in microbes, and interact with the microbial membranes through electrostatic interactions, thereby inducing terminal damage to microbial membranes.

It has been shown that macromolecular cationic antimicrobial peptides can overcome bacterial resistance. Most antimicrobial peptides possess cationic and amphiphilic features. Although efforts have been made to design antimicrobial peptides with various structures over the last two decades, clinical success has been limited. To date, only four cationic peptides have successfully entered Phase III clinical trials for wound healing. This is mainly due to cytotoxicity caused by the cationic nature of peptides (e.g., hemolysis), in vivo short half-life (labile to proteases), and high manufacturing cost.

Amphiphilic biodegradable cationic block copolycarbonates comprising hydrophilic cationic blocks and hydrophobic blocks are also limited in their use as antimicrobials. The block copolycarbonate molecules aggregate in water to form cationic micelles. Although the cationic micelles are active against Gram-positive bacteria (e.g., *Bacillus subtilus*), they are less active or non-effective against Gram-negative bacteria (e.g., *Escherichia coli*). The micelles also de-aggregate at infinite dilution, which lowers their toxicity to bacteria. Thus, the critical micelle concentration (CMC) observed with linear block copolycarbonates is currently too high for effective systemic administration of these materials.

Gene therapy holds promise for the treatment of various hereditary and acquired diseases that arise from genetic aberrations. Effective gene therapy requires three separate events. First, the genetic material which is intended to be delivered must be effectively condensed into a particle having an appropriate size to facilitate extended circulation half life. Secondly, the condensed particle must provide protection from the host organism's natural defense mechanisms, which are designed to eliminate any foreign genetic material. Finally, the nucleic acids must be unpackaged at a desired location allowing their delivery and ultimately transcription.

A continuing challenge exists in gene therapy to develop a safe and efficacious vector that can package and protect the genetic material in extracellular environments and penetrate the cell to readily release its genetic cargoes. While viral vectors have superior transduction capabilities, their extensive clinical applications have been greatly limited by significant immunogenic and carcinogenic risks, costly production, and size restrictions on the encapsulated gene. Of the various synthetic transporter materials available, poly(ethylenimine) (PEI) represents a standard for in vitro gene transfection efficiencies. However, the clinical potential of PEI has been drastically limited due to its non-biodegradability and high cytotoxicity.

Other gene delivery materials, including poly(β-amino esters) (PBAEs), modified PEIs and dendrimers based on poly(amidoamine) (PAMAM) and poly(L-lysine), are not without unresolved synthetic issues such as relatively large polydispersities, complex molecular architectures requiring multiple production steps, and high cost of starting materials (in the case of amino acids). A narrow molecular weight system is believed to be crucial in the clinical settings as individual molecular weight fractions of a polydisperse system are expected to exhibit distinct pharmacological activities in vivo.

Currently, a growing and urgent need exists for enzymatically biodegradable, non-cytotoxic antimicrobial materials that i) exhibit higher toxicity toward a combination of Gram-negative and Gram-positive microbes, and ii) disperse in aqueous solution as unimolecular nanostructures having an average particle diameter of 10 nm to 300 nm. This size range is generally suitable for cell wall penetration, and potentially expands the utility and value of the antimicrobial materials as multi-use delivery vehicles for genes and/or drugs.

SUMMARY

Accordingly, a cationic star polymer is disclosed having the formula (1):

wherein
w' is a positive number greater than or equal to 3,
I' is a dendritic polyester core covalently linked to w' independent peripheral linear cationic polymer chains P',
each of the chains P' comprises a cationic repeat unit comprising i) a backbone functional group selected from the group consisting of aliphatic carbonates, aliphatic esters, aliphatic carbamates, aliphatic ureas, aliphatic thiocarbamates, aliphatic dithiocarbonates, and combinations thereof, and ii) a side chain comprising a quaternary amine group, and the quaternary amine group comprises a divalent methylene group directly covalently linked to i) a positive charged nitrogen and ii) an aromatic ring.

A method of forming the foregoing cationic star polymer is disclosed, which comprises:

forming a mixture containing i) an organocatalyst, ii) an optional accelerator, iii) a solvent, iv) a dendritic polyester initiator comprising 3 or more peripheral nucleophilic initiator groups for ring opening polymerization (ROP), and v) a cyclic carbonyl monomer comprising a pendant electrophilic group capable of reacting with a tertiary amine to form a quaternary amine;

agitating the mixture, thereby forming an electrophilic polymer by ROP;

optionally endcapping the electrophilic polymer, thereby forming an endcapped electrophilic polymer; and treating the electrophilic polymer and/or the endcapped electrophilic polymer with the tertiary amine, thereby forming the cationic star polymer.

Also disclosed is a cationic star polymer comprising: 3 or more peripheral monovalent linear cationic polymer chains P' independently covalently linked to a dendritic polyester core I', wherein each of the chains P' comprises a cationic repeat unit of the general formula (11):

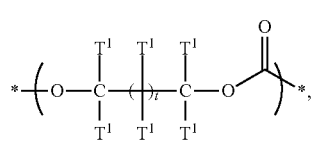

(11)

wherein I) t is an integer from 0 to 6, II) each $T^1$ is a monovalent radical independently selected from the group consisting of hydrogen, and functional groups comprising 1 to 30 carbons, and III) at least one $T^1$ group comprises a quaternary amine group, the quaternary amine group comprising a divalent methylene group that is directly covalently linked to i) a positive charged nitrogen and ii) an aromatic ring.

Further disclosed is a cationic graft polymer of formula (1):

(1)

wherein w' is a positive number greater than or equal to 3,

I' is a core comprising a multivalent linear aliphatic polycarbonate,

I' is covalently linked to w' independent monovalent cationic polymer chains P', each of the chains P' comprises a cationic repeat unit comprising i) a backbone functional group selected from the group consisting of aliphatic carbonates, aliphatic esters, aliphatic carbamates, aliphatic ureas, aliphatic thiocarbamates, aliphatic dithiocarbonates, and combinations thereof, and ii) a side chain comprising a quaternary amine group, and the quaternary amine group comprises a divalent methylene group that is directly covalently linked to i) a positive charged nitrogen and ii) an aromatic ring.

A method of forming the foregoing cationic graft polymer is disclosed, comprising:

forming a mixture containing i) an organocatalyst, ii) an optional accelerator, iii) a solvent, iv) a cyclic carbonyl monomer comprising a pendant electrophilic group capable of reacting with a tertiary amine to form a quaternary amine, and a cyclic carbonyl group selected from the group consisting of aliphatic cyclic carbonates, aliphatic cyclic esters, aliphatic cyclic carbamates, aliphatic cyclic ureas, aliphatic cyclic thiocarbamates, aliphatic cyclic dithiocarbonates, and combinations thereof, and v) an initiator comprising a linear aliphatic polycarbonate comprising 3 or more side chain nucleophilic groups capable of initiating a ring opening polymerization (ROP);

agitating the mixture, thereby forming an electrophilic polymer by ROP of the cyclic carbonyl monomer;

optionally endcapping the electrophilic polymer, thereby forming an endcapped electrophilic polymer; and treating the electrophilic polymer or the endcapped electrophilic polymer with a tertiary amine, thereby forming the cationic graft polymer.

Also disclosed is a cationic graft polymer comprising a multivalent linear aliphatic polycarbonate core I' comprising 3 or more side chains, the side chains comprising independent monovalent cationic polymer chains P' covalently linked by respective end units to the side chains, wherein each of the chains P' comprises a cationic repeat unit of the general formula (11):

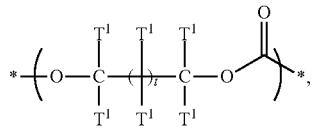

(11)

wherein I) t is an integer from 0 to 6, II) each $T^1$ is a monovalent radical independently selected from the group consisting of hydrogen, and groups comprising 1 to 30 carbons, and III) at least one $T^1$ group comprises a quaternary amine group, the quaternary amine group comprising a divalent methylene group directly covalently linked to i) a positive charged nitrogen and ii) an aromatic ring.

A method of killing a microbe is disclosed, which comprises contacting the microbe with any of the foregoing cationic polymers.

An injectable composition is disclosed, which comprises an aqueous mixture of any of the foregoing cationic polymers.

A method of treating a cell is disclosed, which comprises contacting the cell with a composition comprising i) any of the above cationic polymers and ii) a gene and/or a drug.

An article is disclosed which comprises any of the above cationic graft polymers disposed on a surface of a medical device.

A cationic star polymer is disclosed of formula (1):

(1)

wherein w' is a positive number greater than or equal to 3,

I' is a multivalent hydrophobic core covalently linked to w' independent peripheral linear cationic polymer chains P', each of the chains P' comprises a cationic repeat unit comprising i) a backbone functional group selected from the group consisting of aliphatic carbonates, aliphatic esters, aliphatic carbamates, aliphatic ureas, aliphatic thiocarbamates, aliphatic dithiocarbonates, and combinations thereof, and ii) a side chain comprising a quaternary amine group, and the quaternary amine group comprises a divalent methylene group directly covalently linked to i) a positive charged nitrogen and ii) an aromatic ring.

The above-described and other features and advantages of the present invention will be appreciated and understood by those skilled in the art from the following detailed description, drawings, and appended claims.

DETAILED DESCRIPTION

Figure 1:
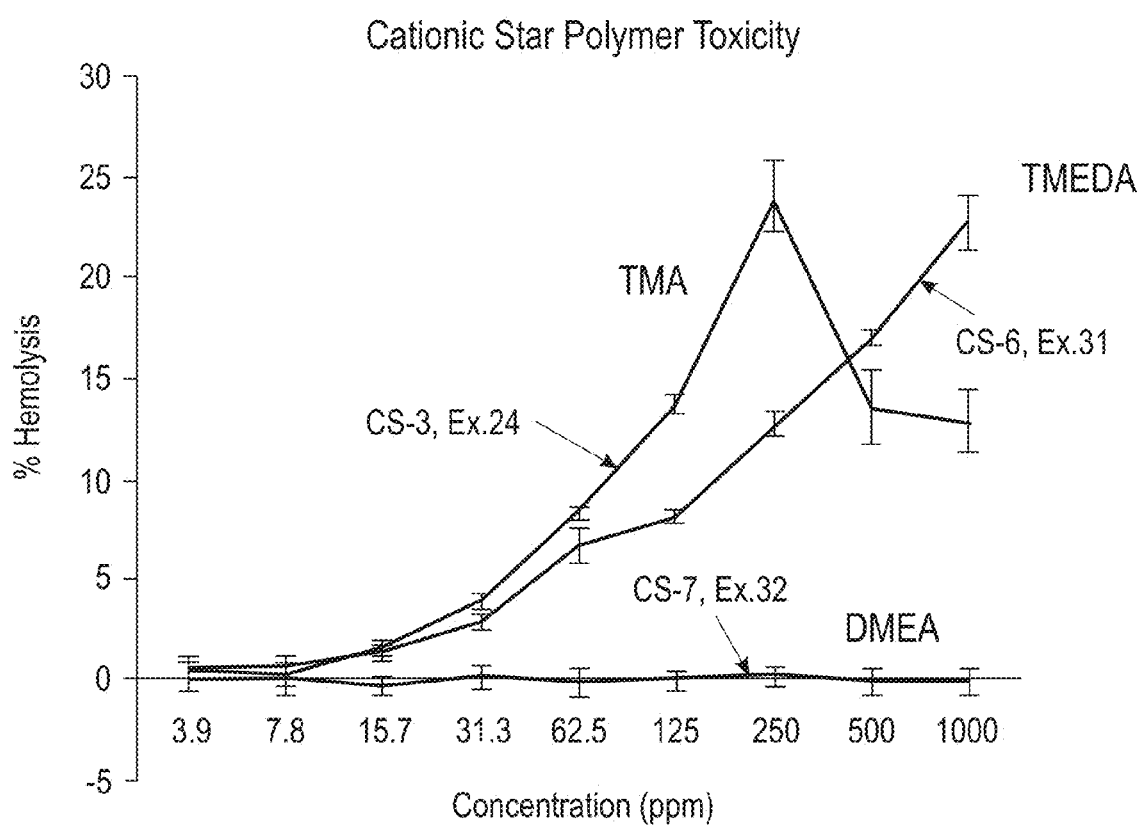
FIG. 1 is a graph of % hemolysis as a function of concentration in parts per million (ppm) of cationic star polymers CS-3 (Example 24), CS-6 (Example 31), and CS-7 (Example 32) formed from the same electrophilic star polymer ES-2 having a G''' core structure (32 arms), and quaternized with different amines: trimethylamine (TMA) (CS-3), N,N,N',N'-tetramethylethylenediamine (TMEDA) (CS-6), and N,N-dimethylethanolamine (DMEA) (CS-7).

The antimicrobial cationic polymers of this invention have a structure according to general formula (1):

$$I'\!-\!\!+\!P']_{w'},\qquad(1)$$

wherein w' is a positive number greater than or equal to 3 and can represent an average value. I' is a multivalent hydrophobic core structure covalently linked to each of w' independent monovalent cationic polymer chains P' by independent divalent linking groups L' of I'. That is, the linking groups L' are represented herein as sub-structures of I'. Each of the chains P' comprises a cationic repeat unit comprising i) an backbone functional group selected from the group consisting of aliphatic carbonates, aliphatic esters, aliphatic carbamates, aliphatic ureas, aliphatic thiocarbamates, aliphatic dithiocarbonates, and combinations thereof, and ii) a side chain comprising a quaternary amine group. In an embodiment, the cationic repeat unit comprises an aliphatic carbonate group and/or an aliphatic ester group. The quaternary amine group is covalently bound to the side chain of the cationic repeat unit. The quaternary amine group comprises a divalent methylene group, which is bonded to i) a positive charged nitrogen and ii) an aromatic ring (e.g., a quaternary nitrogen having a benzyl substituent).

The minimum inhibitory concentration (MIC) of the cationic polymers can be much less than 500 mg/L against one or more microbes, which can include Gram-positive and/or Gram-negative microbes. More particularly, the MIC can be less than 400 mg/L, less than 300 mg/L, or less than 200 mg/L against one or more Gram-positive and/or Gram-negative microbes.

Herein, a "cationic star polymer" comprises an aliphatic polyester dendritic core I'. A "cationic graft polymer" comprises a linear aliphatic polycarbonate or a linear aliphatic polyestercarbonate (i.e., a polymer having a backbone comprising aliphatic ester repeat units and aliphatic carbonate repeat units) core I'.

In the description that follows, the term "cationic polymer" should be understood to mean cationic star polymer and/or cationic graft polymer unless otherwise indicated.

The cationic polymers are amphiphilic, capable of dispersing as unimolecular non-crosslinked nanoparticles in aqueous solution. The non-crosslinked cationic polymers are less susceptible to dilution effects and have greater antimicrobial activity compared to aqueous solutions of known non-crosslinked polycarbonates and polyestercarbonates. The cationic polymers can be used as standalone antimicrobial agents (i.e., not requiring an additional agent such as a polymer and/or a drug). The cationic polymers exhibit high toxicity to Gram-negative microbes, Gram-positive microbes, and yeasts. The cationic polymers are less cytotoxic compared to the standard reference polymer poly (ethyleneimine) (PEI) used in gene therapy. Aqueous nanoparticles of the non-crosslinked cationic polymers can have an average particle diameter of 50 nm to 250 nm. The cationic polymers can be biocompatible and/or substantially enzymatically biodegradable. In some cases, a complex of cationic polymer with a DNA can be as efficient in gene expression as a complex of PEI with the DNA.

The negative charged counterion of the quaternary amine group can be a covalently bound ionic group of chain P' (e.g., a side chain carboxylate ion), or an ionic group (e.g., chloride ion) that is not covalently bound to chain P'. In an embodiment, the cationic repeat unit comprises an aliphatic backbone carbonate group. In another embodiment, the cationic repeat unit comprises an aliphatic backbone ester group. An optional non-charged repeat unit of chains P' can comprise a backbone functional group selected from the group consisting of aliphatic carbonates, aliphatic esters, aliphatic carbamates, aliphatic ureas, aliphatic thiocarbamates, aliphatic dithiocarbonates, and combinations thereof.

Core structure I' and/or chains P' can comprise stereospecific and/or non-stereospecific repeat units. Core structure I' is preferably substantially or completely non-charged and hydrophobic. Peripheral chains P' are positive charged and can comprise a hydrophobic repeat unit(s) in the form of a random copolymer or block copolymer structure with the hydrophilic cationic repeat unit.

Preferably, the dendritic chemical structure of I' of a cationic star polymer is essentially free of carboxylic esters of phenolic alcohols, exemplified by the following non-limiting structures:

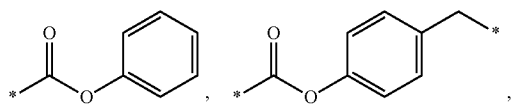

wherein the starred bonds represent attachment points to other portions of the chemical structure of I'.

"Essentially free of carboxylic esters of phenolic alcohols" means that carboxylic esters of phenolic alcohols are not present in sufficient amount to cause an adverse effect on the antimicrobial properties of the cationic star polymers. In an embodiment, the dendritic chemical structure of I' of the cationic star polymer excludes carboxylic esters of phenolic alcohols. The exclusion arises from the unexpected finding that cationic star polymers prepared using dendritic ROP initiators, such as D-1 and G-2(OH)$_{12}$ (below) readily degrade in aqueous and/or organic protic media. Degradation can occur at low and/or high pH.

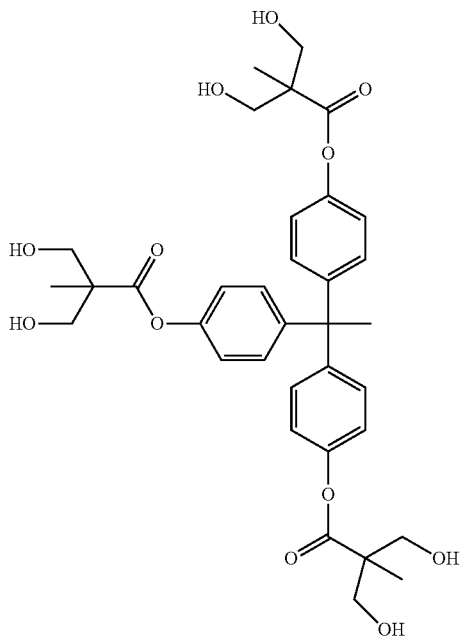

D-1

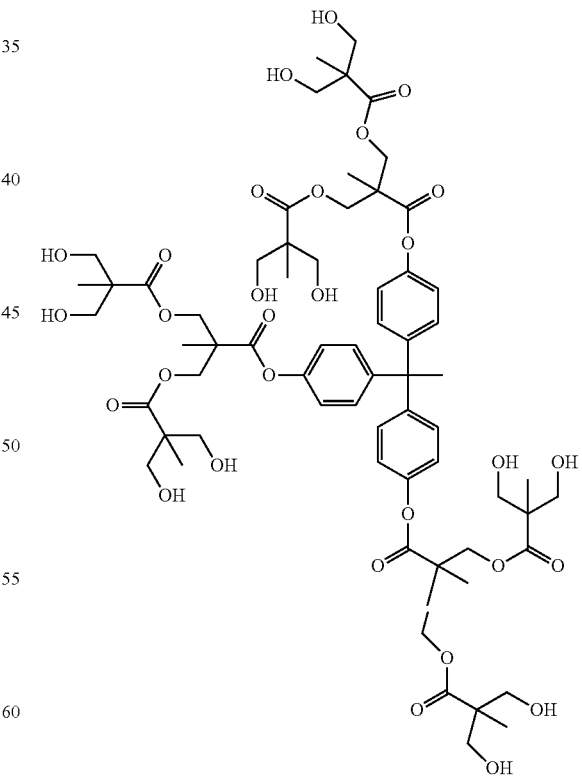

G-2(OH)$_{12}$

By comparison, little or no degradation was observed for G-1(OH)$_8$, a pentaerythritol based dendrimer having no carboxylic ester groups of phenolic alcohols.

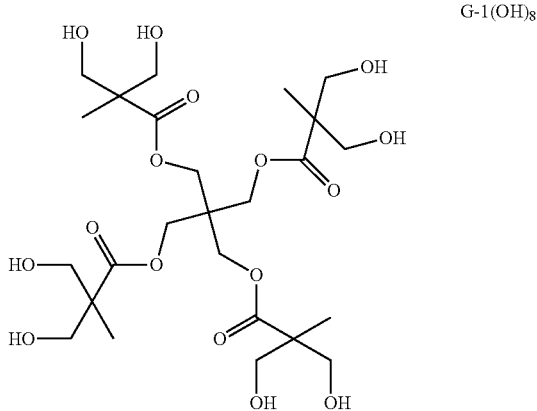 [SMILES: CC(CO)(CO)C(=O)OCC(COC(=O)C(C)(CO)CO)(COC(=O)C(C)(CO)CO)COC(=O)C(C)(CO)CO]

G-1(OH)₈

The term "biodegradable" is defined by the American Society for Testing and Materials as a degradation caused by biological activity, especially by enzymatic action, leading to a significant change in the chemical structure of the material. For purposes herein, a material is "biodegradable" if it undergoes 60% biodegradation within 180 days in accordance with ASTM D6400. Herein, a material is "enzymatically biodegradable" if the material can be degraded (e.g., depolymerized) by a reaction catalyzed by an enzyme.

A "biocompatible" material is defined herein as a material capable of performing with an appropriate host response in a specific application.

Herein, a material is "not effective" as an antimicrobial agent if the material performs about the same as the phosphate buffered saline (PBS) control solution, and/or has a minimum inhibitory concentration (MIC) greater than 500 mg/L.

Herein, a "stereospecific repeat unit" i) has a non-superposable mirror image and ii) comprises one or more asymmetric tetravalent carbons. Each asymmetric tetravalent carbon is assigned an R or S symmetry based on Cahn-Ingold-Prelog (CIP) symmetry rules. Each asymmetric tetravalent carbon can be present in a stereoisomeric purity of 90% to 100%, 94% or more, or more particularly 98% to 100%. For example, if the stereospecific repeat unit has two asymmetric tetravalent carbons, the stereospecific repeat unit can be present substantially as the R,R stereoisomer, substantially as the R,S stereoisomer, substantially as the S,S stereoisomer, or substantially as the S,R stereoisomer.

A "stereospecific cyclic carbonyl monomer" i) has a non-superposable mirror image and ii) comprises one or more asymmetric tetravalent carbons. The stereospecific cyclic carbonyl monomer can have a stereoisomeric purity of 90% or more, and more particularly 98% or more. In an embodiment, at least one of the asymmetric tetravalent carbons of the stereospecific cyclic carbonyl monomer is a ring carbon that becomes a polymer backbone carbon in a ring opening polymerization.

"Restricted metals" herein include ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium. Each one of the foregoing restricted metals can have a concentration in the cationic polymer of 0 parts to 100 ppm (parts per million), 0 parts to 100 ppb (parts per billion), or 0 parts to 100 ppt (parts per trillion). Preferably, each one of the foregoing restricted metals has a concentration of 0 parts in the cationic polymer (i.e., the concentration is below detection limits).

No restriction is placed on the concentration of boron, silicon, or any individual alkali metal in the cationic polymer, providing the antimicrobial properties of the cationic polymer are not adversely affected.

The cationic polymer can be used without an additional biologically active substance (e.g., by applying the cationic polymer as an antimicrobial agent in the form of a liquid solution or a powder to a wound surface). Alternatively, the cationic polymer can serve as a delivery vehicle for a biologically active substance that forms a complex with the cationic polymer by non-covalent interactions. This complex is referred to as a loaded complex. The loaded complex is preferably reversible. For example, the loaded complex can enter a cell by endocytosis and release the biologically active substance at a desired stage within the cell or tissues (in the case where the active substance is the cell). Biologically active substances include cells, biomolecules (e.g., DNA, genes, peptides, proteins, enzymes, lipids, phospholipids, and nucleotides), natural or synthetic organic compounds (e.g., drugs, dyes, synthetic polymers, oligomers, and amino acids), inorganic materials (e.g., metals and metal oxides), radioactive variants of the foregoing, and combinations of the foregoing.

"Biologically active" means the referenced material can alter the chemical structure and/or activity of a cell in a desirable manner, or can selectively alter the chemical structure and/or activity of a cell type relative to another cell type in a desirable manner. As an example, one desirable change in a chemical structure can be the incorporation of a gene into the DNA of the cell. A desirable change in activity can be the expression of the transfected gene. Another change in cell activity can be the induced production of a desired hormone or enzyme. Alternatively, a desirable change in activity can be the selective death of one cell type over another cell type. No limitation is placed on the relative change in cellular activity caused by the biologically active substance, providing the change is desirable and useful. Moreover, no limitation is placed on the biologically active substance complexed with the cationic polymer, providing the biologically active substance induces a useful cellular response when released from the loaded complex.

The following structures illustrate quaternary amines in which a divalent methylene group is directly covalently linked to a positive charged nitrogen and an aromatic ring (indicated by the arrows):

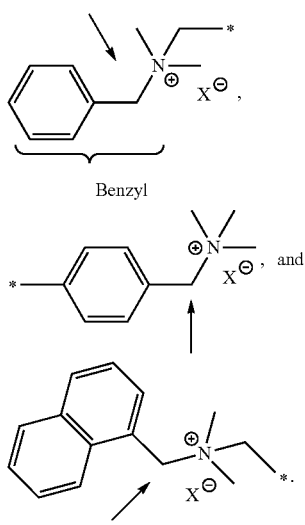

Benzyl

The starred bonds in the above structures represent attachment points to other portions of the cationic repeat unit. X⁻ is a negative charged counterion. In the simplest example, the quaternary nitrogen (positive charged nitrogen of the quaternary amine) is directly linked to at least one benzyl group, as shown above. The aromatic ring directly linked to the divalent methylene group can comprise 0 or more substituents in addition to the methylene group.

Without being bound by theory, the presence of the aromatic ring in close proximity to the quaternary nitrogen is believed to enhance the ability of the quaternary amine group to bind with and/or penetrate the microbial cell wall. As the Examples further below demonstrate, the presence of the aromatic ring increases the antimicrobial activity (i.e., lowers the minimum inhibitory concentration (MIC)) against Gram-negative and Gram-positive microbes compared to otherwise structurally similar cationic polymers lacking a benzyl substituent linked to the quaternary nitrogen, such as cationic polymers bearing the following quaternary amine group:

A less preferred convergent synthetic approach for the preparation of the cationic polymers comprises i) coupling a preformed electrophilic precursor chain P' to a pre-formed precursor core structure I' using suitable linking chemistry, thereby forming an electrophilic polymer, and ii) treating the electrophilic polymer with a tertiary amine, thereby forming a cationic polymer of formula (1). This convergent synthetic approach allows for greater functional diversity in the chemical structures and charge densities of the individual chains P' of the cationic polymer. The pre-formed precursor core structure I' and/or the pre-formed electrophilic precursor chain P' can be prepared by organocatalyzed ring opening polymerization (ROP).

A preferred sequential method of forming the cationic polymers of formula (1) comprises i) forming a mixture containing an electrophilic cyclic carbonyl monomer comprising a pendant electrophilic group capable of reacting with a tertiary amine to form a quaternary amine, a linear polymeric and/or dendritic ROP initiator (a precursor to core structure I' in the cationic polymer) comprising 3 or more nucleophilic ROP initiator groups, an organocatalyst, an optional accelerator, and a solvent;

ii) agitating the mixture, thereby forming an electrophilic polymer by ROP;

iii) optionally endcapping the electrophilic polymer, thereby forming an endcapped electrophilic polymer; and iv) treating the electrophilic polymer or the endcapped electrophilic polymer with a tertiary amine, thereby forming a cationic polymer of formula (1).

Scheme 1 illustrates a non-limiting example of a sequential ROP method for preparing a cationic star polymer derived from an aliphatic polyester dendrimer initiator.

Scheme 1.

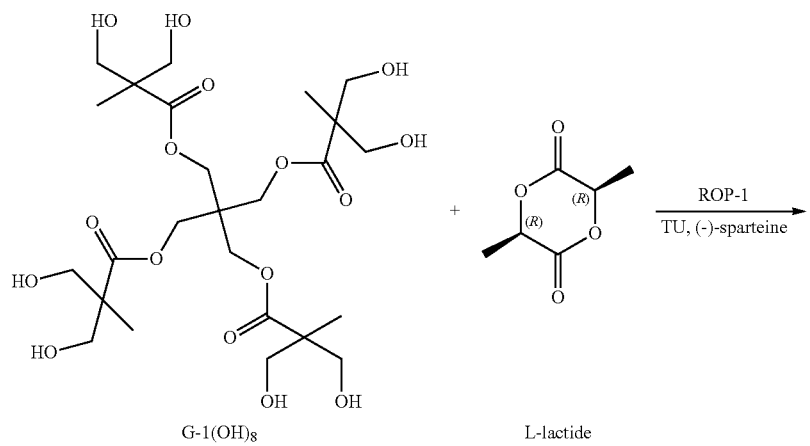

G-1(OH)₈          L-lactide

-continued
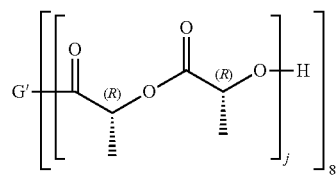
Intermediate-1
i) 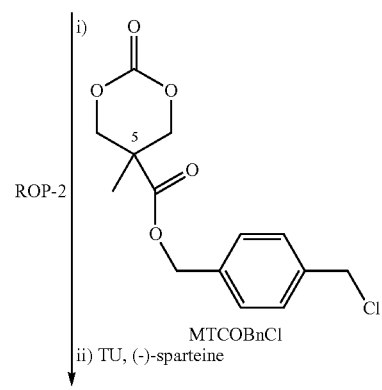
MTCOBnCl
ROP-2
ii) TU, (-)-sparteine
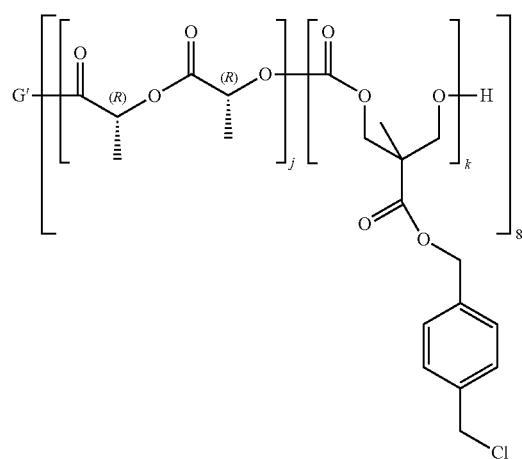
Electrophilic Polymer
End cap | Ac₂O

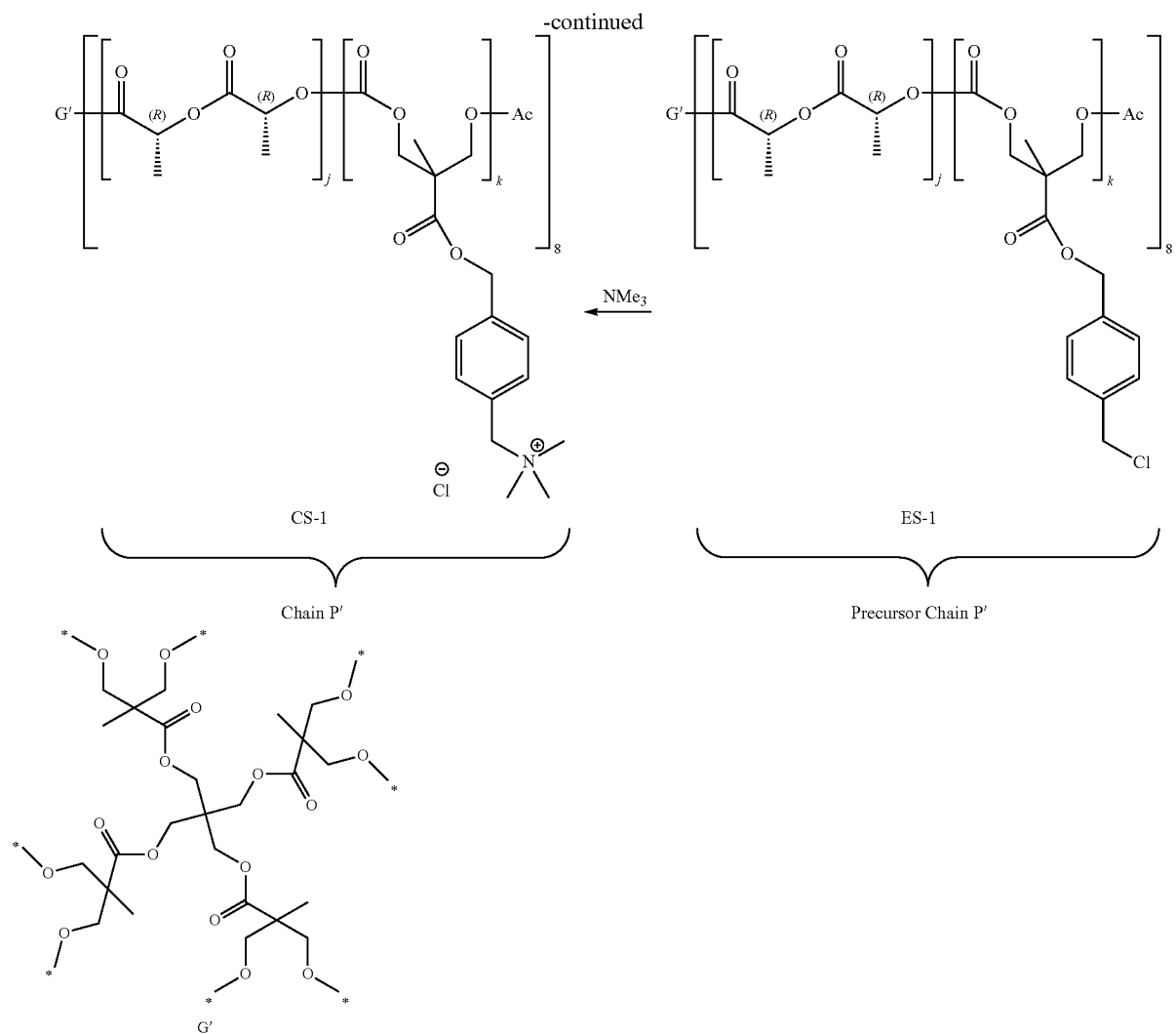

Endcapped electrophilic polymer ES-1 is prepared by sequentially polymerizing (and ROP-2) of L-lactide, non-charged cyclic ester monomer in ROP-1 followed by MTCOBnCl, an electrophilic cyclic carbonate monomer in ROP-2. ROP-1 is initiated by a first generation aliphatic dendritic polyol initiator, G-1(OH)$_8$ (branched aliphatic polyester having 8 peripheral hydroxy groups). ROP-2 is initiated by the living end unit of the poly(L-lactide) chain formed in ROP-1. ROP-1 and ROP-2 can optionally be performed in a single pot. Subscripts j and k in the above structures of Scheme 1 represent average numbers of repeat units derived from each monomer in each of the precursor chains P'. L-lactide is shown with R,S-stereochemistry, which is preserved in the ROP. In the above non-limiting example, each of the precursor chains P' of ES-1 comprises an electrophilic repeat unit comprising a chlorobenzyl side chain group, which is capable of reacting with a tertiary amine (e.g., trimethylamine) to form a side chain quaternary amine group. In this instance, the hydroxyl containing end unit of the electrophilic polymer has been optionally endcapped as an acetate ester before the quaternization. The endcapped electrophilic polymer ES-1 and/or the non-endcapped electrophilic polymer can be treated with a tertiary amine to form a cationic star polymer. Reaction of ES-1 with trimethylamine produces cationic star polymer CS-1 comprising chains P' having a side chain quaternary amine group in accordance with formula (1). The positive charged nitrogen of the quaternary amine group comprises a para-substituted benzyl moiety. In this example, chains P' of CS-1 have a block copolymer structure, indicated by the sequential order of the bracketed repeat units in the polymer chain. Each of the divalent oxygens in G' having a starred bond is a divalent linking group L' of I'. The divalent oxygen linking groups L' are residues of the hydroxy initiator groups of G1-(OH)$_8$.

G1-(OH)$_8$ is an example of a dendritic P'-ROP initiator (i.e., "P'-ROP initiator" is a term used herein to distinguish the ROP initiator used to form precursor chains P'). The P'-ROP initiator preferably comprises 3 or more, preferably 8 or more nucleophilic ROP initiator groups (e.g., hydroxy groups). Other examples of dendritic P'-ROP initiators include G-2(OH)$_{16}$, and G-3(OH)$_{32}$:

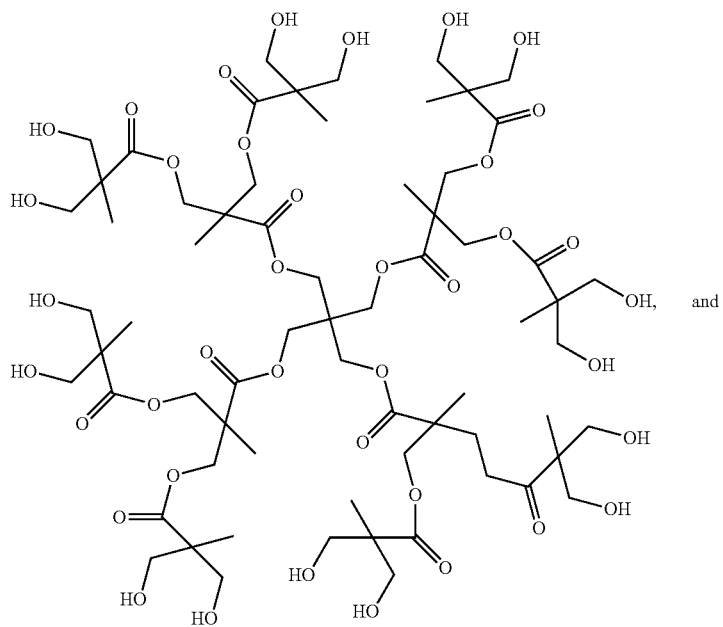
G-2(OH)16
and
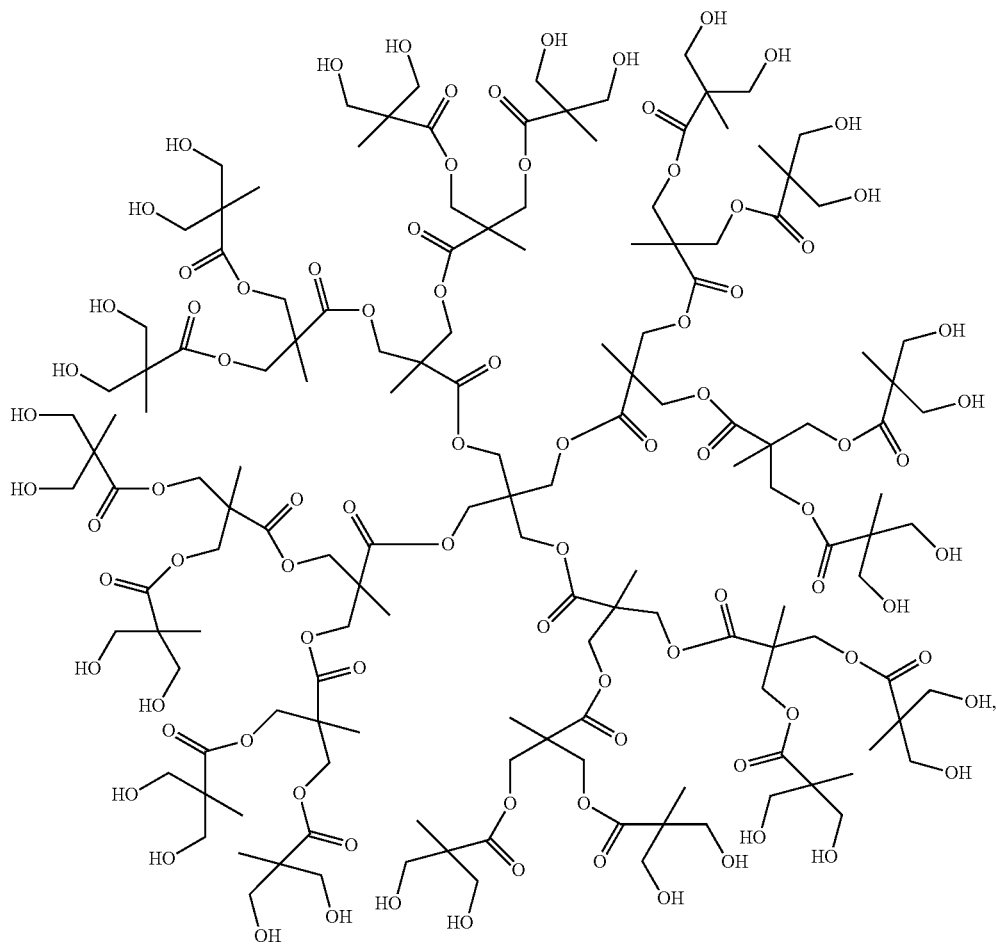
G-3(OH)32

These and other polyol dendrimers can be prepared by known methods in the art. The dendritic P'-ROP initiators comprise a plurality of peripheral nucleophilic end groups capable of initiating a ROP. Preferred dendritic P'-ROP initiators comprise a plurality of branches comprising repeat units comprising carboxylic esters of aliphatic alcohol groups.

A carboxylic ester of an aliphatic alcohol group comprises an aliphatic carbon bonded to the ester oxygen, exemplified by the following non-limiting examples:

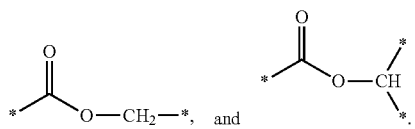

The starred bonds in the above carboxylic esters indicate attachment points to other portions of the compound. The dendritic P'-ROP initiators are not restricted in the number of generational layers or the number of branches. The dendritic P'-ROP initiators are preferably essentially free of carboxylic esters of phenolic alcohols. In an embodiment, the chemical structure of the dendritic P'-ROP initiators excludes carboxylic esters of phenolic alcohols.

The first generation carboxylic ester branches of the dendritic P'-ROP initiators are covalently linked to a multivalent monomeric core group, referred to herein as a the C' group, which is preferably derived from a monomeric aliphatic polyol (e.g., pentaerythritol, erythritol, etc.). In the above examples of G-1(OH)$_8$, G-2(OH)$_{16}$, and G-3(OH)$_{32}$ the C' group of the dendritic P'-ROP initiator is a pentaerythritolyl group C(CH$_2$O*)$_4$. The first generation dendritic branches of the dendritic P'-ROP initiator can be prepared by esterification of this monomeric aliphatic polyol.

Additional examples of C' groups include the structures of Table 1 and stereoisomers thereof. Asymmetric carbon centers are labeled with R,S stereochemistry. In Table 1, starred bonds represent potential attachment points to a dendritic branch of the P'-ROP initiator. One or more of the oxygens having a starred bond can be individually attached to an alkyl group such as a methyl and/or ethyl group, as long as at least three sites of attachment to dendritic branches are present in a C' group.

TABLE 1

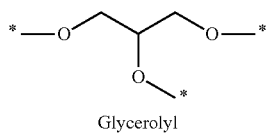

Glycerolyl

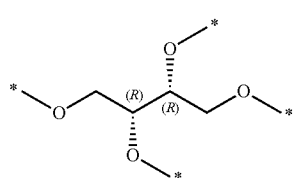

Threitolyl

TABLE 1-continued

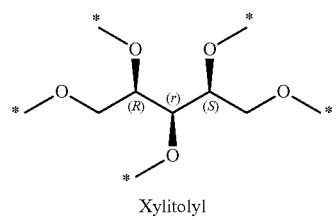

Xylitolyl

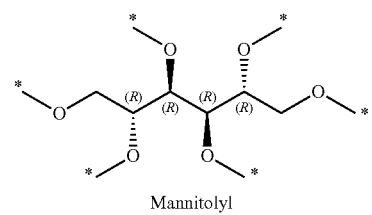

Mannitolyl

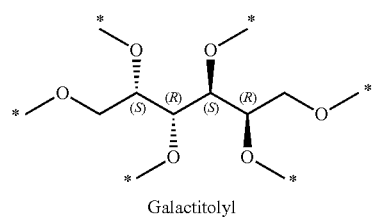

Galactitolyl

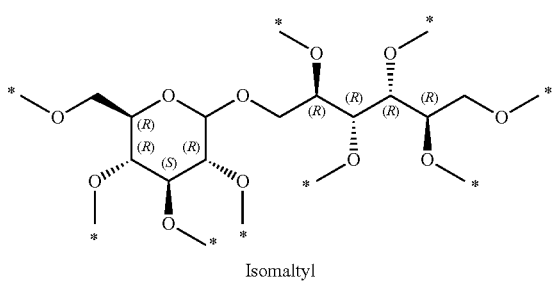

Isomaltyl

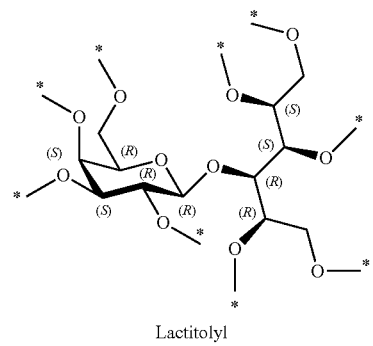

Lactitolyl

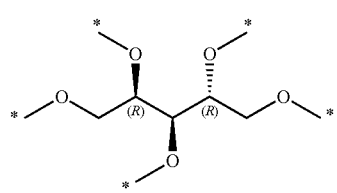

Arabitolyl

TABLE 1-continued

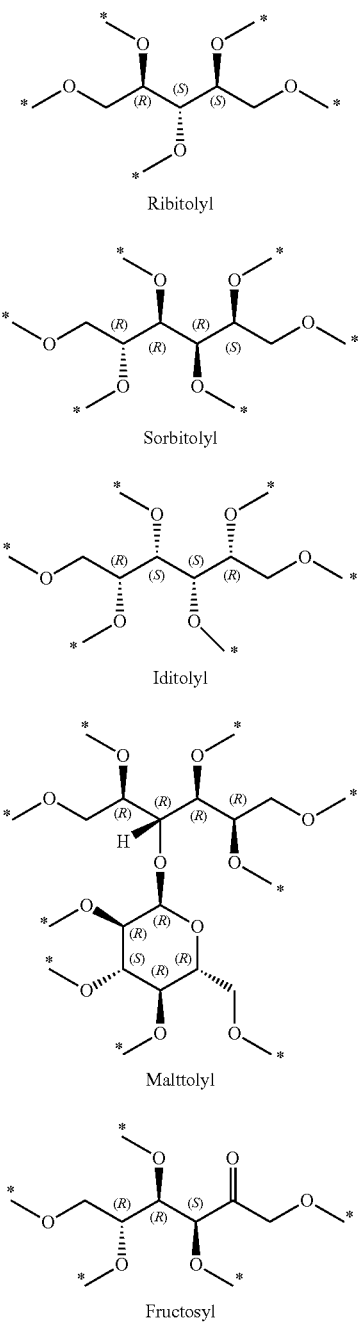

Ribitolyl

Sorbitolyl

Iditolyl

Malttolyl

Fructosyl

As indicated by the structures in Table 1, the C' groups of the dendritic P'-ROP initiator can comprise other functional groups, for example ketones, ketals, acetals, esters, amides, and combinations thereof.

The nucleophilic initiator groups of the dendritic P'-ROP initiator and other P'-ROP initiators described below can comprise alcohols, primary amines, secondary amines, thiols, and/or mixtures thereof. Preferred P'-ROP initiators comprise primary alcohol initiator groups.

The electrophilic cyclic carbonyl monomer used in the preparation of precursor chains P' is preferably a cyclic carbonate monomer and/or a cyclic ester monomer, having a pendant electrophilic group capable of reacting with a tertiary amine to form a quaternary amine after the ring opening polymerization (e.g., MTCOPrCl (Table 4 further below) and MTCOBnCl (Scheme 1 above)).

The electrophilic repeat unit of precursor chains P' preferably comprises an aliphatic backbone carbonate group and/or an aliphatic backbone ester group. Precursor chains P' can comprise a homopolymer, random copolymer, and/or block copolymer chain comprising the electrophilic repeat unit. Precursor chains P' can have a living end unit comprising a nucleophilic group capable of initiating a ROP. As shown in Scheme 1, precursor chains P' of the electrophilic polymer can optionally be endcapped.

The P'-ROP initiator can be a linear aliphatic polycarbonate or a linear aliphatic polyestercarbonate polymer comprising a plurality of ROP initiator groups, referred to herein as a linear polymeric P'-ROP initiator. The linear polymeric P'-ROP initiator are used to prepare the cationic graft polymers. The linear polymeric P'-ROP initiator comprises a nucleophilic repeat unit, which has i) a backbone functional group selected from the group consisting of aliphatic carbonates, aliphatic esters, aliphatic carbamates, aliphatic ureas, aliphatic thiocarbamates, aliphatic dithiocarbonates, and combinations thereof, and ii) a side chain comprising a nucleophilic ROP initiator group. The nucleophilic repeat unit preferably comprises an aliphatic backbone carbonate group or an aliphatic backbone ester group. Each end unit of the linear polymeric P'-ROP initiator can also comprise a ROP initiator group. The linear polymeric P'-ROP initiator comprises 3 or more, preferably 8 or more, nucleophilic groups capable of initiating a ROP. The linear polymeric P'-ROP initiator can comprise a homopolymer, random copolymer, and/or block copolymer chain comprising the nucleophilic repeat unit.

PC-1 (see also Example 13 further below) exemplifies a linear polymeric P'-ROP initiator (linear polycarbonate) comprising a nucleophilic repeat unit having a backbone aliphatic carbonate group and a side chain aliphatic alcohol:

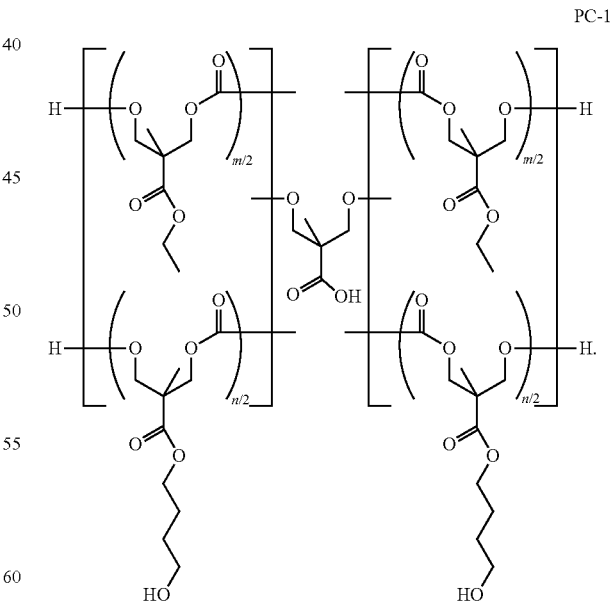

PC-1

The vertical stacking of repeat units in PC-1 above indicates a random distribution of repeat units in the copolymer chain. In this example, the PC-1 chain is not endcapped. Subscripts m and n in the above structure represent the average number of each repeat unit per chain. Using a linear polymeric P'-ROP initiator and organocatalyzed ROP, the precursor chains P' can be grown as extensions of the side chain nucleophilic initiator groups and optionally the nucleophilic groups of the non-endcapped end units of the linear polymeric P'-ROP initiator, thereby forming an electrophilic graft copolymer (i.e., a precursor to a cationic graft copolymer).

EG-1 (below) exemplifies an electrophilic graft copolymer produced in the above-described manner using the cyclic carbonyl monomers L-lactide and MTCOBnCl:

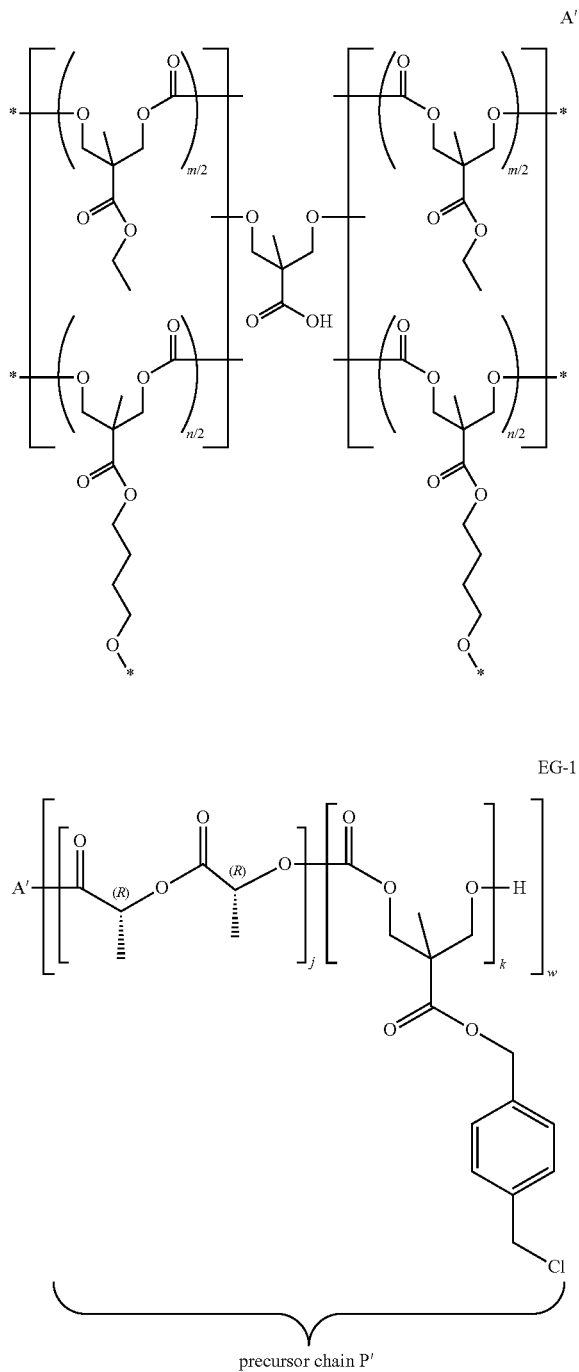

In the above structure of EG-1, the divalent oxygens having the starred bonds in A' are divalent linking groups L' of core structure I' of EG-1. These divalent oxygens are also divalent linking groups L' of I' in the cationic graft polymer formed from EG-1.

In the above example, precursor chains P' of EG-1 have a block copolymer structure, indicated by the sequential order of the bracketed repeat units in the polymer chain. The endcapped or non-endcapped electrophilic polymer (EG-1) can be treated with a tertiary amine as described further above in a reaction with the chlorobenzyl-containing side chain to form a cationic graft polymer comprising a quaternary amine group (e.g., Example 25, CG-1). Precursor chain P' of EG-1 can be performed in a single pot. Subscripts j and k in the above structure of EG-1 represent average numbers of repeat units in a precursor chain P'. L-lactide is shown with R,S-stereochemistry, which is preserved in the ROP.

The linear polymeric P'-ROP initiator can also be prepared by organocatalyzed ROP. In this instance, the ROP utilizes a cyclic carbonyl monomer bearing a pendant protected ROP initiator group, preferably a protected alcohol group, and a mono-nucleophilic or di-nucleophilic ROP initiator (e.g., mono-alcohol and/or diol). The mono-nucleophilic or di-nucleophilic ROP initiator is referred to herein as an I'-ROP initiator. The cyclic carbonyl monomer bearing a pendant protected ROP initiator group comprises i) a cyclic carbonyl functional group selected from the group consisting of cyclic carbonates, cyclic esters, cyclic carbamates, cyclic ureas, cyclic thiocarbamates, cyclic dithiocarbonates, and combinations thereof, and ii) a side chain comprising a protected nucleophilic ROP initiator group. In an embodiment, the cyclic carbonyl monomer bearing a pendant protected ROP initiator group, which is used to form the P'-ROP initiator, is selected from the group consisting of a cyclic carbonate monomers, cyclic ester monomers (lactones), and combinations thereof.

A method of forming the linear polymeric P'-ROP initiator comprises i) forming a mixture comprising a cyclic carbonyl monomer bearing a protected ROP initiator group, an I'-ROP initiator comprising 1 or 2 nucleophilic ROP initiator groups, an organocatalyst, an optional accelerator, and a solvent, ii) agitating the mixture, thereby forming a protected linear polymeric P'-ROP initiator, and iii) deprotecting the protected linear polymeric P'-ROP initiator, thereby forming the linear polymeric P'-ROP initiator.

The protected linear polymeric P'-ROP initiator comprises a protected repeat unit comprising i) a backbone functional group selected from the group consisting of aliphatic carbonates, aliphatic esters, aliphatic carbamates, aliphatic ureas, aliphatic thiocarbamates, aliphatic dithiocarbonates, and combinations thereof, and ii) a side chain comprising a protected nucleophilic ROP initiator group. The protected P'-ROP initiator can comprise a homopolymer, random copolymer, and/or block copolymer chain comprising the protected repeat unit. Scheme 2 (see also Example 13) illustrates the preparation of a linear polymeric P'-ROP initiator, PC-1.

Scheme 2.

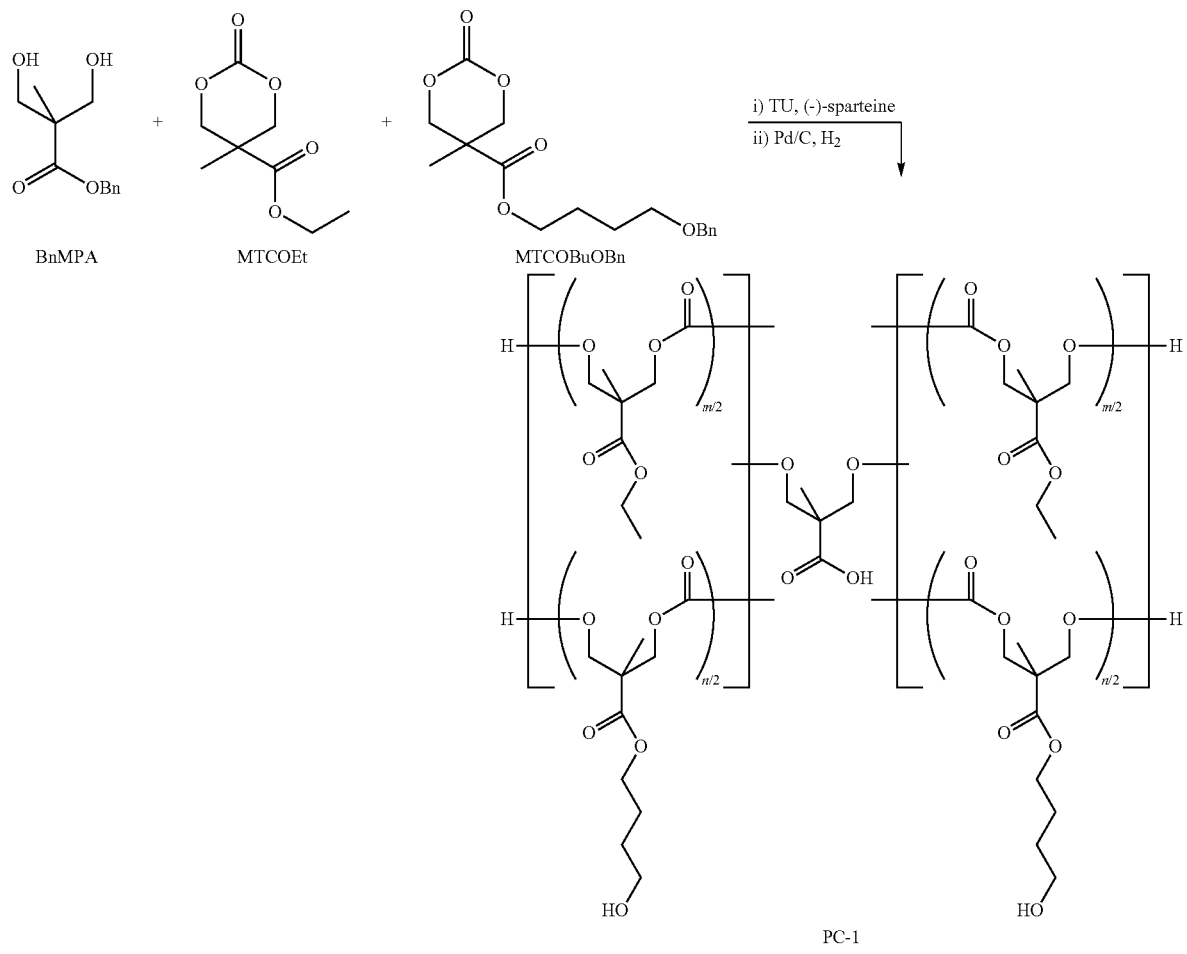

Bn = benzyl

In this example, the monomeric I'-ROP initiator used in the preparation of PC-1 is BnMPA (benzyl ester of 2,2-bis (methylol)propionic acid), which comprises 2 primary alcohol initiator groups. PC-1 is a linear random copolymer produced by ROP of a mixture comprising MTCOBuOBn, a cyclic carbonate bearing a pendant benzyl protected primary alcohol group, and MTCOEt, a hydrophobic cyclic carbonate comonomer. Palladium catalyzed hydrogenolysis of the intermediate protected ROP copolymer deprotects the benzyl protected side chain alcohol groups, forming the linear polymeric P'-ROP initiator PC-1. PC-1 comprises a nucleophilic repeat unit that comprises an aliphatic backbone carbonate group and a side chain alcohol group capable of initiating a ROP.

The above examples illustrate that ring opening polymerizations can be performed in a stepwise manner to construct the ROP initiators and/or the electrophilic polymers starting from a monomeric alcohol and/or a diol. Using the sequential approach, core structure I' of the final cationic polymer (star or graft) is a residue of the P'-ROP initiator, and w' represents the number of ROP initiator groups (e.g., hydroxy groups) of the P'-ROP initiator. Each chain P' is joined to I' by an independent divalent linking group L' comprising a heteroatom residue of a P'-ROP initiator group (e.g., a divalent oxygen residue of a hydroxy initiator group, a trivalent nitrogen of an amine, a divalent sulfur of a thiol). When prepared in this manner, each chain P' comprises a cationic repeat unit derived from the electrophilic cyclic carbonyl monomer.

Although the above-described dendrimer D-1 can effectively initiate a ROP, unimolecular aqueous solutions of cationic star polymers prepared from D-1 hydrolyze readily in water, and therefore are not preferred antimicrobial agents. Consequently, D-1 is not preferred as a P'-ROP initiator for preparing the disclosed cationic star polymers having a dendritic core structure I'.

Other exclusions can apply to the ROP initiators, cationic star polymers, and/or cationic graft polymers. The I'-ROP initiator used to form the linear polymeric P'-ROP initiator can be essentially free of carboxylate esters of phenolic alcohols. Alternatively, the chemical structure of the I'-ROP initiator used to form the linear polymeric P'-ROP initiator can exclude carboxylate esters of phenolic alcohols. The linear polymeric P'-ROP initiator used to form the cationic graft polymer can be essentially free of carboxylate esters of phenolic alcohols. Alternatively, the chemical structure of the linear polymer P'-ROP initiator used to form the cationic graft polymer can exclude carboxylate esters of phenolic alcohols. The chains P' of the cationic polymers can be essentially free of carboxylic esters of phenolic alcohols.

Alternatively, chains P' of the disclosed cationic polymers can exclude carboxylic esters of phenolic alcohols. The cationic polymers can be essentially free of carboxylic esters of phenolic alcohols. Alternatively, the cationic polymers can exclude carboxylic esters of phenolic alcohols.

Counterions that are not covalently bound to the main chemical framework of the cationic polymer can comprise a carboxylic ester of a phenolic alcohol. By "main chemical framework" is meant that portion of the chemical structure of the cationic polymer that contains the majority of linked covalent bonds (as opposed to unbound counterions).

The main chemical framework of the cationic polymer has a net positive charge. The net positive charge can result from cationic groups (i.e., quaternary amine groups) or a mixture of cationic and anionic groups (e.g., carboxylate) that are covalently bound to the main chemical framework of the cationic polymer. The main chemical framework of the cationic polymer can also comprise latent anionic functional groups that remain non-charged until contact with a cell.

Also contemplated are cationic polymers comprising sulfonium groups (i.e., a positive charged sulfur bonded to three carbons), and phosphonium groups (i.e., a phosphorous bonded to four carbons (group). The cationic polymer can comprise a mixture of quaternary amine, sulfonium, and phosphonium functional groups.

Non-limiting exemplary negative charged counterions include chloride, bromide, iodide, acetate, benzoate, benzene sulfonate, and toluene sulfonate. The cationic polymer can comprise a mixture of negative charged counterions.

Polymer chains P' can further comprise a non-charged second repeat unit. Thus, each polymer chain P' can independently comprise a homopolymer, random copolymer, or a block copolymer comprising the cationic repeat unit. The cationic repeat unit and/or the non-charged repeat unit can be stereospecific or non-stereospecific.

Cyclic Carbonyl Monomers.

In the following description of cyclic carbonyl monomers, "first cyclic carbonyl monomer" refers to an electrophilic cyclic carbonyl monomer comprising a monovalent leaving group capable of reacting with a tertiary amine to form a quaternary amine. "Second cyclic carbonyl monomer" refers to a cyclic carbonyl monomer that can be used as a diluent for the first cyclic carbonyl monomer in order to adjust, for example, hydrophobicity and/or hydrophilicity of the cationic polymer. The second cyclic carbonyl monomer forms a repeat unit that is hydrophobic and non-charged in the cationic polymer. The first and/or second cyclic carbonyl monomer can be stereospecific or non-stereospecific.

The first cyclic carbonyl monomer and the second cyclic carbonyl monomer can independently be selected from cyclic esters, cyclic carbonates, cyclic carbamates, cyclic ureas, cyclic thiocarbamates, cyclic thiocarbonates, and cyclic dithiocarbonates, which have the general structures of Table 2.

TABLE 2

| Cyclic Ester | 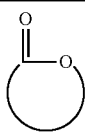 |
|---|---|

TABLE 2-continued

| Cyclic Carbonate | |
|---|---|
| Cyclic Carbamate | |
| Cyclic Urea | |
| Cyclic Thiocarbamate | |
| Cycl Thiocarbonate | |
| Cyclic Dithiocarbonate | |

$Q^1$ in Table 2 is defined under the following formula (2).

More specifically, the first and second cyclic carbonyl monomers can be selected independently from compounds of the general formula (2):

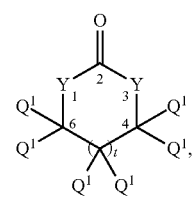

wherein t is an integer from 0 to 6, and when t is 0 carbons labeled 4 and 6 are linked together by a single bond. Each Y is a divalent radical independently selected from the group consisting of

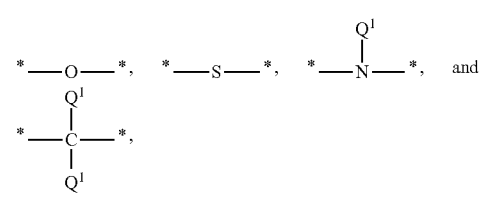

wherein the starred bond indicates a point of attachment. The latter two groups are also expressed herein as *—N(Q$^1$)-* and *—C(Q$^1$)$_2$-*. Each $Q^1$ is a monovalent radical independently selected from the group consisting of hydrogen, halides, alkyl groups comprising 1 to 30 carbons, aryl groups comprising 6 to 30 carbon atoms, and groups having the structure

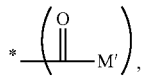

wherein M' is a monovalent radical selected from the group consisting of *—$R^1$, *—$OR^1$, *—$N(H)(R^1)$, *—$N(R^1)_2$, and *—$SR^1$, wherein the starred bond represents the point of attachment, and each $R^1$ is a monovalent radical independently selected from the group consisting of alkyl groups comprising 1 to 30 carbons and aryl groups comprising 6 to 30 carbons. A first cyclic carbonyl monomer of formula (2) comprises one or more $Q^1$ groups comprising a monovalent leaving group capable of reacting with a tertiary amine to form a quaternary amine group. A second cyclic carbonyl monomer of formula (2) comprises no monovalent leaving group that is capable of reacting with a tertiary amine to form a quaternary amine.

Non-limiting examples of monovalent leaving groups include halides in the form of an alkyl halide (e.g., alkyl chloride, alkyl bromide, or alkyl iodide), sulphonate esters (e.g., tosylate or mesylate esters), and epoxides. Each $Q^1$ group can independently be branched or non-branched. Each $Q^1$ group can also independently comprise one or more additional functional groups selected from the group consisting of ketones, aldehydes, alkenes, alkynes, cycloaliphatic rings comprising 3 to 10 carbons, heterocylic rings comprising 2 to 10 carbons, ethers, amides, esters, and combinations of the foregoing functional groups. A heterocyclic ring can comprise oxygen, sulfur and/or nitrogen. Two or more $Q^1$ groups can together form a ring.

The ring opened polymer chain formed with a cyclic carbonyl monomer of formula (2) has a repeat unit having the general formula (3):

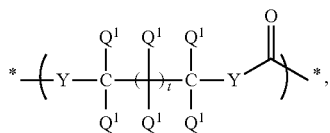

(3)

wherein Y, t, and $Q^1$ are defined as above. In an embodiment, Y is oxygen.

A repeat unit of a ring opened polymer formed with a cyclic carbonyl monomer of formula (2) can have a backbone functional group selected from the group consisting of esters, carbonates, ureas, carbamates, thiocarbamates, dithiocarbonates, and combinations thereof, as shown in Table 3.

TABLE 3

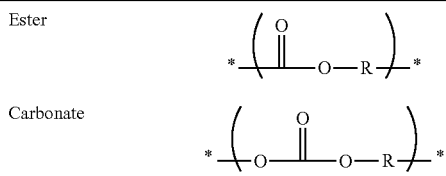

TABLE 3-continued

| Urea | |
|---|---|
| Carbamate | |
| Thiocarbamate | |
| Thiocarbonate | |
| Dithiocarbonate | | wherein $Q^1$ of Table 3 is defined under formula (2), and R of Table 3 is an aliphatic group

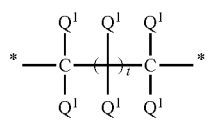

of formula (3) above. Subscript t is defined above under formula (2).

The first and second cyclic carbonyl monomers can be selected independently from compounds of the general formula (4):

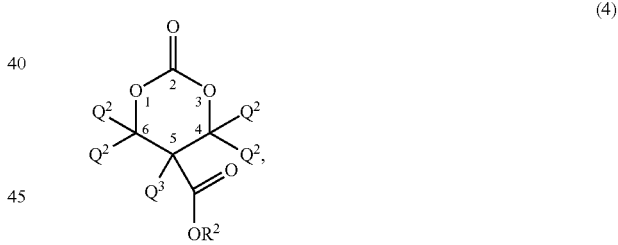

(4)

wherein $Q^2$ is a monovalent radical independently selected from the group consisting of hydrogen, halides, alkyl groups comprising 1 to 30 carbons, aryl groups comprising 6 to 30 carbon atoms, and groups having the structure

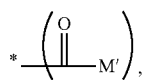

wherein M' is a monovalent radical selected from the group consisting of *—$R^1$, *—$OR^1$, *—$N(H)(R^1)$, *—$N(R^1)_2$, and *—$SR^1$, wherein each $R^1$ is a monovalent radical independently selected from the group consisting of alkyl groups comprising 1 to 30 carbons and aryl groups comprising 6 to 30 carbons. $R^2$ is a monovalent radical independently selected from the group consisting of alkyl groups comprising 1 to 30 carbons and aryl groups comprising 6 to 30 carbons, and $Q^3$ is a monovalent radical selected from the group consisting of hydrogen, alkyl groups having 1 to 30 carbons, and aryl groups having 6 to 30 carbons. In an embodiment, each $Q^2$ is hydrogen, $Q^3$ is a methyl or ethyl group, and $R^2$ is an alkyl group comprising 1 to 30 carbons. A first cyclic carbonyl monomer of formula (4) comprises an $R^2$ group comprising a monovalent leaving group capable of reacting with a tertiary amine to form a quaternary amine. A second cyclic carbonyl monomer of formula (4) comprises no monovalent leaving group that is capable of reacting with a tertiary amine to form a quaternary amine.

The ring opened polymer chain formed with a cyclic carbonyl monomer of formula (4) has a backbone carbonate repeat unit having the general formula (5):

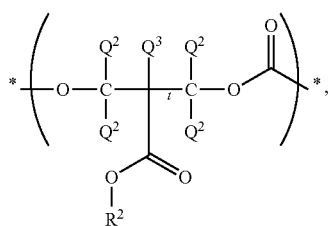

(5)

wherein $Q^2$, $Q^3$, and $R^2$ are defined as above.

The first and second cyclic carbonyl monomers can be selected from cyclic esters of the general formula (6):

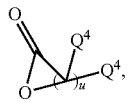

(6)

wherein u is an integer from 1 to 8, each $Q^4$ is a monovalent radical independently selected from the group consisting of hydrogen, halides, alkyl groups comprising 1 to 30 carbons, aryl groups comprising 6 to 30 carbon atoms, and groups having the structure

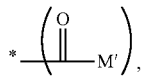

where M' is a monovalent radical selected from the group consisting of *—$R^1$, *—$OR^1$, *—$N(H)(R^1)$, *—$N(R^1)_2$, and *—$SR^1$, wherein each $R^1$ is a monovalent radical independently selected from the group consisting of alkyl groups comprising 1 to 30 carbons and aryl groups comprising 6 to 30 carbons. The lactone ring can optionally comprise a carbon-carbon double bond; that is, optionally, a

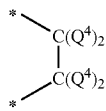

group of formula (5) can independently represent a

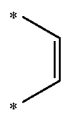

group. The lactone ring can also comprise a heteroatom such as oxygen, nitrogen, sulfur, or a combination thereof; that is, optionally a

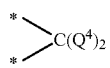

group of formula (6) can independently represent a *—O—*, *—S—*, *—N(H)—*, or an *—$N(R^1)$—* group, wherein $R^1$ has the same definition as above. A first cyclic carbonyl monomer of formula (6) comprises a $Q^4$ group comprising a monovalent leaving group capable of reacting with a tertiary amine to form a quaternary amine. A second cyclic carbonyl monomer of formula (6) comprises no monovalent leaving group capable of reacting with a tertiary amine to form a moiety comprising a quaternary amine.

The ring opened polymer chain formed with a cyclic carbonyl monomer of formula (6) has a backbone ester repeat unit having the general formula (7):

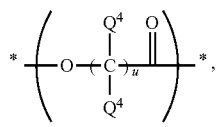

(7)

wherein $Q^4$ and u are defined as above.

The first and/or second cyclic carbonyl monomers can be selected from a dioxane dicarbonyl monomers of the general formula (8):

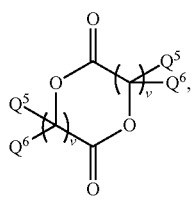

(8)

wherein each $Q^5$ is a monovalent radical independently selected from the group consisting of hydrogen, halides, carboxy groups, alkyl groups comprising 1 to 30 carbons, aryl groups comprising 6 to 30 carbon atoms, and groups having the structure

where each v is independently an integer from 1 to 6, M' is a monovalent radical selected from the group consisting of *—$R^1$, *—$OR^1$, *—$N(H)(R^1)$, *—$N(R^1)_2$, and *—$SR^1$, wherein each $R^1$ is a monovalent radical independently selected from the group consisting of alkyl groups comprising 1 to 30 carbons and aryl groups comprising 6 to 30 carbons, each $Q^6$ is a monovalent group independently selected from the group consisting of hydrogen, alkyl groups having 1 to 30 carbons, and aryl groups having 6 to 30 carbons. A first cyclic carbonyl monomer of formula (8) comprises a $Q^5$ and/or a $Q^6$ group comprising a monovalent leaving group capable of reacting with a tertiary amine to form a quaternary amine. A second cyclic carbonyl monomer of formula (8) comprises no monovalent leaving group capable of reacting with a tertiary amine to form a moiety comprising a quaternary amine. In an embodiment, the second cyclic carbonyl monomer comprises a compound of formula (8) wherein each v is 1, each $Q^5$ is hydrogen, and each $Q^6$ is an alkyl group comprising 1 to 6 carbons. In an embodiment, the second cyclic carbonyl monomer is D-lactide or L-lactide.

The ring opened polymer chain formed with a cyclic carbonyl monomer of formula (8) has a backbone ester repeat unit having the general formula (9):

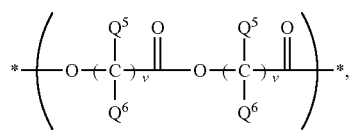

(9)

wherein $Q^5$, $Q^6$, and v are defined as above.

Examples of cyclic carbonate monomers formulas (2) and (4) having a monovalent leaving group in the form of an alkyl halide include the cyclic carbonate monomers of Table 4.

TABLE 4

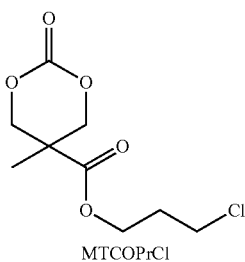

MTCOPrCl

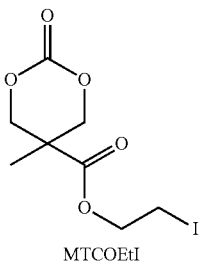

MTCOEtI

TABLE 4-continued

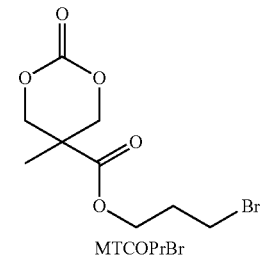

MTCOPrBr

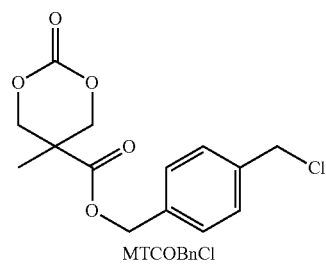

MTCOBnCl

Additional examples of cyclic carbonate monomers of formula (2) and (4) include the compounds of Table 5. These can be used, for example, as diluent comonomers for the ring-opening polymerization or as intermediates to form other derivatives of cyclic carbonate monomers.

TABLE 5

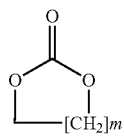

m = 1: Trimethylene carbonate (TMC)
m = 2: Tetramethylene carbonate (TEMC)
m = 3: Pentamethylene carbonate (PMC)

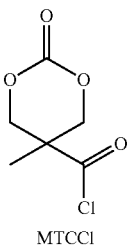

MTCCl

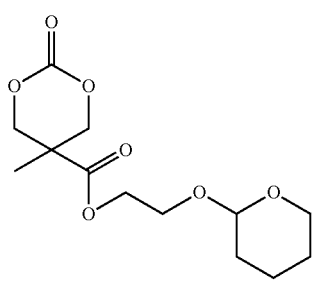 [SMILES: CC1(C(=O)OCCOC2CCCCO2)COC(=O)OC1]

TABLE 5-continued
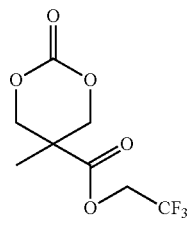
MTCTFE
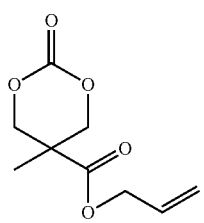
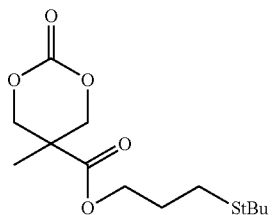
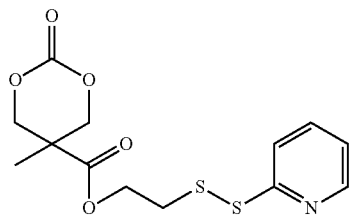 [SMILES: CC1(C(=O)OCCSSc2ccccn2)COC(=O)OC1]
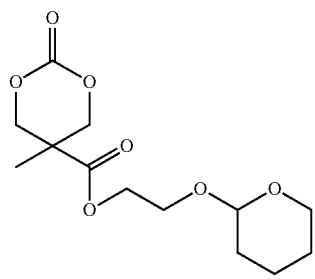 [SMILES: CC1(C(=O)OCCOC2CCCCO2)COC(=O)OC1]
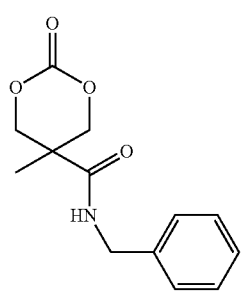 [SMILES: CC1(C(=O)NCc2ccccc2)COC(=O)OC1]
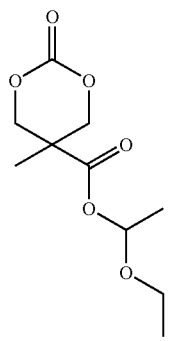
MTCOEE
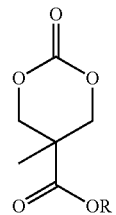
R = hydrogen (MTCOH)
R = methyl (MTCOMe)
R = t-butyl (MTCO<sup>t</sup>Bu)
R = ethyl (MTCOEt)
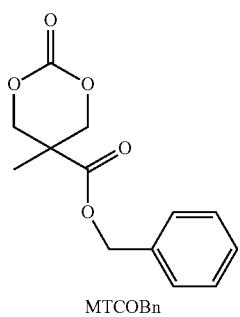
MTCOBn
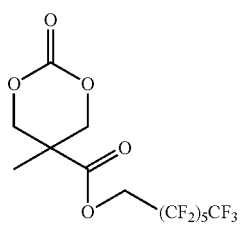
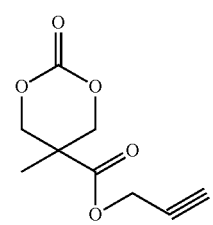

TABLE 5-continued

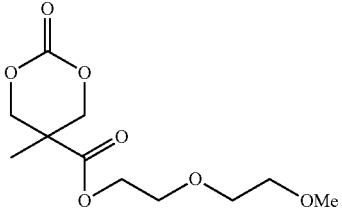 [SMILES: COCCOCCOC(=O)C1(C)COC(=O)OC1]

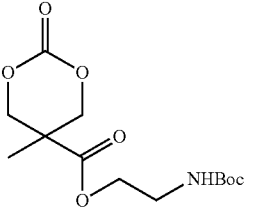 [SMILES: CC(C)(C)OC(=O)NCCOC(=O)C1(C)COC(=O)OC1]

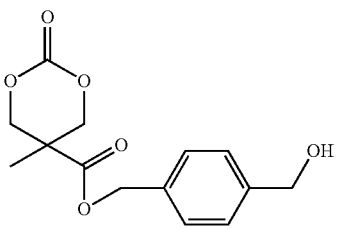 [SMILES: CC1(C(=O)OCc2ccc(CO)cc2)COC(=O)OC1]

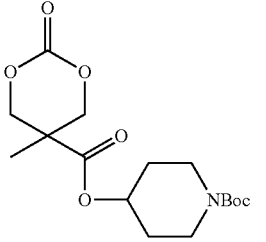 [SMILES: CC(C)(C)OC(=O)N1CCC(OC(=O)C2(C)COC(=O)OC2)CC1]

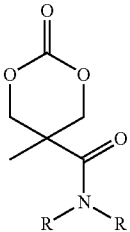

R = methyl
R = iso-propyl

Examples of cyclic carbonyl monomers of formula (6) include the compounds of Table 6, and stereospecific versions thereof, where feasible, comprising one or more stereospecific asymmetric ring carbons.

TABLE 6

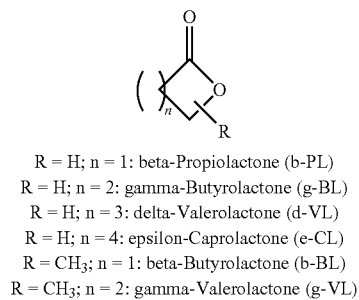

R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = CH$_3$; n = 1: beta-Butyrolactone (b-BL)
R = CH$_3$; n = 2: gamma-Valerolactone (g-VL)

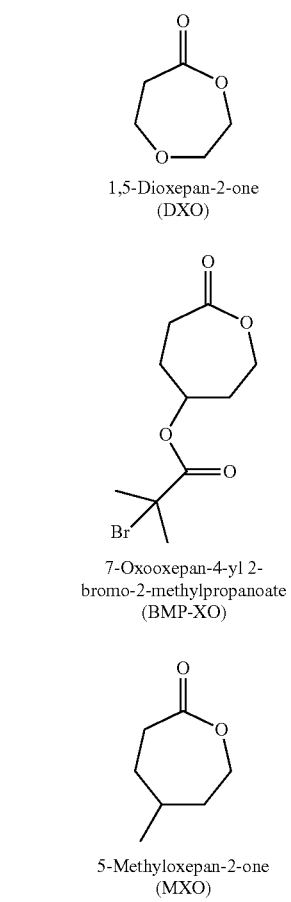

1,5-Dioxepan-2-one
(DXO)

7-Oxooxepan-4-yl 2-bromo-2-methylpropanoate
(BMP-XO)

5-Methyloxepan-2-one
(MXO)

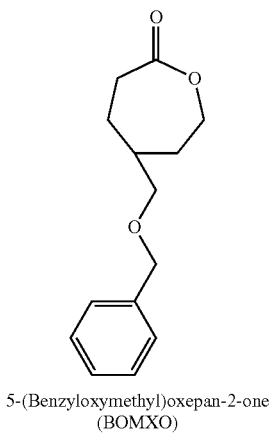 [SMILES: O=C1CCC(COCc2ccccc2)CCO1]

5-(Benzyloxymethyl)oxepan-2-one
(BOMXO)

TABLE 6-continued

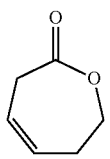

(Z)-6,7-Dihydrooxepin-2(3H)-one
(DHXO)

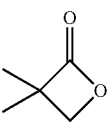

Pivalolactone
(PVL)

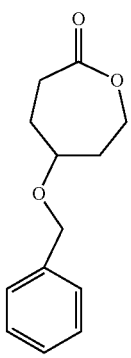

5-(Benzyloxy)oxepan-2-one
(BXO)

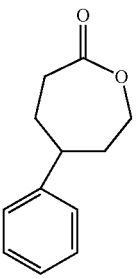

5-Phenyloxepan-2-one
(PXO)

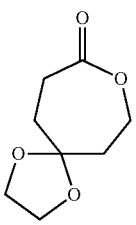

1,4,8-Trioxa(4,6)spiro-9-undecane
(TOSUO)

TABLE 6-continued

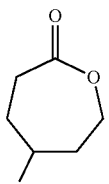

7-Oxooxepan-4-yl 3-hydroxy-2-(hydroxymethyl)-2-methylpropanoate
(OX-BHMP)

Examples of cyclic carbonyl monomers of formula (8) include the compounds of Table 7.

TABLE 7

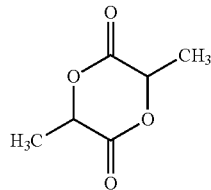

D-Lactide (DLA),
L-Lactide (LLA), or
racemic Lactide, 1:1 D:L forms (DLLA)

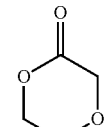

Glycolide (GLY)

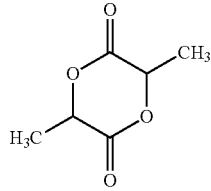

meso-Lactide (MLA)
(two opposite centers of asymmetry, R and S)

The above monomers can be purified by recrystallization from a solvent such as ethyl acetate or by other known methods of purification, with particular attention being paid to removing as much water as possible from the monomer. The monomer moisture content can be from 1 to 10,000 ppm, 1 to 1,000 ppm, 1 to 500 ppm, and most specifically 1 to 100 ppm, by weight of the monomer.

I'-ROP Initiators.

The I'-ROP initiator used to prepare the P'-ROP initiator can comprise one or two nucleophilic initiator groups selected from the group consisting of alcohols, primary amines, secondary amines, thiols, and combinations thereof. The I'-ROP initiator can be a monomer, oligomer, or a polymer. The I'-ROP initiator can include other functional groups, including protected nucleophilic groups that include protected thiols, protected amines, and/or protected alcohols. Exemplary monomeric mono-nucleophilic I'-ROP initiators include mono-alcohols, such as methanol, ethanol, propanol, butanol, pentanol, amyl alcohol, capryl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, nonadecyl alcohol and other aliphatic saturated alcohols, cyclopentanol, cyclohexanol, cycloheptanol, cyclooctanol and other aliphatic cyclic alcohols; benzyl alcohol, substituted benzyl alcohols, and the like. Exemplary polymeric mono-nucleophilic initiators include mono-endcapped poly(ethylene glycols), and mono-endcapped poly(propylene glycols). Exemplary monomeric and oligomeric dinucleophilic initiators include benzenedimethanol, propylene glycol, ethylene glycol, diethylene glycol, and triethylene glycol.

Based on the exclusions mentioned above, phenol, substituted phenols, hydroquinone, resorcinol, and other phenolic compounds are not preferred I'-ROP initiators.

Other dinucleophilic initiators include monomeric diols such as 1,3-propanediol, 1,4-butanediol, 1,5-pentanediol, 1,6-hexanediol, and the like. As mentioned above, an even more specific dinucleophilic initiator is BnMPA, a precursor used in the preparation of cyclic carbonate monomers:

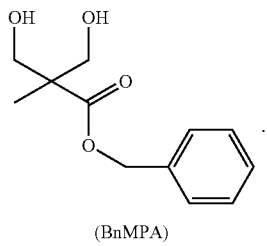 [SMILES: CC(CO)(CO)C(=O)OCc1ccccc1]

(BnMPA)

A polymeric dinucleophilic initiator can be a polyether diol, more specifically a poly(alkylene glycol) of the general formula (9):

$$HO-[CH_2(CHR^1)_xCHR^1O]_n-H \qquad (9),$$

wherein x is 0 or 1, n is an integer from 2 to 10000, each $R^1$ is a monovalent radical independently selected from the group consisting of hydrogen and methyl. Thus, the ether repeat unit can comprise 2 or 3 backbone carbons between each backbone oxygen. As non-limiting examples, the poly(alkylene glycol) can be a poly(ethylene glycol) (PEG) having the structure $HO-[CH_2CH_2O]_n-H$, a poly(propylene glycol) (PPG) having the structure $HO-[CH_2C(H)(CH_3)O]_n-H$, or a mixture thereof.

The dinucleophilic polyether initiator can comprise nucleophilic chain end groups independently selected from the group consisting alcohols, primary amines, secondary amines, and thiols. Non-limiting examples include:

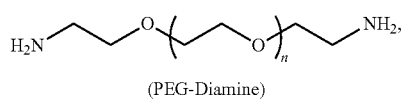

(PEG-Diamine)

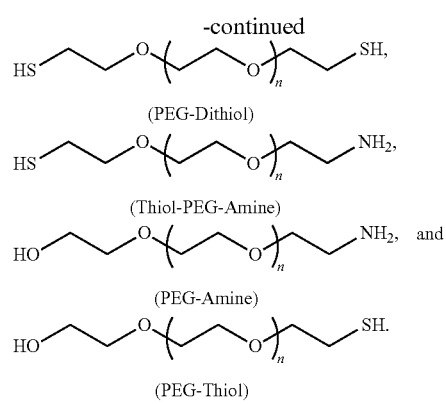

(PEG-Dithiol)

(Thiol-PEG-Amine)

(PEG-Amine)

(PEG-Thiol)

One or both end units of the dinucleophilic polyether initiator can be derivatized with substituents having a nucleophilic initiator group for ring opening polymerization, as in poly(alkylene oxide)s of general formula (10):

$$Z'-[CH_2(CHR^1)_xCHR^1O]_n-Z'' \qquad (10)$$

wherein x is 0 or 1, n is an integer from 2 to 10000, each $R^1$ is a monovalent radical independently selected from the group consisting of hydrogen and methyl, Z' is a monovalent radical selected from the group consisting of *—OH, *—NH$_2$, secondary amines, *—SH, and $C_1$-$C_{50}$ groups comprising a nucleophilic initiator group for ring opening polymerization, Z'' is a monovalent radical selected from the group consisting of hydrogen and $C_1$-$C_{50}$ groups comprising a nucleophilic initiator group for ring opening polymerization. At least one of Z' and Z'' comprises a $C_1$-$C_{50}$ group comprising a nucleophilic initiator group for ring opening polymerization, the nucleophilic initiator group selected from the group consisting of alcohols, primary amines, secondary amines, and thiols. In an embodiment, Z' and/or Z'' comprises a biologically active moiety. In an embodiment x is 0, and each $R^1$ is hydrogen.

The number average molecular weight of the dinucleophilic polyether initiator can be from 100 to 100,000, more specifically 100 to 10000, and even more specifically, 100 to 5000.

Cationic Repeat Units.

In a more specific embodiment, the cationic polymer comprises a cationic repeat unit of the general formula (11):

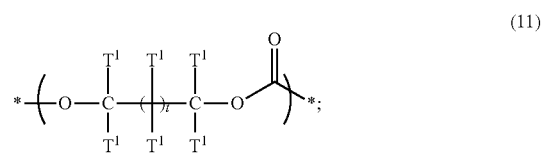

wherein i) t is an integer from 0 to 6, and ii) each $T^1$ is a monovalent radical independently selected from the group consisting of hydrogen, and groups comprising 1 to 30 carbons, and iii) at least one $T^1$ group comprises a quaternary amine group. The quaternary amine group comprises a divalent methylene group directly bonded to i) a positive charged nitrogen and ii) an aromatic ring.

In an even more specific example, the cationic polymer comprises a cationic repeat of the general formula (12):

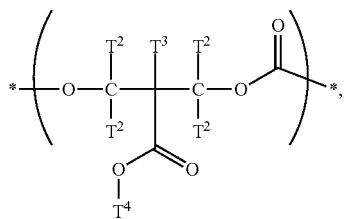

(12)

wherein each $T^2$ and $T^3$ are independent monovalent radicals selected from the group consisting of hydrogen, and groups comprising 1 to 30 carbons, and $T^4$ comprises a quaternary amine group. The quaternary amine group comprises a divalent methylene group directly covalently linked to i) a positive charged nitrogen and ii) an aromatic ring. In an embodiment, each $T^2$ is hydrogen, and $T^3$ is methyl or ethyl.
Endcap agents.

An endcap agent can prevent further chain growth and stabilize the reactive end groups, minimizing unwanted side reactions (e.g., chain scission). Endcap agents include, for example, materials for converting terminal hydroxyl groups to esters, such as carboxylic acid anhydrides, carboxylic acid chlorides, or reactive esters (e.g., p-nitrophenyl esters). In an embodiment, the endcap agent is acetic anhydride, which converts reactive hydroxy end groups to acetate ester groups. The endcap group can also be a biologically active moiety.

Quaternization Reaction.

The electrophilic polymer comprises an electrophilic repeat unit derived from the first cyclic carbonyl monomer having a side chain comprising a reactive monovalent leaving group capable of reacting with a tertiary amine to form a quaternary amine. The electrophilic polymer can be treated with a tertiary amine to form the cationic polymer. The quaternization reaction can be accompanied by minimal, if any, crosslinking of the cationic polymer. The quaternary nitrogen can be covalently linked to the side chain. Alternatively, the quaternary nitrogen can be directly covalently linked to a backbone carbon.

No limitation is placed on the structure of the tertiary amine, providing the resulting quaternary amine group comprises a divalent methylene group directly covalently linked to i) a positive charged nitrogen and ii) an aromatic ring.

The tertiary amine reacts with more than 0% of the monovalent leaving groups of the electrophilic polymer to form a quaternary amine, preferably 10% or more, 20% or more, 30% or more, 40% or more, 50% or more, 60% or more, 70% or more, or more particularly 80% or more of the monovalent leaving groups of the electrophilic polymer.

The tertiary amine can comprise a single nitrogen such as a trialkylamine, including but not limited to trimethylamine, triethylamine, tripropylamine, dimethylbenzylamine, methyldibenzylamine, and the like. The tertiary amine can further comprise additional functional groups, in particular a carboxylic acid group, for example 3-(N,N-dimethylamino) propionic acid. In such instances, the cationic polymer will comprise cationic repeat units comprising a side chain comprising a quaternary amine group and a carboxylic acid group.

The tertiary amine can also comprise isotopically enriched versions of the tertiary amine, such as trimethylamine-$^{14}$C, trimethylamine-$^{15}$N, trimethylamine-$^{15}$N, trimethyl-$^{13}$C3-amine, trimethyl-$d_9$-amine, and trimethyl-$d_9$-amine-$^{15}$N. The tertiary amine can also comprise a radioactive moiety suitable for targeting a specific cell type, such as a cancer cell. The radioactive moiety can comprise a heavy metal radioactive isotope.

In an embodiment, the tertiary amine is a bis-tertiary amine, and the cationic polymer comprises a side chain comprising a quaternary amine group and a tertiary amine group. The side chain tertiary amine groups provide buffering capacity to facilitate release of the biologically active substance from a loaded complex of the cationic polymer and a gene and/or a drug. Bis-tertiary amines have the general formula (13):

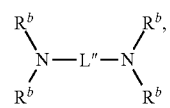

(13)

wherein L" is a divalent linking group comprising 2 to 30 carbons, and each monovalent $R^b$ group is independently selected from alkyl groups comprising 1 to 30 carbons or aryl groups comprising 6 to 30 carbons. Each $R^b$ group can independently be branched or non-branched. Each $R^b$ group can independently comprise additional functional groups such as a ketone group, aldehyde group, hydroxyl group, alkene group, alkyne group, cycloaliphatic ring comprising 3 to 10 carbons, heterocylic ring comprising 2 to 10 carbons, ether group, amide group, ester group, and combinations of the foregoing additional functional groups. The heterocyclic ring can comprise oxygen, sulfur and/or nitrogen. Two or more $R^b$ groups can also together form a ring. Representative L" groups include *—$(CH_2)_{z'}$—* where z' is an integer from 2 to 30, *—$(CH_2CH_2O)_{z''}CH_2CH_2$—* where z" is an integer from 1 to 10, *—$CH_2CH_2SCH_2CH_2$—*, *—$CH_2CH_2SSCH_2CH_2$—*, *—$CH_2CH_2SOCH_2CH_2$—*, and *—$CH_2CH_2SO_2CH_2CH_2$—*. L" can further comprise a monovalent or divalent cycloaliphatic ring comprising 3 to 20 carbons, a monovalent or divalent aromatic ring comprising 6 to 20 carbons, a ketone group, aldehyde group, hydroxyl group, alkene group, alkyne group, a heterocylic ring comprising 2 to 10 carbons, ether group, amide group, ester group, and combinations of the foregoing functional groups. The heterocyclic ring can comprise oxygen, sulfur and/or nitrogen. The bis-tertiary amine can also comprise isotopically enriched forms of the bis-tertiary amine, such as deuterium, carbon-13, and/or nitrogen-15 enriched forms thereof.

More specific bis-tertiary amines include N,N,N',N'-tetramethyl-1,2-ethanediamine (TMEDA), N,N,N',N'-tetramethyl-1,3-propanediamine (TMPDA), N,N,N',N'-tetramethyl-1,4-butanediamine (TMBDA), N,N,N',N'-tetraethyl-1,2-ethanediamine (TEEDA), N,N,N',N'-tetraethyl-1,3propanediamine (TEPDA), 1,4-bis(dimethylamino)cyclohexane, 1,4-bis(dimethylaminobenzene), N,N,N',N'-tetraethyl-1,4-butanediamine (TEBDA), 4-dimethylaminopyridine (DMAP), 4,4-dipyridyl-1,4-diazabicyclo[2.2.2]octane (DABCO), 4-pyrrolidinopyridine, 1-methylbenzimidazole, and combinations thereof. In an embodiment, the bis-tertiary amine is TMEDA.

The electrophilic polymer can be treated with the tertiary amine in a suitable organic solvent (e.g., acetonitrile, dimethylsulfoxide (DMSO), dimethylformamide (DMF), and combinations thereof) to form the cationic polymer. The reaction is preferably conducted under anhydrous conditions, at ambient or elevated temperature using excess tertiary amine relative to the monovalent leaving group. In general, the tertiary amine is used in an amount of from 2 to 30 moles per mole of monovalent leaving group in the electrophilic polymer, more particularly 3 to 20 moles per mole of monovalent leaving group in the electrophilic polymer. The positive charged quaternary amine forms a salt with the displaced leaving group, which becomes a negatively charged counterion. Alternatively, the negatively charged counterion can be ion exchanged with another more suitable negative charged counterion using known methods.

The cationic polymer can be isolated by removing excess solvent and amine by vacuum, or by precipitating the cationic polymer in an organic solvent such as tetrahydrofuran, followed by filtration and drying in vacuo. More than 0% of the repeat units derived from the first cyclic carbonyl monomer comprise a side chain moiety comprising a quaternary amine group. When the electrophilic polymer is treated with a bis-tertiary amine, more than 0% of the repeat units derived from the first cyclic carbonyl monomer comprise a side chain moiety comprising a quaternary amine group and a tertiary amine group. When the electrophilic polymer is treated with a tertiary amine comprising a carboxy group or a latent carboxylic acid group, more than 0% of the first repeat units derived from the first cyclic carbonyl monomer comprise the side chain moiety comprising the quaternary amine and a carboxylic acid or a latent carboxylic acid group. The quaternary amine group is present in the cationic polymer in an amount greater than 0% of the side chain monovalent leaving groups derived from the first cyclic carbonyl monomer. More particularly, the quaternary amine group is present in the cationic polymer in an amount of 10% to 100%, 20% to 100%, 30% to 100%, 40% to 100%, 50% to 100%, 60% to 100%, 70% to 100%, or 80% to 100% of the side chain monovalent leaving groups derived from the first cyclic carbonyl monomer.

When the electrophilic polymer is treated with a bis-tertiary amine, the tertiary amine group can be present in the cationic polymer in an amount greater than 0% of the repeat units comprising a monovalent leaving groups of the electrophilic polymer, more particularly 10% to 100%, 20% to 100%, 30% to 100%, 40% to 100%, 50% to 100%, 60% to 100%, 70% to 100%, or 80% to 100% of the repeat units comprising a monovalent leaving groups of the electrophilic polymer.

Ring Opening Polymerizations (ROP).

The following description of methods, conditions and materials for ring opening polymerizations is applicable to the preparation of the P'-ROP initiator and cationic polymer.

The ring-opening polymerization can be performed at a temperature that is about ambient temperature or higher, 15° C. to 200° C., and more specifically 20° C. to 200° C. When the reaction is conducted in bulk, the polymerization is performed at a temperature of 50° C. or higher, and more particularly 100° C. to 200° C. Reaction times vary with solvent, temperature, agitation rate, pressure, and equipment, but in general the polymerizations are complete within 1 to 100 hours.

The ROP reaction is preferably performed with a solvent. Optional solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. When a solvent is present, a suitable monomer concentration is about 0.1 to 5 moles per liter, and more particularly about 0.2 to 4 moles per liter.

The ROP polymerizations are conducted under an inert dry atmosphere, such as nitrogen or argon, and at a pressure of from 100 to 500 MPa (1 to 5 atm), more typically at a pressure of 100 to 200 MPa (1 to 2 atm). At the completion of the reaction, the solvent can be removed using reduced pressure.

Less preferred catalysts for ROP polymerizations include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetra-ethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; heteropolyacids such as phosphotungstic acid, phosphomolybdic acid, silicotungstic acid and alkali metal salt thereof; zirconium compounds such as zirconium acid chloride, zirconium octanoate, zirconium stearate, and zirconium nitrate.

The catalyst is preferably an organocatalyst whose chemical formula contains none of the above-described restricted metals. Examples of organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines.

A more specific organocatalyst is N-bis(3,5-trifluoromethyl)phenyl-N'-cyclohexyl-thiourea (TU):

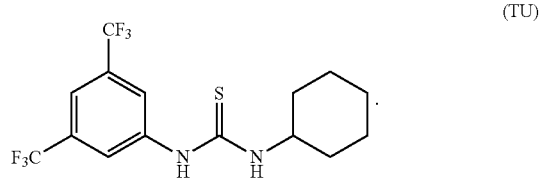 [SMILES: FC(F)(F)c1cc(NC(=S)NC2CCCCC2)cc(C(F)(F)F)c1]

(TU)

Other ROP organocatalysts comprise at least one 1,1,1,3,3,3-hexafluoropropan-2-ol-2-yl (HFP) group. Singly-donating hydrogen bond catalysts have the formula (14):

$$R^2-C(CF_3)_2OH \qquad (14),$$

wherein $R^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalklyl group, aryl group, substituted aryl group, or a combination thereof. Exemplary singly-donating hydrogen bonding catalysts are listed in Table 8.

TABLE 8

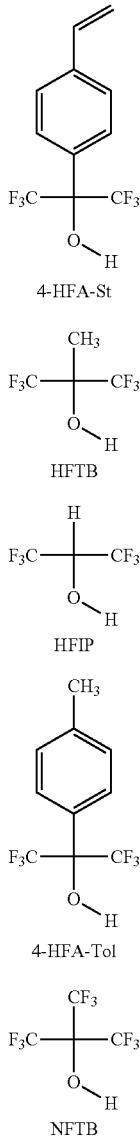

Doubly-donating hydrogen bonding catalysts have two HFP groups, represented by the general formula (15):

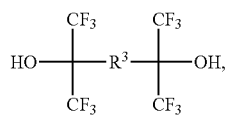

wherein $R^3$ is a divalent radical bridging group containing from 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, and a combination thereof. Representative double hydrogen bonding catalysts of formula (15) include those listed in Table 9. In a specific embodiment, $R^2$ is an arylene or substituted arylene group, and the HFP groups occupy positions meta to each other on the aromatic ring.

TABLE 9

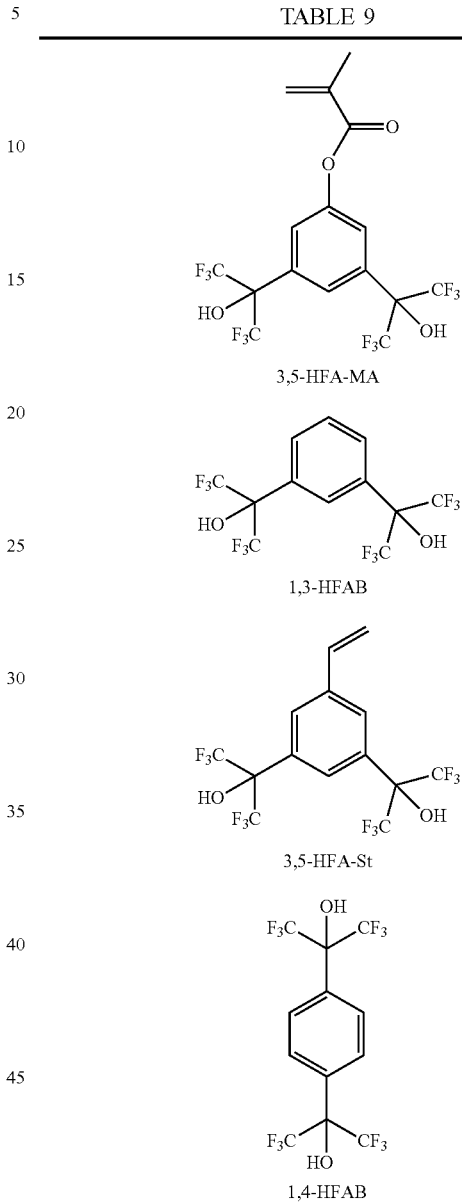

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one organocatalyst and, when appropriate, several organocatalysts together. The ROP catalyst is added in a proportion of 1/20 to 1/40,000 moles relative to the cyclic carbonyl monomers, and preferably in a proportion of 1/1,000 to 1/20,000 moles relative to the cyclic carbonyl monomers.

ROP Accelerators.

The ROP polymerization can be conducted in the presence of an optional accelerator, in particular a nitrogen base. Exemplary nitrogen base accelerators are listed below and include pyridine (Py), N,N-dimethylaminocyclohexane (Me$_2$NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-1-propylphenyl(imidazol-2-ylidene (Im-3), 1,3-bis(1-adamantyl)imidazol-2-ylidene (Im-4), 1,3-di-1-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-1-propylphenyl)-4,5-dihydroimidazol-2-ylidene, 1,3-bis(2,6-di-1-propylphenyl)-4,5-dihydroimidazol-2-ylidene (Im-8) or a combination thereof, shown in Table 10.

TABLE 10

Pyridine
(Py)

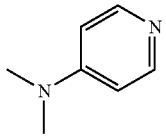

4-N,N-Dimethylaminopyridine
(DMAP)

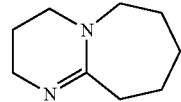

1,8-Diazabicyclo[5.4.0]undec-7-ene
(DBU)

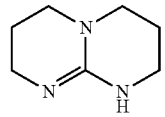

1,5,7-Triazabicyclo[4.4.0]dec-5-ene
(TBD)

TABLE 10-continued

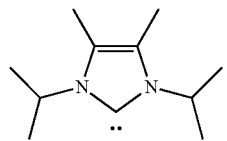

1,3-Bis(2-propyl)-4,5-
dimethylimidazol-2-ylidene
(Im-1)

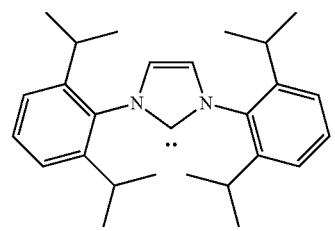

1,3-Bis(2,6-di-i-propylphenyl(imidazol-2-ylidene
(Im-3)

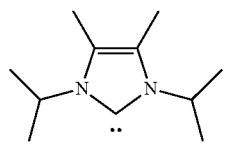

1,3-Di-i-propylimidazol-2-ylidene
(Im-5)

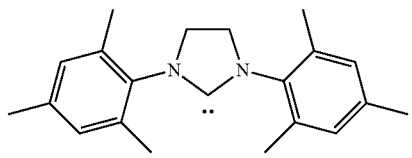

1,3-Bis(2,4,6-trimethylphenyl)-4,5-
dihydroimidazol-2-ylidene
(Im-7)

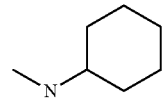

N,N-Dimethylaminocyclohexane
(Me$_2$NCy)

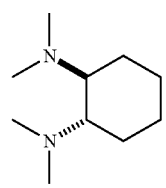

trans 1,2-Bis(dimethylamino)cyclohexane
(TMCHD)

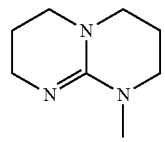

7-Methyl-1,5,7-
triazabicyclo[4.4.0]dec-5-ene
(MTBD)

TABLE 10-continued

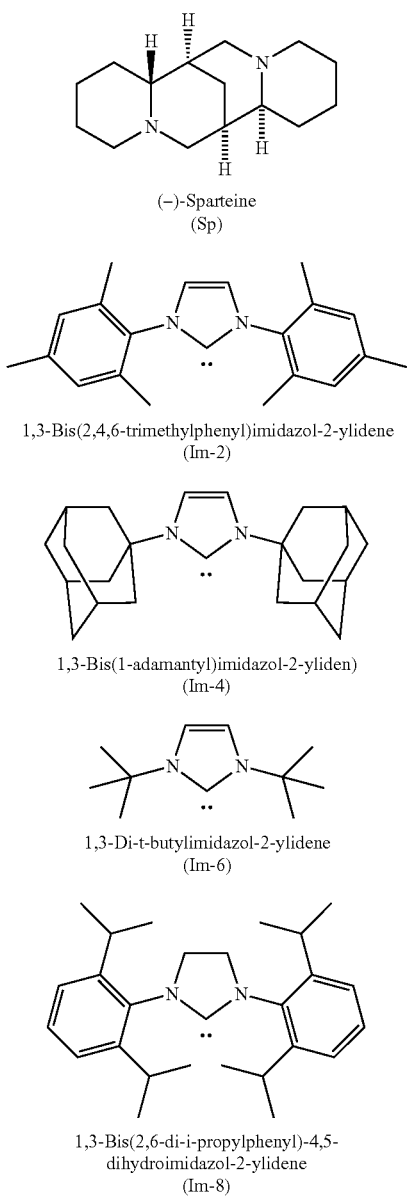

In an embodiment, the accelerator has two or three nitrogens, each capable of participating as a Lewis base, as for example in the structure (−)-sparteine. Stronger bases generally improve the polymerization rate.

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

The amount of initiator is calculated based on the equivalent molecular weight per nucleophilic initiator group in the ROP initiator. The initiator groups are preferably present in an amount of 0.001 to 10.0 mol %, 0.1 to 2.5 mol %, 0.1 to 1.0 mol %, and 0.2 to 0.5 mol %, based on total moles of cyclic carbonyl monomer used in the polymerization. For example, if the molecular weight of the initiator is 100 g/mole and the initiator has 2 hydroxyl groups, the equivalent molecular weight per hydroxyl group is 50 g/mole. If the polymerization calls for 5 mol % hydroxyl groups per mole of monomer, the amount of initiator is 0.05×50=2.5 g per mole of monomer.

In a specific embodiment, the catalyst is present in an amount of about 0.2 to 20 mol %, the nitrogen base accelerator is present in an amount of 0.1 to 5.0 mol %, and the nucleophilic initiator groups of the initiator are present in an amount of 0.1 to 5.0 mol % based on the equivalent molecular weight per nucleophilic initiator group of the initiator.

The catalysts can be removed by selective precipitation or in the case of the solid supported catalysts, simply by filtration. The product of the ROP can comprise residual catalyst in an amount greater than 0 wt. % (weight percent), based on total weight of the block copolymer and the residual catalyst. The amount of residual catalyst can also be less than 20 wt. %, less than 15 wt. %, less than 10 wt. %, less than 5 wt. %, less than 1 wt. %, or most specifically less than 0.5 wt. % based on the total weight of the ROP polymer and the residual catalyst.

Average Molecular Weight.

The cationic polymer and/or the electrophilic polymer preferably has a number average molecular weight (Mn) as determined by size exclusion chromatography of at least 1500 g/mol, more specifically 1500 g/mol to 1,000,000 g/mol, 4000 g/mol to 150000 g/mol, or 4000 g/mol to 50000 g/mol. In an embodiment, the cationic polymer and/or the electrophilic polymer has a number average molecular weight of 10,000 to 20,000 g/mole. The cationic polymer and/or the electrophilic polymer also preferably has a narrow polydispersity index (PDI), generally from 1.01 to 2.0, more particularly 1.01 to 1.30, and even more particularly 1.01 to 1.25.

A cyclic carbonyl monomer comprising a pendant quaternary amine group can be used to prepare the cationic polymer. However, these monomers are more difficult to prepare, are less stable, and the corresponding polymers tend to be more polydisperse. Therefore, the quaternization reaction is preferably performed after the ring-opening polymerization(s).

In aqueous solution, the cationic polymers form unimolecular nanoparticles having an average particle size of 10 nm to 500 nm, 10 nm to 250 nm, and more particularly 50 nm to 200 nm as measured by dynamic light scattering. For the foregoing particle sizes, the aqueous solution preferably has a pH of 4.5 to 8.0, 5.0 to 7.0, or 6.0 to 7.0.

INDUSTRIAL APPLICABILITY

Compositions comprising the cationic polymers have strong antimicrobial properties against Gram-negative and/or Gram-positive microbes, and have low cytotoxicity. Furthermore, the cationic polymers can be substantially or wholly biodegradable, making the compositions attractive for prevention and treatment of infections caused by drug-resistant microbes such as methicillin-resistant *Staphylococcus aureus* (MRSA). Uses include disinfectant washes for hands, skin, hair, bone, ear, eye, nose, throat, internal tissue, wounds, and teeth (e.g., as a mouthwash).

A method comprises contacting a microbe with the antimicrobial composition, thereby killing the microbe.

The cationic polymer can be used as a drug. The drug can be administered as a powder, a pill, or a liquid solution. The drug can be administered orally or by way of other body cavities, by injection, intravenously, and/or topically. An injectable composition comprises an aqueous mixture of the disclosed cationic polymers. A method of treating a cell comprises contacting the cell with a composition comprising i) the disclosed cationic polymer and ii) a gene and/or a drug.

The cationic polymers can be applied to human and/or other animal tissues, mammalian and/or non-mammalian tissues. The general term "animal tissue" includes wound tissue, burn tissue, skin, internal organ tissue, blood, bones, cartilage, teeth, hair, eyes, nasal surfaces, oral surfaces, other body cavity surfaces, and any cell membrane surfaces.

The cationic polymers are also attractive as disinfecting agents for surfaces of articles (i.e., non-living articles) such as, for example, building surfaces in homes, businesses, and particularly hospitals. Exemplary home and commercial building surfaces include floors, door surfaces, bed surfaces, air conditioning surfaces, bathroom surfaces, railing surfaces, kitchen surfaces, and wall surfaces.

Also disclosed is an article comprising the disclosed cationic polymer disposed on a surface of a medical device. Non-limiting medical devices include swabs, catheters, sutures, stents, bedpans, gloves, facial masks, absorbent pads, absorbent garments, internal absorbent devices, insertable mechanical devices, wound dressings, and surgical instruments. Surfaces of the articles can comprise materials such as wood, paper, metal, cloth, plastic, rubber, glass, paint, leather, or combinations thereof. A method comprises disposing the antimicrobial composition on a surface of a medical device, wherein the composition is an effective antimicrobial agent against a Gram-negative microbe and Gram-positive microbe.

Loaded Complexes.

The cationic polymer can form a loaded complex (polyplexes) with negatively charged biologically active substances such as genes, nucleotides, proteins, peptides, drugs, or a combination thereof, thereby providing a therapeutic agent capable of two or more independent biological functions (e.g., antimicrobial function, gene and/or drug delivery function, and/or cell recognition function). A method for treating a cell and/or a surface comprises i) forming a loaded complex comprising the cationic polymer and a biologically active substance bound by non-covalent interactions; and ii) contacting the cell and/or the surface with the loaded complex. The cells can be exposed to the loaded complex in vitro, ex vivo and then subsequently placed into an animal, or in vivo (for example, an animal or human). In an embodiment, the biologically active substance is a gene, the loaded complex enters a cell, the gene is released by the loaded complex within the cell, and the gene is expressed by the cell. In another embodiment, the biologically active substance is a drug and/or a protein.

Exemplary commercially available drugs include 13-cis-Retinoic Acid, 2-CdA (Cladribine), 2-Chlorodeoxyadenosine (Cladribine), 5-Azacitidine, 5-Fluorouracil (Fluorouracil), 5-FU (Fluorouracil), 6-Mercaptopurine, 6-MP (6-Mercaptopurine), 6-TG (Thioguanine), 6-Thioguanine (Thioguanine), ABRAXANE® (Paclitaxel protein bound), ACCUTANE® (Isotretinoin), Actinomycin-D (Dactinomycin), ADRIAMYCIN® (Doxorubicin), ADRUCIL® (Fluorouracil), AFINITOR® (Everolimus), AGRYLIN® (Anagrelide), ALA-CORT® (Hydrocortisone), Aldesleukin, Alemtuzumab, ALIMTA® (Pemetrexed), Alitretinoin (9-cis-retinoic acid), Alkaban-AQ (Vinblastine), ALKERAN® (Melphalan), All-transretinoic Acid (Tretinoin), Alpha Interferon (Interferon Alfa), Altretamine, Amethopterin (Methotrexate), Amifostine, Aminoglutethimide, Anagrelide, ANANDRON® (Nilutamide), Anastrozole, Arabinosylcytosine (Cytarabine), Ara-C (Cytarabine), ARANESP® (Darbepoetin Alfa), AREDIA® (Pamidronate), ARIMIDEX® (Anastrozole), AROMASIN® (Exemestane), ARRANON® (Nelarabine), Arsenic Trioxide, Asparaginase, ATRA (All-transretinoic Acid), AVASTIN® (Bevacizumab), Azacitidine, BCG, BCNU (Carmustine), Bendamustine (Bendamustine Hydrochloride), Bevacizumab, Bexarotene, BEXXAR® (Tositumomab), Bicalutamide, BICNU® (Carmustine), BLENOXANE® (Bleomycin), Bleomycin, Bortezomib, Busulfan, BUSULFEX® (Busulfan), C225 (Cetuximab), Calcium Leucovorin (Leucovorin), CAMPATH® (Alemtuzumab), CAMPTOSAR® (Irinotecan), Camptothecin-11 (Irinotecan), Capecitabine, CARAC® (Fluorouracil), Carboplatin, Carmustine, Carmustine Wafer, CASODEX® (Bicalutamide), CC-5013 (Lenalidomide), CCI-779 (Temsirolimus), CCNU (Lomustine), CDDP (Cisplatin), CEENU® (Lomustine), CERUBIDINE® (Daunomycin), Cetuximab, Chlorambucil, Cisplatin, Citrovorum Factor (Leucovorin), Cladribine, Cortisone (Hydrocortisone), COSMOGEN® (Dactinomycin), CPT-11 (Irinotecan), Cyclophosphamide, CYTADREN® (Aminoglutethimide), Cytarabine, Cytarabine Liposomal, CYTOSAR-U® (Cytarabine), CYTOXAN® (Cyclophosphamide), Dacarbazine, DACOGEN® (Decitabine), Dactinomycin, Darbepoetin Alfa, Dasatinib, Daunomycin, Daunorubicin, Daunorubicin Hydrochloride, Daunorubicin Liposomal, DAUNOXOME® (Daunorubicin Liposomal), DECADRON™ (Dexamethasone), Decitabine, DELTA-CORTEF® (Prednisolone), DELTASONE® (Prednisone), Denileukin Diftitox, DEPOCYT® (Cytarabine Liposomal), Dexamethasone, Dexamethasone Acetate, Dexamethasone Sodium Phosphate, DEXASONE® (Dexamethasone), Dexrazoxane, DHAD (Mitoxantrone), DIC (Dacarbazine), DIODEX® (Dexamethasone), Docetaxel, DOXIL® (Doxorubicin Liposomal), Doxorubicin, Doxorubicin Liposomal, DROXIA® (Hydroxyurea), DTIC (Dacarbazine), DTIC-DOME® (Decarbazine), Duralone (Methylprednisolone), EFUDEX® (Fluorouracil), ELIGARD® (Leuprolide), ELLENCE® (Epirubicin), ELOXATIN® (Oxaliplatin), ELSPAR® (Asparaginase), EMCYT® (Estramustine), Epirubicin, Epoetin Alfa, ERBITUX® (Cetuximab), Erlotinib, *Erwinia* L-asparaginase (Asparaginase), Estramustine, ETHYOL® (Amifostine), ETOPOPHOS® (Etoposide), Etoposide, Etoposide Phosphate, EULEXIN® (Flutamide), Everolimus, EVISTA® (Raloxifene), Exemestane, FARESTON® (Toremifene), FASLODEX® (Fulvestrant), FEMARA® (Letrozole), Filgrastim, Floxuridine, FLUDARA® (Fludarabine), Fludarabine, FLUOROPLE® (Fluorouracil), Fluorouracil, Fluorouracil (cream), Fluoxymesterone, Flutamide, Folinic Acid (Leucovorin), FUDR® (Floxuridine), Fulvestrant, G-CSF (Pegfilgrastim), Gefitinib, Gemcitabine, Gemtuzumab ozogamicin, GEMZAR® (Gemcitabine), GLEEVEC® (Imatinib mesylate), GLIADEL® Wafer (Carmustine Wafer), GM-CSF (Sargramostim), Goserelin, Granulocyte-Colony Stimulating Factor (Pegfilgrastim), Granulocyte Macrophage Colony Stimulating Factor (Sargramostim), HALOTESTIN® (Fluoxymesterone), HERCEPTIN® (Trastuzumab), HEXADROL® (Dexamethasone), HEXALEN® (Altretamine), Hexamethylmelamine (Altretamine), HMM (Altretamine), HYCAMTIN® (Topotecan), HYDREA® (Hydroxyurea), Hydrocort Acetate (Hydrocortisone), Hydrocortisone, Hydrocortisone Sodium Phosphate, Hydrocortisone Sodium Succinate, HYDROCORTONE® Phosphate (Hydrocortisone), Hydroxyurea, Ibritumomab, Ibritumomab Tiuxetan (Ibritumomab), IDAMYCIN® (Idarubicin), Idarubicin, IFEX® (Ifosfamide), IFN-alpha (Interferon alfa), Ifosfamide, IL-11 (Oprelvekin), IL-2 (Aldesleukin), Imatinib mesylate, Imidazole Carboxamide (Decarbazine), Interferon alfa, Interferon Alfa-2b (PEG Conjugate), Interleukin-2 (Aldesleukin), Interleukin-11 (Oprelvekin), INTRON® A (interferon alfa-2b), IRESSA® (Gefitinib), Irinotecan, Isotretinoin, Ixabepilone, IXEMPRA® (Ixabepilone), Kidrolase (Asparaginase), LANACORT® (Hydrocortisone), Lapatinib, L-asparaginase, LCR (Vincristine), Lenalidomide, Letrozole, Leucovorin, LEUKERAN® (Chlorambucil), LEUKINE® (Sargramostim), Leuprolide, Leurocristine (Vincristine), LEUSTATIN® (Cladribine), Liposomal Ara-C, LIQUID PRED® (Prednisone), Lomustine, L-PAM (Melphalen), L-Sarcolysin (Melphalen), LUPRON® (Leuprolide), LUPRON DEPOT® (Leuprolide), MATULANE® (Procarbazine), MAXIDEX® (Dexamethasone), Mechlorethamine, Mechlorethamine Hydrochloride, Medralone (Methylprednisolone), MEDROL® (Methylprednisolone), MEGACE® (Megestrol), Megestrol, Megestrol Acetate (Megastrol), Melphalan, Mercaptopurine (6-Mercaptopurine), Mesna, MESNEX® (Mesna), Methotrexate, Methotrexate Sodium (Methotrexate), Methylprednisolone, METICORTEN® (Prednisone), Mitomycin (Mitomycin C), Mitomycin-C, Mitoxantrone, M-Prednisol (Methylprednisolone), MTC (Mitomycin-C), MTX (Methotrexate), MUSTARGEN® (Mechlorethamine), Mustine (Mechlorethamine), MUTAMYCIN® (Mitomycin-C), MYLERAN® (Busulfan), MYLOCEL® (Hydroxyurea), MYLOTARG® (Gemtuzumab ozogamicin), NAVELBINE® (Vinorelbine), Nelarabine, NEOSAR® (Cyclophosphamide), NEULASTA® (Pegfilgrastim), NEUMEGA® (Oprelvekin), NEUPOGEN® (Filgrastim), NEXAVAR® (Sorafenib), NILANDRON® (Nilutamide), Nilutamide, NIPENT® (Pentostatin), Nitrogen Mustard (Mechlorethamine), NOLVADEX® (Tamoxifen), NOVANTRONE® (Mitoxantrone), Octreotide, Octreotide acetate (Octreotide), ONCASPAR® (Pegaspargase), ONCOVIN® (Vincristine), ONTAK® (Denileukin Diftitox), ONXOL® (Paclitaxel), Oprelvekin (Interleukin-11), ORAPRED® (Prednisolone), ORASONE® (Prednisone), Oxaliplatin, Paclitaxel, Paclitaxel Protein-bound, Pamidronate, Panitumumab, PANRETIN® (Alitretinoin), PARAPLATIN® (Carboplatin), PEDIAPRED® (Prednisolone), PEG Interferon, Pegaspargase, Pegfilgrastim, PEG-INTRON® (Interferon Alfa-2b), PEG-L-asparaginase, Pemetrexed, Pentostatin, Phenylalanine Mustard (Melphalen), PLATINOL® (Cisplatin), Platinol-AQ (Cisplatin), Prednisolone, Prednisone, PRELONE® (Prednisolone), Procarbazine, PROCRIT® (Epoetin Alfa), PROLEUKIN® (Aldesleukin), Prolifeprospan 20 with Carmustine Implant (Carmustine Wafer), PURINETHOL® (6-Mercaptopurine), Raloxifene, REVLIMID® (Lenalidomide), RHEUMATREX® (Methotrexate), RITUXAN® (Rituximab), Rituximab, Roferon-A (Interferon Alfa-2a), RUBEX® (Doxorubicin), Rubidomycin hydrochloride (Daunomycin), SANDOSTATIN® (Octreotide), SANDOSTATIN LAR® (Octreotide), Sargramostim, SOLU-CORTEF® (Hydrocortisone), SOLU-MEDROL® (Methylprednisolone), Sorafenib, SPRYCEL® (Dasatinib), STI-571 (Imatinib Mesylate), Streptozocin, SU11248 (Sunitinib), Sunitinib, SUTENT® (Sunitinib), Tamoxifen, TARCEVA® (Erlotinib), TARGRETIN® (Bexarotene), TAXOL® (Paclitaxel), TAXOTERE® (Docetaxel), TEMODAR® (Temozolomide), Temozolomide, Temsirolimus, Teniposide, TESPA (Thiotepa), Thalidomide, THALOMID® (Thalidomide), THERACYS® (BCG), Thioguanine, Thioguanine Tabloid (Thioguanine), Thiophosphoamide (Thiotepa), THIOPLEX® (Thiotepa), Thiotepa, TICE® (BCG), TOPOSAR® (Etoposide), Topotecan, Toremifene, TORISEL® (Temsirolimus), Tositumomab, Trastuzumab, TREANDA® (Bendamustine Hydrochloride), Tretinoin, TREXALL® (Methotrexate), TRISENOX® (Arsenic Trioxide), TSPA (Thiotepa), TYKERB® (Lapatinib), VCR (Vincristine), VECTIBIX® (Panitumumab), VELBAN® (Vinblastine), VELCADE® (Bortezomib), VEPESID® (Etoposide), VESANOID® (Tretinoin), VIADUR® (Leuprolide), VIDAZA® (Azacitidine), Vinblastine, Vinblastine Sulfate, VINCASAR PFS® (Vincristine), Vincristine, Vinorelbine, Vinorelbine tartrate (Vinorelbine), VLB (Vinblastine), VM-26 (Teniposide), Vorinostat, VP-16 (Etoposide), VUMON® (Teniposide), XELODA® (Capecitabine), ZANOSAR® (Streptozocin), ZEVALIN® (Ibritumomab), ZINECARD® (Dexrazoxane), ZOLADEX® (Goserelin), Zoledronic acid, ZOLINZA® (Vorinostat), and ZOMETA® (Zoledronic acid).

Any cell that can be transfected by a non-viral vector can be treated with the above-described loaded complexes. In particular the cells can be eukaryotic cells, mammalian cells, and more particularly rodent or human cells. The cells can be derived from various tissues, including extraembryonic or embryonic stem cells, totipotent or pluripotent, dividing or non-dividing, parenchyma or epithelium, immortalized or transformed, or the like. The cell can be a stem cell or a differentiated cell. Cell types that are differentiated include adipocytes, fibroblasts, myocytes, cardiomyocytes, endothelium, dendritic cells, neurons, glia, mast cells, blood cells and leukocytes (e.g., erythrocytes, megakaryotes, lymphocytes, such as B, T and natural killer cells, macrophages, neutrophils, eosinophils, basophils, platelets, granulocytes), epithelial cells, keratinocytes, chondrocytes, osteoblasts, osteoclasts, hepatocytes, and cells of the endocrine or exocrine glands, as well as sensory cells.

The above-described loaded complexes can be used as non-viral transfection vectors. The target gene is not limited to any particular type of target gene or nucleotide sequence. For example, the target gene can be a cellular gene, an endogenous gene, an oncogene, a transgene, a viral gene, or translated and non-translated RNAs. Exemplary possible target genes include: transcription factors and developmental genes (e.g., adhesion molecules, cyclin-dependent kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, ERBB2, ETSI, ETV6, FGR, FOS, FYN, HCR, HRAS, JUN, KRAS, LCK, LYN, MDM2, MLL, MYB, MYC, MYCLI, MYCN, NRAS, PIMI, PML, RET, SKP2, SRC, TALI, TCL3, and YES); tumor suppressor genes (e.g., APC, BRAI, BRCA2, CTMP, MADH4, MCC, NFI, NF2, RBI, TP53, and WTI); and enzymes (e.g., ACP desaturases and hydroxylases, ADP-glucose pyrophorylases, ATPases, alcohol dehydrogenases, amylases, amyloglucosidases, catalases, cyclooxygenases, decarboxylases, dextrinases, DNA and RNA polymerases, galactosidases, glucose oxidases, GTPases, helicases, integrases, insulinases, invertases, isomerases, kinases, lactases, lipases, lipoxygenases, lysozymes, peroxidases, phosphatases, phospholipases, phosphorylases, proteinases and peptidases, recombinases, reverse transcriptases, telomerase, including RNA and/or protein components, and topoisomerases).
Charge Shifting.

The release of a biologically active substance can be facilitated by cationic polymers capable of charge-shifting. In charge shifting, the net positive charge of the cationic polymer is reduced by the conversion of a non-charged group on the cationic polymer side chain into a negatively charged group after the loaded complex has entered the cell. A cationic polymer capable of charge-shifting can comprise, for example, a latent carboxylic acid group, such as an acetal ester, in addition to the quaternary amine. The acetal ester group has the general formula (16):

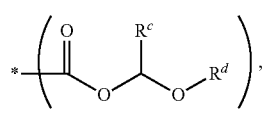

(16)

wherein the starred bond represents the attachment point to a cyclic carbonyl moiety, and $R^c$ and $R^d$ are monovalent radicals independently comprising from 1 to 20 carbons. In an embodiment, $R^c$ is methyl and $R^d$ is ethyl. In another embodiment, a diluent cyclic carbonyl monomer is MTCOEE:

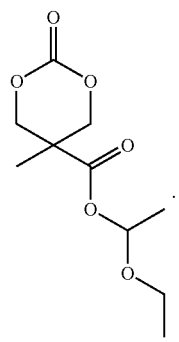

(MTCOEE)

Acetal esters can be hydrolyzed under the mildly acidic conditions of the endosomal environment (about pH 5) to form a carboxylic acid group. In the more basic environment of the cytosol, the carboxylic acid groups become ionized, thereby lowering the net positive charge of the cationic polymer and allowing the release of the negative charged biologically active substance. Thus, the cationic polymers can be easily modified to tune the charge and the buffering strength for a specific biologically active substance.

Another strategy for facilitating endosomal release involves non-covalent interactions to stabilize a biologically active substance, for example, using diluent cyclic carbonyl monomers comprising a fluorinated tertiary alcohol group. Fluorinated tertiary alcohol groups are known to bind to phosphates and related structures, but with interaction energies that are lower than electrostatic interactions, and hence more easily released.

Other functional groups can be used to facilitate the release of the biologically active substance from the loaded complex, such as secondary amine groups, citraconic amide groups, ester groups, and imine groups.

The examples below demonstrate that compositions comprising a cationic polymer have strong antimicrobial activity against Gram-negative microbes, such as *Esherichia coli*, and Gram-positive microbes, such as *Staphylococcus aureus*, fungi, and yeast.

EXAMPLES

Materials used in the following examples are listed in Table 11.

TABLE 11

| ABBREVIATION | DESCRIPTION | SUPPLIER |
| --- | --- | --- |
| Bis-MPA | 2,2-Bis(hydroxymethyl)propionic acid, MW 134.13 | Sigma-Aldrich |
| DBU | 1,8-Diazabicyclo[5.4.0]undec-7-ene, MW 152.24 | Sigma-Aldrich |
| TU | N-bis(3,5-Trifluoromethyl)phenyl-N'-cyclohexylthiourea | Prepared below |
| Sparteine | (−)-sparteine; (6R,8S,10R,12S)-7,15-Diazatetracyclo[7.7.1.02,7.010,15]heptadecane, accelerator, MW 234.38 | Sigma-Aldrich |
| PBS | Phosphate Buffered Saline | Invitrogen |
| TSB | Tryptic Soy Broth | Becton, Dickinson and Co., USA |
| TMEDA | N,N,N',N'-tetramethylethylenediamine, MW 116.24 | Merck, Singapore |
| TCTP | Tissue Culture Plate, Nunc MicroWell ™ Treated Polystyrene (Catlog No. 167008) | Nunc |
| PFC | Bis(pentafluorophenyl) carbonate, MW 394.12 | Central Glass Co., Ltd. |
| CsF | Cesium fluoride; catalyst, MW 151.90 | Sigma-Aldrich |
|  | p-Chloromethyl Benzyl Alcohol, MW 156.61 | Sigma-Aldrich |
| DMEA | N,N-Dimethylethanolamine, MW 89.14 | Sigma-Aldrich |
| PBOH | Pyrenebutanol, MW 274.36 | Sigma-Aldrich |
| MEM | Minimal Essential Medium (cell culture medium) | Invitrogen (U.S.A) |
| RPMI-1640 | Cell culture medium | Invitrogen (U.S.A) |
| FBS | Fetal Bovine Serum | Invitrogen (U.S.A) |
| TMC | Trimethylene Carbonate (1,3-dioxan-2-one), MW 102.09 | Sigma-Aldrich |

Herein, Mn is the number average molecular weight, Mw is the weight average molecular weight, and MW is the molecular weight of one molecule.

Diethyl ether, triethylamine (TEA), potassium hydroxide (KOH) and N,N,N',N'-tetramethylethylenediamine (TMEDA) were purchased from Merck, Singapore. Anhydrous dichloromethane (DCM), dimethylformamide (DMF), tetrahydrofuran (THF) and pyridine were purchased from Sigma-Aldrich. 2,2-Bis(hydroxymethyl)propionic acid (bis-MPA), benzyl bromide (BnBr), triphosgene and Pd/C (10%) were purchased from Sigma-Aldrich. 1,8-Diazabicyclo [5.4.0]undec-7-ene (DBU) was dried with $CaH_2$ overnight and distilled under reduced pressure before stored in a glove box. *Staphylococcus aureus* (*S. aureus*), *Escherichia coli* (*E. coli*) and *Candida albicans* (*C. albicans*), *Pseudomonas aeruginosa* (*P. aeruginosa*) and *Bacillicus subtilis* (*B. subtilis*) were purchased from ATCC. All other chemicals were of analytical grade, and used as received.

Polymer Characterization.

The nuclear magnetic resonance ($^1$H-NMR) spectra of the polymers were studied using a Bruker Avance 400 spectrometer (400 MHz), and chloroform-d ($CDCl_3$) was used as the solvent. The molecular weights and polydispersity indices were determined by a gel permeation chromatography (GPC) (Waters 2690, MA, USA, mobile phase: THF at 1.0 ml/min, relative to polystyrene standards).

I. Monomer Synthesis.

Scheme 3 illustrates pathways for preparing cyclic carbonate monomers from 2,2-bis(methylol)propionic acid (bis-MPA).

Scheme 3.

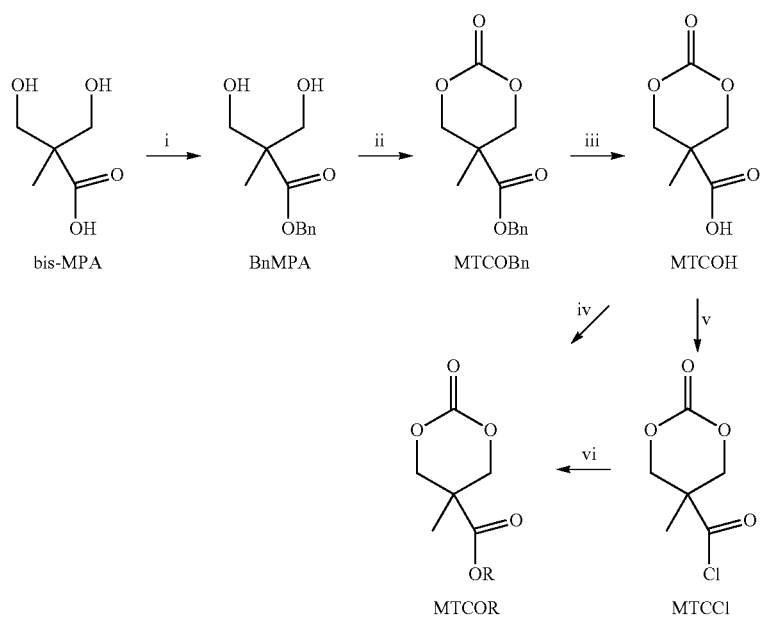

In Scheme 3, (i) 2,2-bis(methylol)propionic acid (bis-MPA) is converted to a benzyl ester BnMPA (herein also used as an initiator for the polymerizations). In reaction (ii) BnMPA reacts with triphosgene to form a cyclic carbonate monomer, MTCOBn. MTCOBn is debenzylated in (iii) to produce the cyclic carbonyl carboxylic acid, MTCOH. Two pathways are shown for forming an ester from MTCOH. In the first pathway, (iv), MTCOH is treated with a suitable carboxy activating agent, such as dicyclohexylcarbodiimide (DCC), which reacts with ROH to form MTCOR in a single step. Alternatively, MTCOH can be converted first (v) to the acid chloride MTCCl followed by treatment (vi) of MTCCl with ROH in the presence of a base to form MTCOR. Both pathways are illustrative and are not meant to be limiting. The following conditions are typical for the reactions of Scheme 3: (i) Benzylbromide (BnBr), KOH, DMF, 100° C., 15 hours, 62% yield of the benzyl ester of bisMPA; (ii) triphosgene, pyridine, $CH_2Cl_2$, −78° C. to 0° C., 95% yield of MTCOBn; (iii) Pd/C (10%), $H_2$ (3 atm), EtOAc, room temperature, 24 hours, 99% yield of MTCOH; (iv) ROH, DCC, THF, room temperature, 1 to 24 hours; (v) $(COCl)_2$, THF, room temperature, 1 hour, 99% yield of MTCCl; (vi) ROH, $NEt_3$, room temperature, 3 hours yields MTCOR.

Cyclic carbonate haloesters MTCOPrBr, MTCOPrCl, MTCOEtI can be prepared by reaction of MTCCl with 3-bromopropanol, 3-choloropropanol, and 2-iodoethanol, respectively, as described below for MTCOPrCl. The haloesters were purified by either recrystallization or by flash chromatography (ethyl acetate/hexane) in high yields (>85%).

Example 1. Preparation of MTCOPrCl, MW 236.65

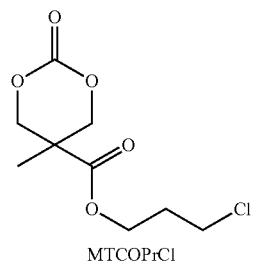

MTCOPrCl

A catalytic amount (3 drops) of DMF was added to a THF solution (200 mL) of MTCOH (11.1 g, 69 mmol), followed by a solution of oxalyl chloride (7.3 mL, 87 mmol) in THF (100 mL), gently added over 20 min under $N_2$ atmosphere. The solution was stirred for 1 hour, bubbled with N2 flow to remove volatiles, and evaporated under vacuum to give the intermediate MTCCl. A mixture of 3-chloro-1-propanol (5.4 mL, 76 mmol) and pyridine (6.2 mL, 65 mmol) in dry THF (50 mL) was added dropwise to a dry THF solution (100 mL) of the intermediate MTCCl over 30 min, while maintaining a solution temperature below 0° C. with an ice/salt bath. The reaction mixture was kept stirring for another 3 hours at room temperature before it was filtered and the filtrate evaporated. The residue was dissolved in methylene chloride and washed with 1N HCl aqueous solution, saturated $NaHCO_3$ aqueous solution, brine and water, stirred with $MgSO_4$ overnight, and the solvent evaporated. The crude product was passed through a silica gel column by gradient eluting of ethyl acetate and hexane (50/50 to 80/20)

to provide the product as a colorless oil that slowly solidified to a white solid (9.8 g, 60%).

Example 2. Preparation of Ethyl 2,2-bis(methylol)propionate (EtMPA), Molecular Weight 162.2

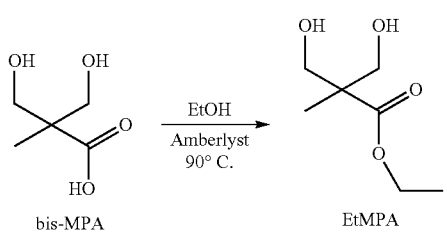

2,2-Bis(methylol)propionic acid (bis-MPA; MW 134.1, 22.1 g, 0.165 mol) was added in ethanol (150 mL) with Amberlyst-15 (6.8 g) and refluxed overnight. The resins were then filtered out and the filtrate was evaporated. Methylene chloride (200 mL) was added to the resulting viscous liquid to filtrate the unreacted reagent and byproduct. After the solution was dried over MgSO4 and evaporated, ethyl 2,2-bis(methylol)propionate (EtMPA) was obtained as a clear and colorless liquid (21.1 g, 86%).

Example 3. Preparation of N-bis(3,5-trifluoromethyl)phenyl-N'-cyclohexylthiourea (TU)

TU was prepared as reported by R. C. Pratt, B. G. G. Lohmeijer, D. A. Long, P. N. P. Lundberg, A. Dove, H. Li, C. G. Wade, R. M. Waymouth, and J. L. Hedrick, Macromolecules, 2006, 39 (23), 7863-7871, and dried by stirring in dry THF over CaH2, filtering, and removing solvent under vacuum.

Example 4. Preparation of MTCOEt, MW 188.2

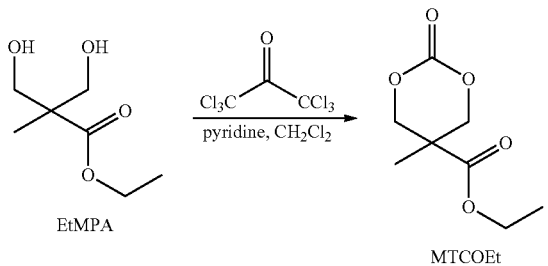

MTCOEt was prepared from EtMPA as a non-functional counterpart for dilution effects and to introduce hydrophobic repeat units in the polycarbonate chain.

A solution of triphosgene (19.5 g, 0.065 mol) in $CH_2Cl_2$ (200 mL) was added stepwise to a $CH_2Cl_2$ solution (150 mL) of ethyl 2,2-bis(methylol)propionate (EtMPA) (21.1 g, 0.131 mol) and pyridine (64 mL, 0.786 mol) over 30 min at −75° C. with dry ice/acetone. The reaction mixture was kept stirring for another 2 hours under chilled condition and then allowed to heat to room temperature. Saturated $NH_4Cl$ aqueous solution (200 mL) was added to the reaction mixture to decompose excess triphosgene. The organic phase was then treated with 1N HCl aq (200 mL), followed by saturated $NaHCO_3$ (200 mL), brine (200 mL), and water (200 mL). After the $CH_2Cl_2$ solution was dried over $MgSO_4$ and evaporated, the residue was recrystallized from ethyl acetate to give white crystals (13.8 g, 56%). $^1H$ NMR: delta 4.68 (d, 2H, $CH_2OCOO$), 4.25 (q, 1H, $OCH_2CH_3$), 4.19 (d, 2H, $CH_2OCOO$), 1.32 (s, 3H, $CH_3$), 1.29 (t, 3H, $CH_3CH_2O$). $^{13}C$ NMR: delta 171.0, 147.5, 72.9, 62.1, 39.9, 17.3, 13.8. HR-ESI-MS: m/z calcd for $C_8H_{12}O_5$; Na, 211.0582. found, 221.0578.

An alternative route to functionalized cyclic carbonate monomers utilizes a cyclic carbonate monomer intermediate bearing an active pentafluorophenyl ester, MTC-PhF5, which is formed in a single step from bis-MPA as follows.

Example 5. Preparation of $MTCOC_6F_5$, MW 326

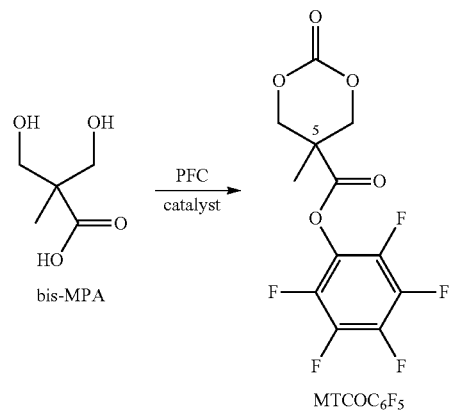

A 100 mL round bottom flask was charged with bis-MPA (5.00 g, 37 mmol), bis-(pentafluorophenyl) carbonate (PFC, 31.00 g, 78 mmol), and CsF (2.5 g, 16.4 mmol) rinsed in with THF (70 mL). Initially the reaction was heterogeneous. After one hour a clear homogeneous solution was formed that was allowed to stir for 20 hours. The solvent was removed in vacuo and the residue was re-dissolved in methylene chloride. The solution was allowed to stand for approximately 10 minutes, at which time the pentafluorophenol byproduct precipitated and could be quantitatively recovered. This pentafluorophenol byproduct showed the characteristic 3 peaks in the $^{19}F$ NMR of pentafluorophenol and a single peak in the GCMS with a mass of 184. The filtrate was extracted with sodium bicarbonate, water and was dried with $MgSO_4$. The solvent was evaporated in vacuo and the product was recrystallized (ethyl acetate/hexane mixture) to give $MTCOC_6F_5$ as a white crystalline powder (GCMS single peak with mass of 326 g/mol, calculated molecular weight for $C_{12}H_7F_5O_5$ (326 g/mol) consistent with the assigned structure. $^1H$-NMR (400 MHz in $CDCl_3$): delta 4.85 (d, J=10.8 Hz, 2H, $CH_2$), 4.39 (d, J=10.8 Hz, 2H, $CH_2$), 1.55 (s, 3H, $CH_3$).

$MTCOC_6F_5$ was then used to prepare additional cyclic carbonyl monomers as follows.

Example 6. Preparation of MTCOBnCl, MW 298.72

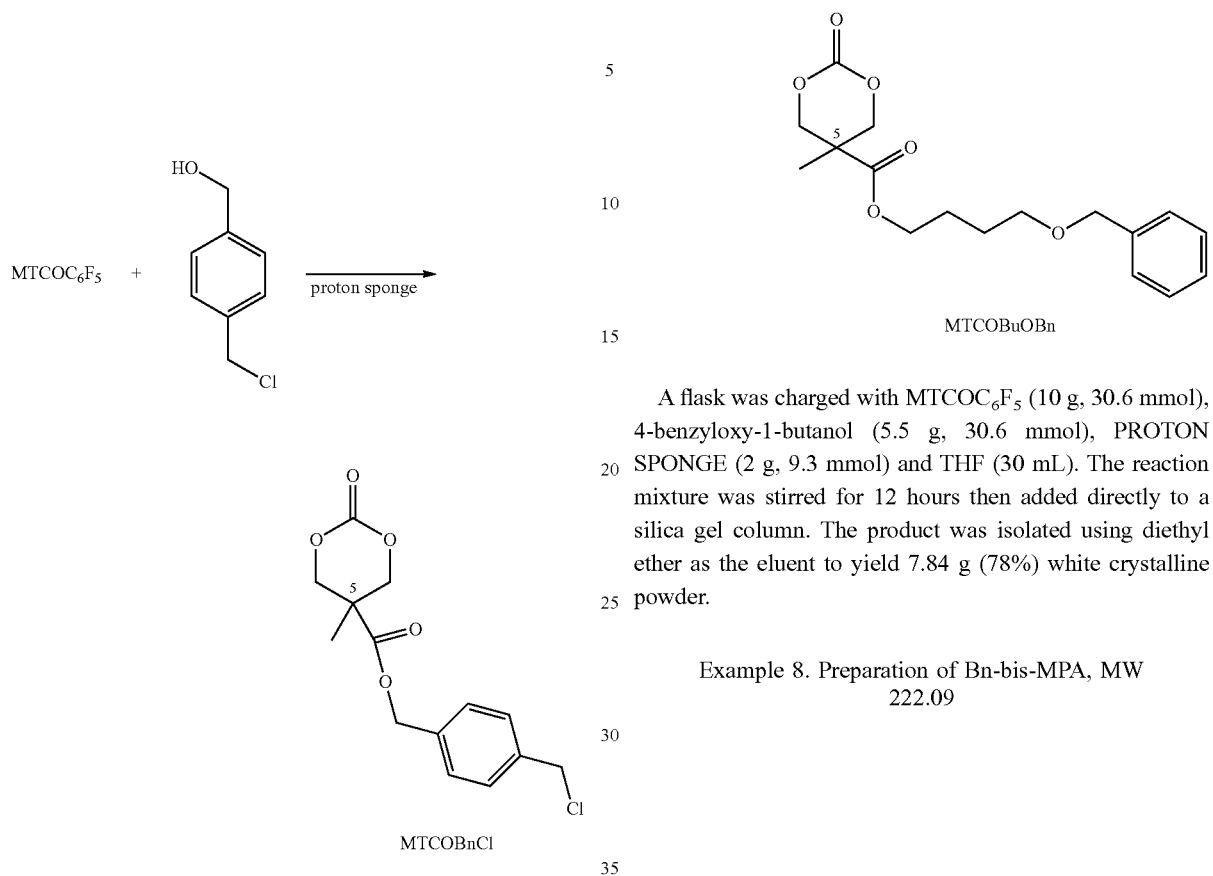

MTCOBnCl

A flask was charged with MTCOC₆F₅ (10 g, 30.6 mmol), p-chloromethyl benzyl alcohol (4.8 g, 30.6 mmol), PROTON SPONGE (2 g, 9.3 mmol, a trademark of Sigma-Aldrich) and THF (30 mL). The reaction mixture was stirred for 12 hr then added directly to a silica gel column. The product was isolated using diethyl ether as the eluent to yield 7.45 g (81%) white crystalline powder.

Example 7. Preparation of MTCOBuOBn, MW 322.35

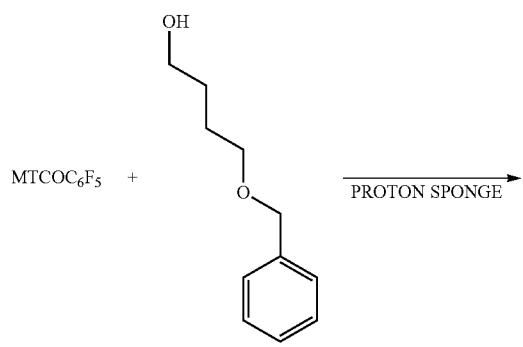

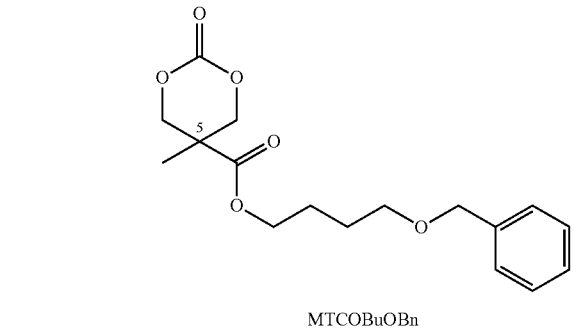

MTCOBuOBn

A flask was charged with MTCOC₆F₅ (10 g, 30.6 mmol), 4-benzyloxy-1-butanol (5.5 g, 30.6 mmol), PROTON SPONGE (2 g, 9.3 mmol) and THF (30 mL). The reaction mixture was stirred for 12 hours then added directly to a silica gel column. The product was isolated using diethyl ether as the eluent to yield 7.84 g (78%) white crystalline powder.

Example 8. Preparation of Bn-bis-MPA, MW 222.09

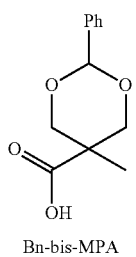 [SMILES: CC1(C(=O)O)COC(c2ccccc2)OC1]

Bn-bis-MPA

This preparation followed the procedure described by Frechet, et al., JACS (2001), 123, 5908. 2,2-Bis(hydroxymethyl)-propionic acid 20.00 g (149 mmol), 34.04 g (222 mmol) benzaldehyde dimethyl acetal, and 1.42 g (7.4 mmol) p-toluenesulfonic acid monohydrate (TsOH) were mixed in 150 mL of acetone. The reaction mixture was stirred for 4 hours at ambient temperature. After storage of the reaction mixture in the refrigerator overnight, solids were filtered off and washed with cold acetone to give protected Bn-bis-MPA as white crystals: 21.0 g, (64%). IR (cm⁻¹, thin film from CHCl₃): 3400-2300 (br), 1699 (s). $^1$H NMR (500 MHz, CDCl₃): delta 1.11 (s, 3), 3.70 (d, 2, J) 11.7), 4.63 (d, 2, J) 11.4), 5.49 (s, 1), 7.37 (m, 3), 7.48 (m, 2). $^{13}$C NMR (500 MHz, CDCl₃): delta 17.58, 41.58, 72.65, 100.37, 126.10, 128.01, 128.70, 138.39, 175.58. Calcd.: [M]+m/z) 222.24. Found: TOFMS-ES: [M+Na]+) 245.10. Anal. Calcd for C₁₂H₁₄O₄: C, 64.89; H, 6.52.

Example 9. Preparation of Bn-bis-MPA Anhydride, MW 426.17

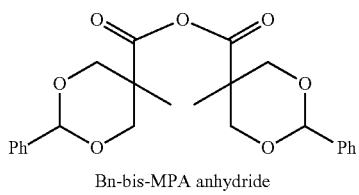 [SMILES: CC1(C(=O)OC(=O)C2(C)COC(c3ccccc3)OC2)COC(c2ccccc2)OC1]

Bn-bis-MPA anhydride

Bn-bis-MPA (20.00 g, 90 mmol) and 10.21 g (49.5 mmol) of N,N'-dicyclohexylcarbodiimide (DCC) were mixed in 150 mL of $CH_2Cl_2$. The reaction mixture was stirred overnight at room temperature. The precipitated urea DCC byproduct was filtered off in a glass filter and washed with a small volume of $CH_2Cl_2$. The crude product was purified by precipitating the filtrate into 1000 mL of hexane under vigorous stirring. After filtration, Bn-bis-MPA anhydride was isolated as white crystals: 17.1 g (89%). IR (cm-1, thin film from $CHCl_3$): 3050, 1814 (s), 1746 (s). $^1H$ NMR (300 MHz, $CDCl_3$): delta 1.12 (s, 6), 3.69 (d, 4, J) 10.5), 4.66 (d, 4, J) 10.5), 5.47 (s, 2), 7.35 (m, 6), 7.45 (m, 4). $^{13}C$ NMR (400 MHz, $CDCl_3$): delta 16.85, 44.18, 73.17, 102.11, 126.27, 128.22, 129.09, 137.56, 169.12. Calcd.: [M]+m/z) 426.46. Found: TOFMS-ES: [M+Na]+) 449.20. Anal. Calcd for $C_{24}H_{26}O_7$: C, 67.59; H, 6.15.

II. Initiator Synthesis (Polyol).

Example 10. Preparation of Dendrimer G-1(OH)$_8$, MW 600.61

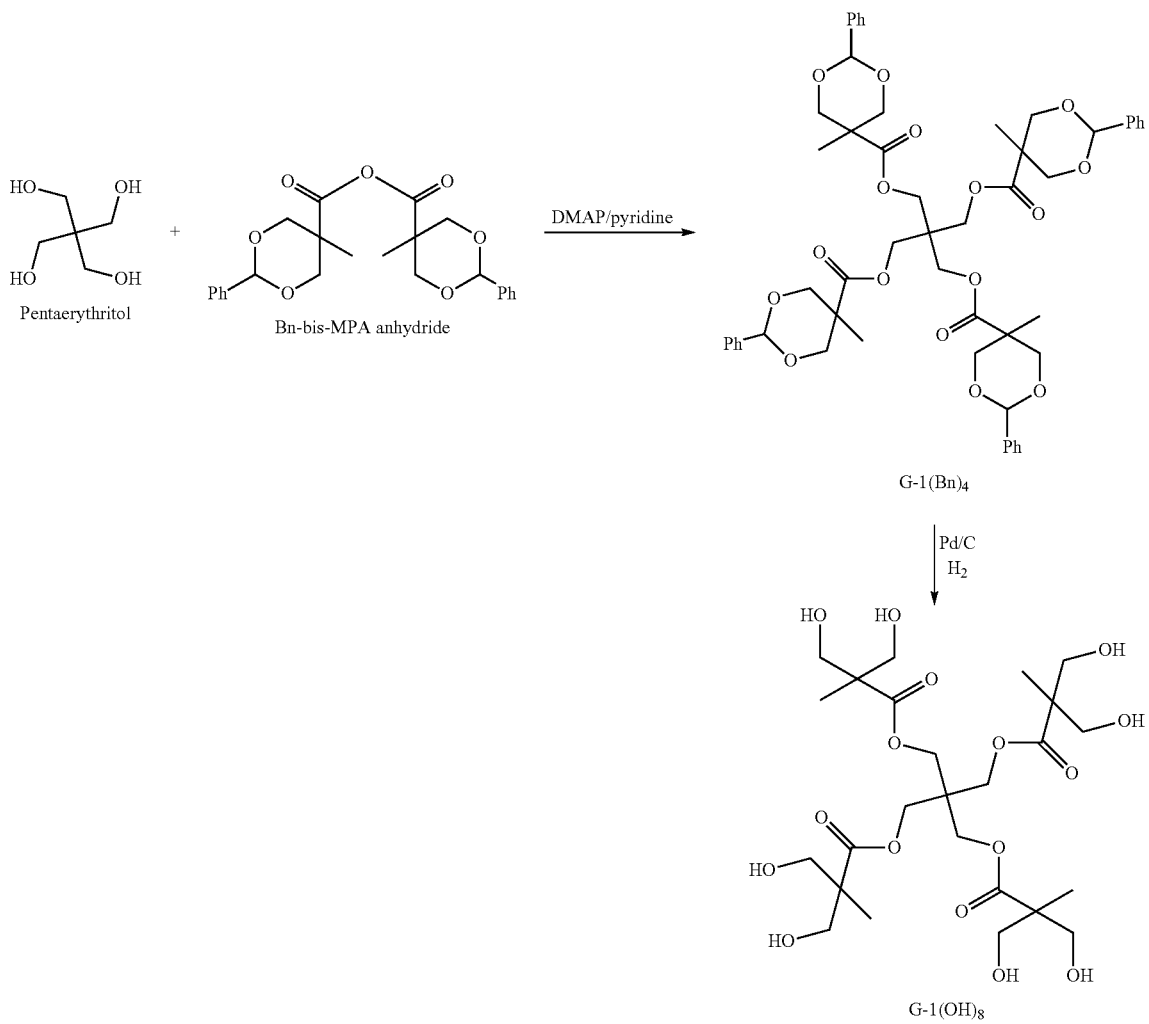

The following is representative of the preparation of a dendritic polyol ROP initiator (star polymer). A flask was charged with pentaerythritol, Bn-bis-MPA anhydride (1.2 equivalents per hydroxyl group) DMAP, pyridine and THF. The reaction mixture was stirred until all hydroxyl groups were esterified. Water was then added to hydrolyze any unreacted anhydride and then the product was washed with $Na_2CO_3$ followed by 1 M HCl. The benzyl protecting groups were removed by hydrogenolyis using Pd/C, EtOAc/MeOH, and $H_2$ (40 psi).

Example 11. Preparation of Dendrimer G-2(OH)$_{16}$, MW 1529.53
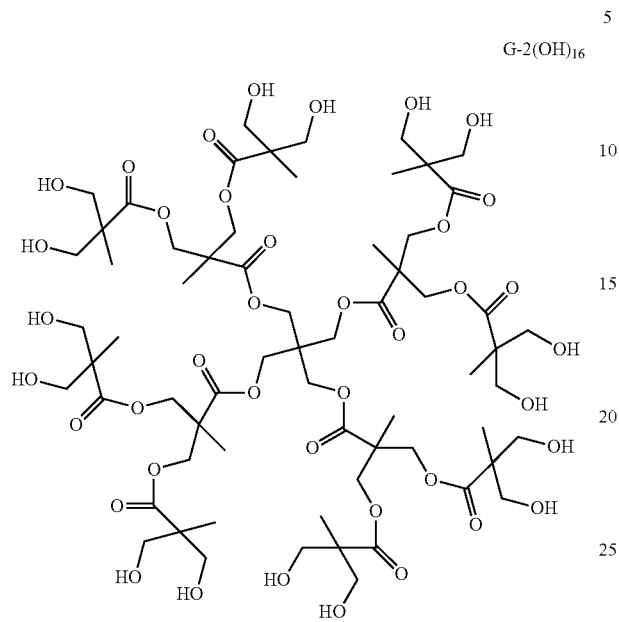
G-2(OH)$_{16}$
G-2(OH)$_{16}$ was prepared from G-1(OH)$_8$ following the general procedure described above for the preparation of G-1(OH)$_8$.
Example 12. Preparation of Dendrimer G-3(OH)$_{32}$, MW 3387.37
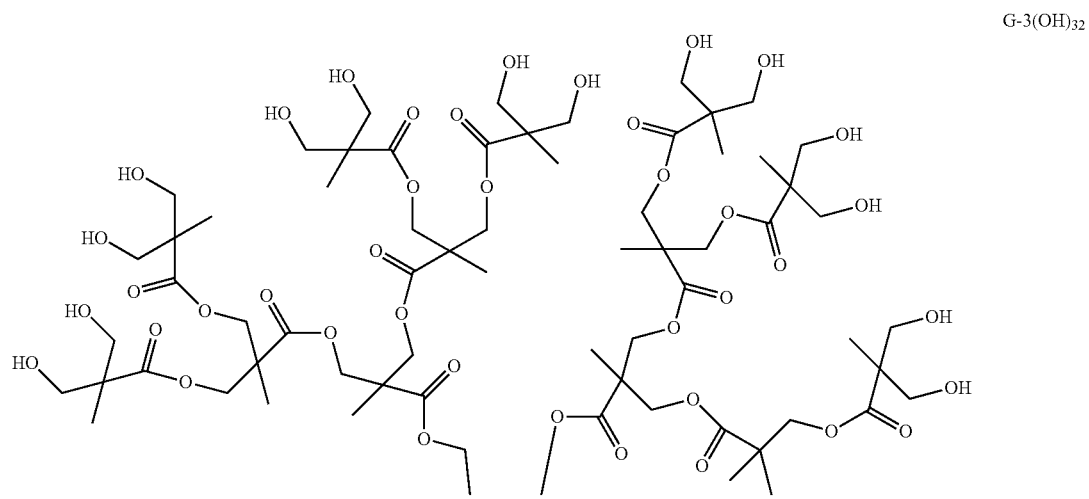
G-3(OH)$_{32}$ -continued
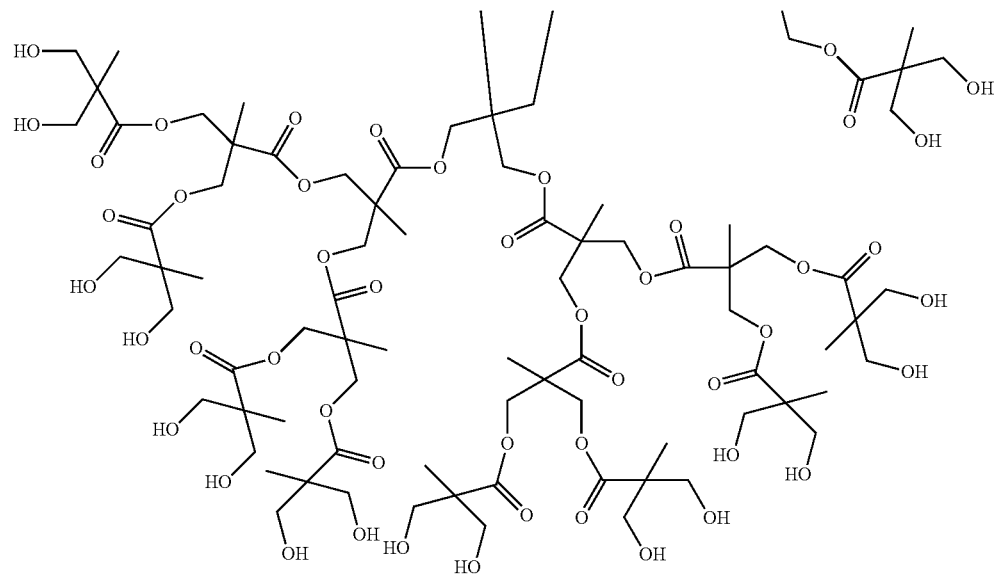
G-3(OH)$_{32}$ was prepared from G-1(OH)$_{16}$ following the general procedure described above for the preparation of G-1(OH)$_8$.
Example 13. Preparation of Linear Polycarbonate ROP Initiator PC-1
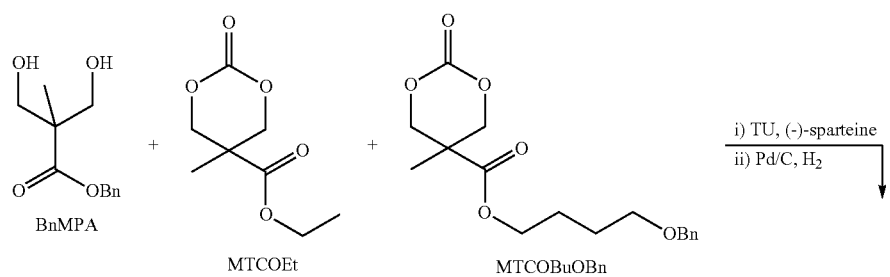

-continued

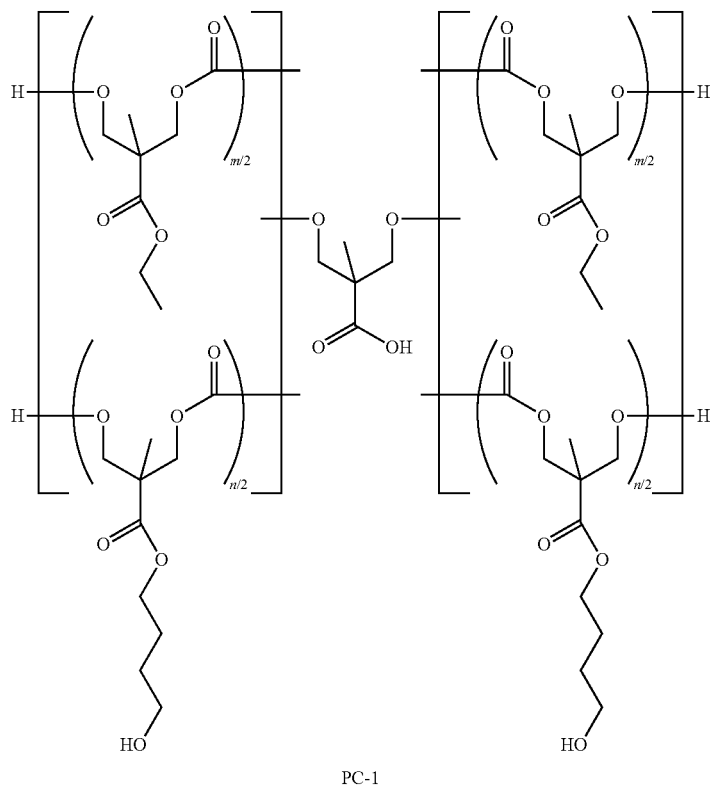

PC-1

Bn = benzyl

In a N₂ filled glovebox a flask was charged with MTCOEt (0.65 g, 3.45 mmol), MTCOBuOBn (0.69 g, 2.02 mmol), thiourea (TU) (0.05 g, 0.14 mmol), BnMPA (0.0113 g, 0.05 mmol) and DCM (2 mL). Upon complete dissolution (−)-sparteine (0.03 g, 0.13 mmol) was added with stirring to initiate the polymerization. After 6 hours the reaction mixture was precipitated into cold 2-propanol to yield 1.12 g (80.5%) of benzyl protected amorphous polycarbonate random copolymer. Mn 12.5 kDa; PDI 1.08. The benzyl protected polymer was deprotected by hydrogenolysis using Pd/C and hydrogen. The vertical stacking of the repeat units in the structure of PC-1 indicates a random polymer chain. In the above structure for PC-1, m and n represent average numbers of repeat units in the chain, and m=68 and n=40. PC-1 was not endcapped. The benzyl protected polymer was then dissolved in EtOAc (40 mL) along with suspended Pd/C (0.1 g, 10%). The reaction vessel was then pressurized to 45 atm H₂ and reacted for 16 hours. The insoluble materials were filtered and all volatiles removed by evaporation (0.94 g, 82%). The resulting PC-1 polymer contained an average of 42 hydroxyl groups (ROP initiating sites).

III. Ring Opening Polymerizations (ROP) Using Polyol Initiators and Electrophilic Cyclic Carbonate Monomer MTCOBnCl.
Example 14. Preparation of Electrophilic Star Polymer ES-1 by ROP Initiated with G-1(OH)$_8$
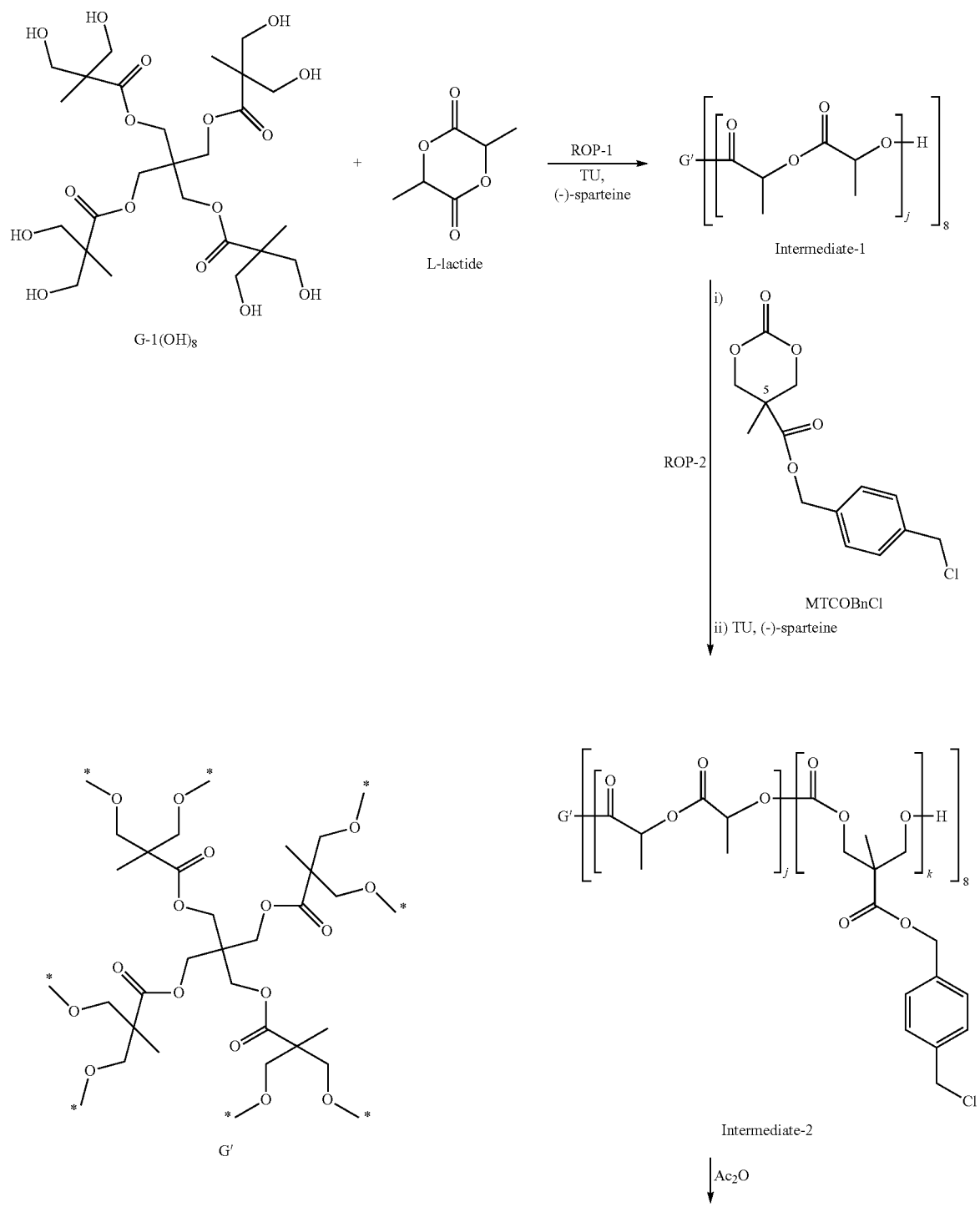

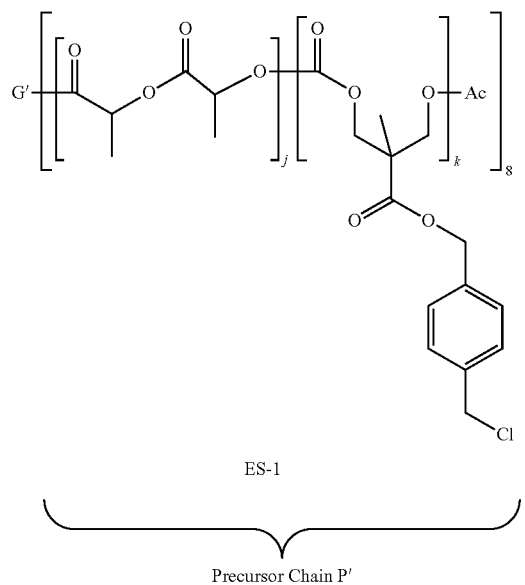

ES-1

Precursor Chain P'

In the above structure for ES-1, j and k represent average numbers of repeat units per chain, and j=20 and k=30. The electrophilic star polymer ES-1 was synthesized in a N2 filled glovebox by first dissolving the G-1(OH)$_8$ (0.04 g, 0.065 mmol) in DMSO (0.15 mL). To this solution was added TU (0.1 g, 0.5 mmoles) and (−)-sparteine (0.1 g, 0.4 mmoles). Separately, a solution of L-lactide monomer (1.5 g, 10.4 mmol, MW 144.13) in DCM (6 mL) was added slowly to the initiator/catalyst solution at 25° C. careful to maintain homogeneity. The reaction mixture was then precipitated into 2-propanol and dried under vacuum to yield 1.5 g (97%) white polymer. The second block was installed by dissolving the previous polymer (0.05 g, 0.00052 mmol) in DCM (1 mL) along with TU (0.03 g, 0.08 mmol) and MTCOBnCl monomer (0.15 g, 0.5 mmol) in a vial. The polymerization was initiated by the addition of (−)-sparteine (0.015 g, 0.06 mmol). Upon complete conversion acetyl chloride (0.05 g, 0.6 mmol) was added and the product polymer was precipitated into cold 2-propanol yielding 0.18 g (84%) white amorphous material. Mn=124 kDa; PDI=1.04.

Each of the hydroxy groups in the G-1(OH)$_8$ structure can act as an initiating site for ring opening polymerization. Sequential ring opening polymerization of L-lactide (ROP-1) initiated by G-1(OH)$_8$ produced Intermediate-1 having a living chain end, which is capable of initiating a second ring opening polymerization of MTCOBnCl (ROP-2), thereby producing Intermediate-2, also having a living end unit. Intermediate-2 was endcapped using acetic anhydride to form electrophilic star polymer ES-1. The brackets subtended by 8 in the structure of ES-1 indicate there are 8 block copolymer chains (arms) linked to the G' core. Each of the starred bonds in G' represents an attachment point of a block copolymer chain to a residual oxygen of a ROP initiator group of G-1(OH)$_8$. The inner block of the block copolymer chain, which is linked directly to the G' core, is a polyester homopolymer block (poly(L-lactide)) derived from L-lactide. The peripheral block linked to the poly(L-lactide) block is a polycarbonate homopolymer block derived from MTCOBnCl.

ES-2 and ES-3 were prepared by a ROP polymerization initiated by G-2(OH)$_{16}$ and G-3(OH)$_{32}$, respectively, according to the above-described procedure for the preparation of ES-1, adjusted for differences in the number of initiating sites.

Example 15. Preparation of Electrophilic Precursor Star Polymer ES-2 from G-2(OH)$_{16}$

G''

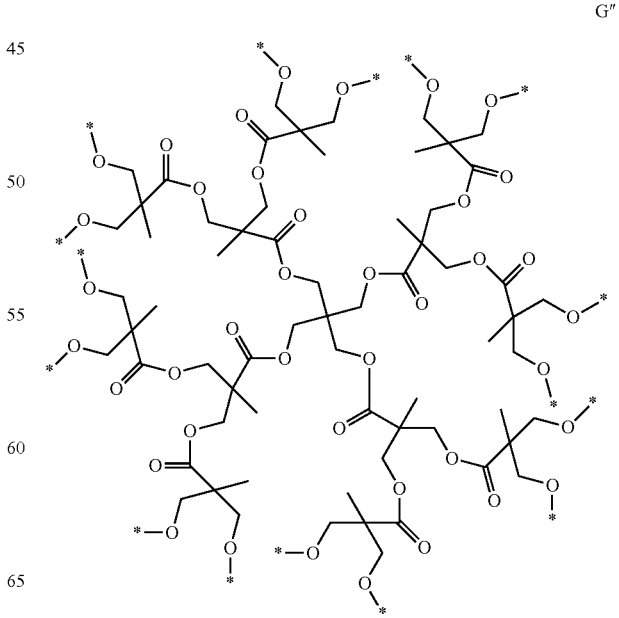

-continued

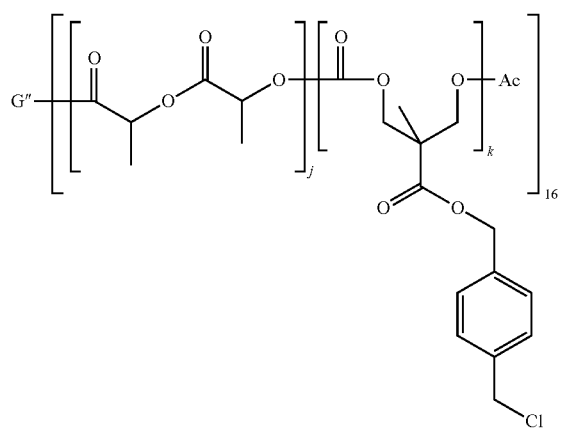

ES-2

In the above structure for ES-2, j=20 and k=30. ES-2 was synthesized according to the same procedure as ES-1 adjusting only for the increased number of polymer arms. G-2 (OH)$_{16}$ (0.05 g, 0.0033 mmol was dissolved in DMSO (0.15 mL). To this solution was added TU (0.1 g, 0.5 mmol) and (−)-sparteine (0.1 g, 0.4 mmol). Separately, a solution of L-lactide monomer (1.5 g, 10.4 mmol) in dichloromethane (DCM) (6 mL) was added slowly to the initiator/catalyst solution at 25° C. careful to maintain homogeneity. The reaction mixture was then precipitated into 2-propanol and dried under vacuum to yield 1.5 g (97%) white polymer. The second block was installed by dissolving the previous polymer (0.05 g, 0.00026 mmol) in DCM (1 mL) along with TU (0.03 g, 0.08 mmol) and MTCOBnCl monomer (0.15 g, 0.5 mmol) in a vial. The polymerization was initiated by the addition of (−)-sparteine (0.015 g, 0.06 mmol). Upon complete conversion acetyl chloride (0.05 g, 0.6 mmol) was added and the product polymer was precipitated into cold 2-propanol yielding 0.18 g (90%) white amorphous material. Mn=174 kDa; PDI=1.04. The brackets subtended by 16 in the structure of ES-2 indicate there are 16 block copolymer chains (arms) linked to the G" core.

Example 16. Preparation of Electrophilic Precursor Star Polymer ES-3 from G-3(OH)$_{32}$

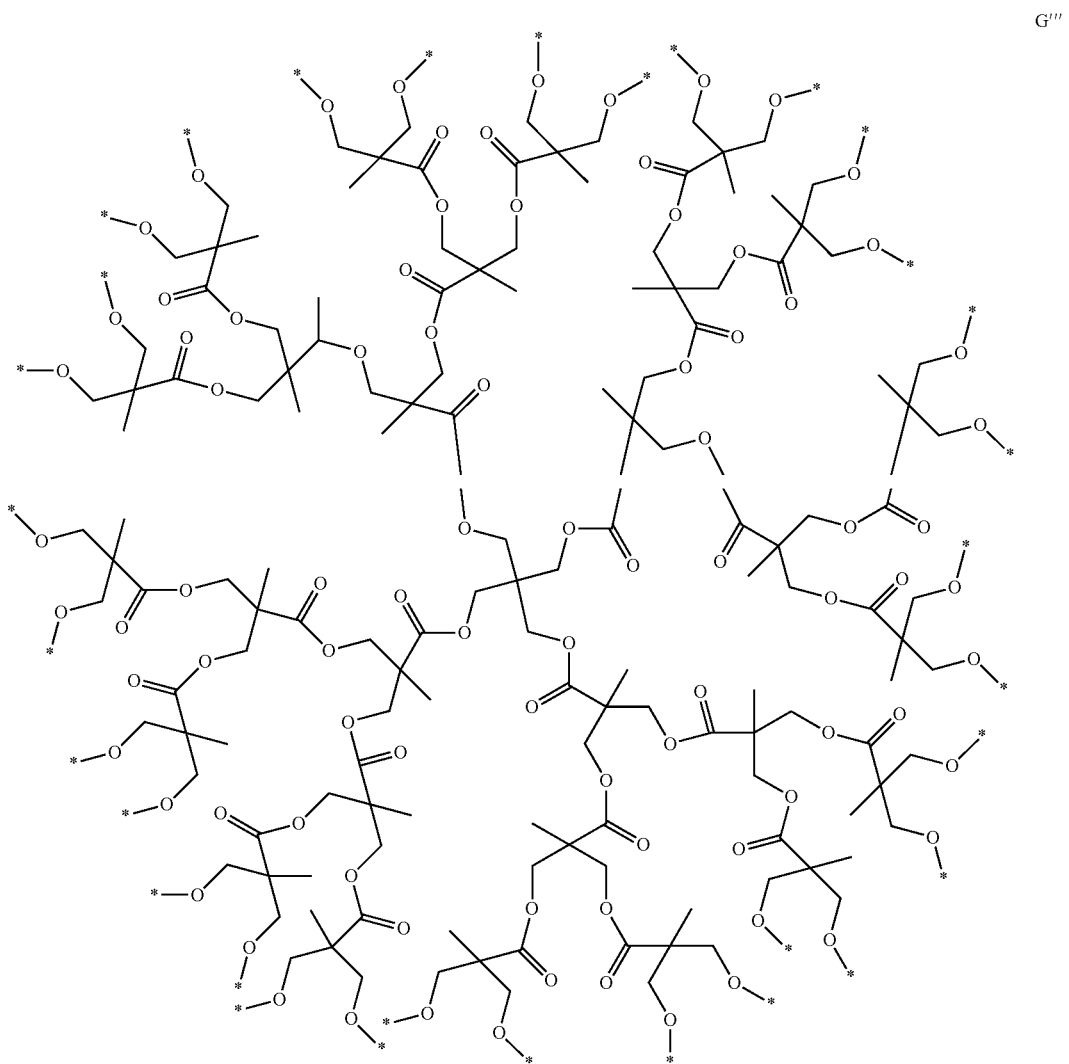

G'''

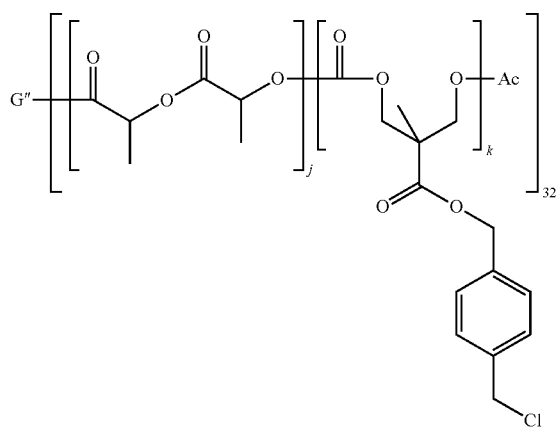

In the above structure for ES-3, j=20 and k=30. ES-3 was synthesized according to the same procedure as ES-1 adjusting only for the increased number of polymer arms. G-3 (OH)$_{32}$ (0.056 g, 0.0016 mmol) was dissolved in DMSO (0.15 mL). To this solution was added TU (0.1 g, 0.5 mmol) and (−)-sparteine (0.1 g, 0.4 mmol). Separately, a solution of L-lactide monomer (1.5 g, 10.4 mmol) in DCM (6 mL) was added slowly to the initiator/catalyst solution at 25° C. careful to maintain homogeneity. The reaction mixture was then precipitated into 2-propanol and dried under vacuum to yield 1.4 g (90%) white polymer. The second block was installed by dissolving the previous polymer (0.05 g, 0.00013 mmol) in DCM (1 mL) along with TU (0.03 g, 0.08 mmol) and MTCOBnCl monomer (0.15 g, 0.5 mmol) in a vial. The polymerization was initiated by the addition of (−)-sparteine (0.015 g, 0.06 mmol). Upon complete conversion acetyl chloride (0.05 g, 0.6 mmol) was added and the product polymer was precipitated into cold 2-propanol yielding 0.17 g (85%) white amorphous material. Mn=174 kDa; PDI=1.04. The brackets subtended by 32 in the structure of ES-3 indicate there are 32 block copolymer chains (arms) linked to the G''' core.

Example 17. Preparation of Electrophilic Graft Polymer EG-1

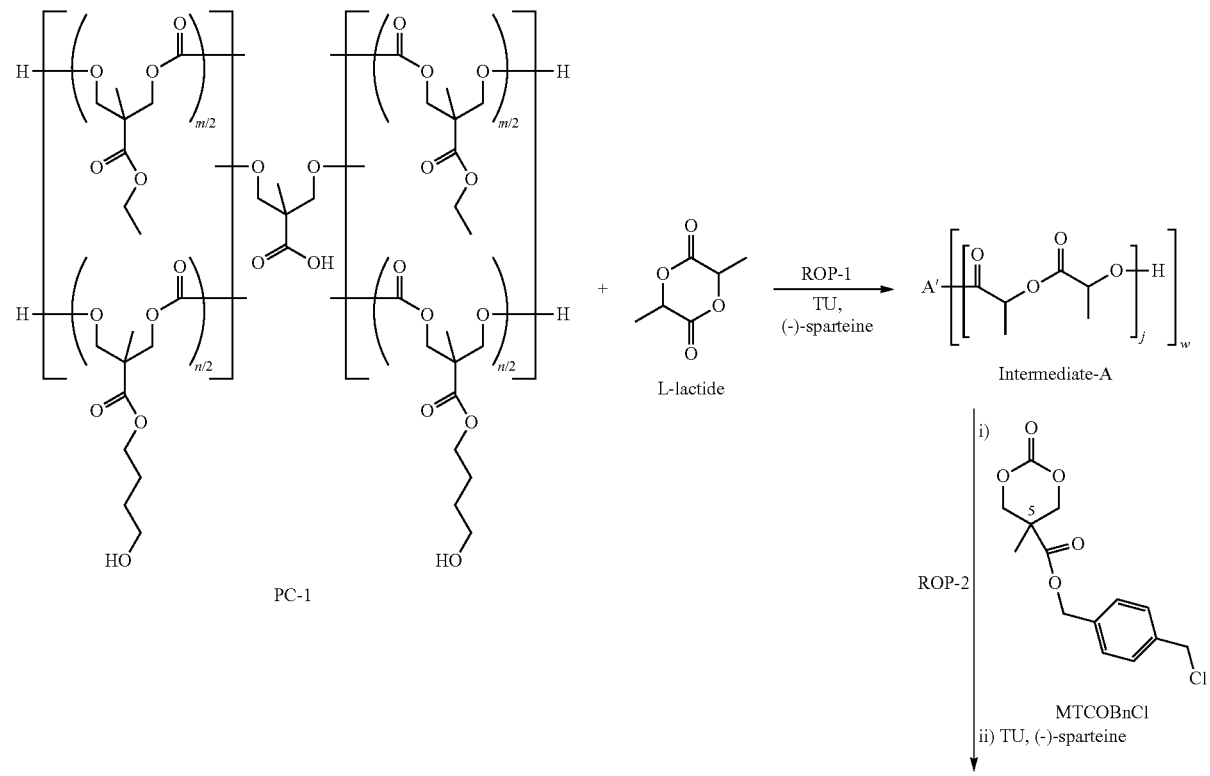

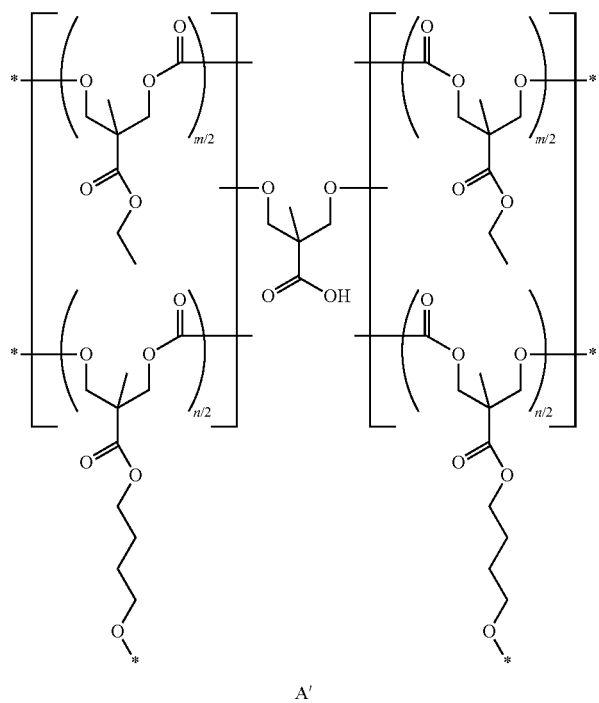

A'

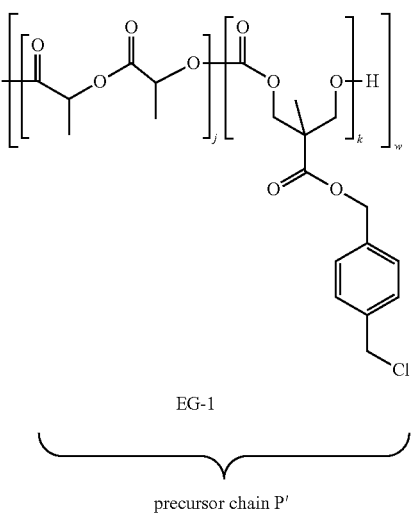

EG-1 precursor chain P'

In the above structure for EG-1, w=42 (the average number of ROP initiator sites per PC-1 molecule), m=68, n=40, j=9 and k=28 in the above structure. The brackets subtended by w in the structure of EG-1 indicate there are w=42 block copolymer chains (arms) independently linked to core structure A'. The initiator PC-1 was not endcapped. That is, the terminal hydroxy groups of PC-1 are capable of initiating a ring opening polymerization, in addition to each side chain hydroxy group. Consequently, in EG-1 and other structures described below w is not necessarily equal to n in PC-1. As shown, two sequential ring opening polymerizations were conducted using L-lactide (ROP-1) and MTCOBnCl (ROP-2). The starred bonds in core structure A' represents attachment points for the block copolymer chain. In this instance, the inner block directly linked to A' group is a poly(L-lactide) homopolymer block. The peripheral block is a polycarbonate homopolymer block derived from MTCOBnCl. EG-1 was not endcapped.

The preparation of EG-1 was as follows. PC-1 (0.05 g, 0.004 mmol), L-lactide (0.12 g, 0.83 mmol), TU (0.03 g, 0.07 mmol) and DCM (0.7 mL) were added to a vial. (−)-Sparteine (0.015 g, 0.06 mmol) was then added to initiate the polymerization. Upon full conversion, the reaction mixture was precipitated into 2-propanol and dried yielding 0.15 g (89%) white polymer. A portion of this material (0.05 g, 0.0007 mmol) was combined with MTCOBnCl (0.27 g, 0.9 mmol), TU (0.04 g, 0.1 mmol) and DCM (0.6 mL). The polymerization was then initiated by adding (−)-sparteine (0.04 g, 0.17 mmol). Upon full conversion the reaction mixture was precipitated into 2-propanol yielding 0.29 g (90%).

The following preparation of EG-2 utilized PC-1 to initiate a single ROP polymerization of cyclic carbonate monomer MTCOBnCl. The resulting electrophilic graft polymer EG-2 comprises a pendant polycarbonate homopolymer chain directly linked to core structure A'.

Example 18. Preparation of Electrophilic Graft Polymer EG-2 Having Core Structure a' Shown Above

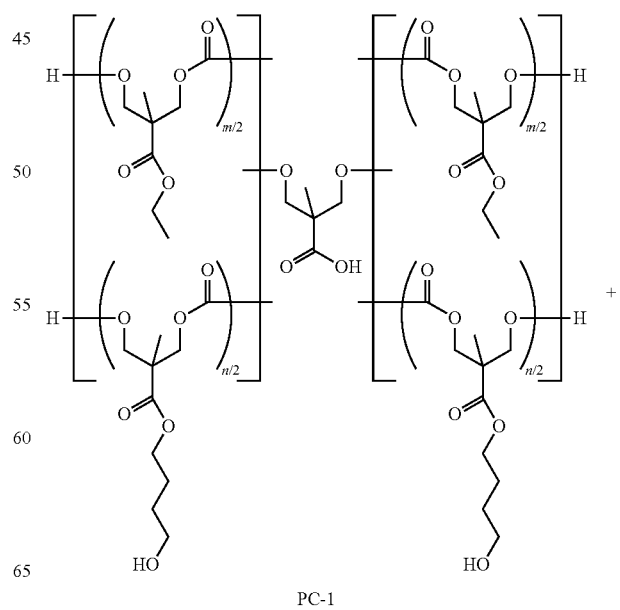

PC-1

-continued

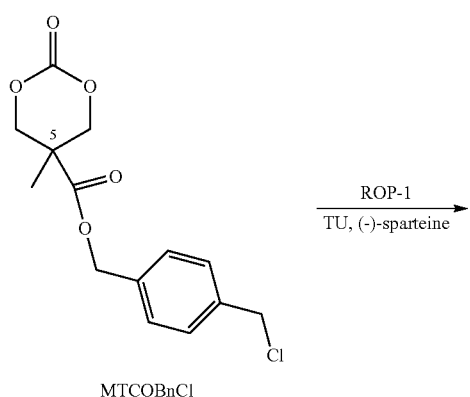

MTCOBnCl

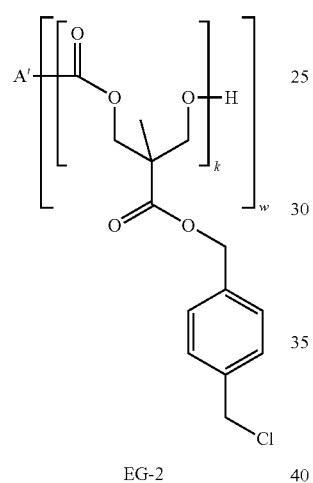

EG-2

In the structure above for EG-2, m=68, n=40, k=9, and w=42 (the average number of ROP initiating sites on PC-1). The brackets subtended by w in the structure of EG-2 indicate there are w=42 polycarbonate chains (arms) independently linked to core structure A' (see Example 17). The starred bonds in core structure A' represents attachment points for the polycarbonate chains. EG-2 was prepared as follows. A vial was charged with PC-1 (0.05 g, 0.004 mmol), MTCOBnCl (0.26 g, 0.83 mmol), TU (0.04 g, 0.1 mmol) and DCM (0.6 mL). The polymerization was then initiated with the addition of sparteine (0.4 g, 0.17 mmol). Upon full conversion the reaction mixture was precipitated into 2-propanol yielding a white polymer, EG-2.

The following preparation of electrophilic graft polymer EG-3 utilized PC-1 to initiate a single ROP polymerization of cyclic carbonate monomer MTCOPrCl. As in EG-2, EG-3 comprises a pendant polycarbonate homopolymer chain directly linked to core structure A'.

Example 19. Preparation of Electrophilic Graft Polymer EG-3 Having Core Structure A'

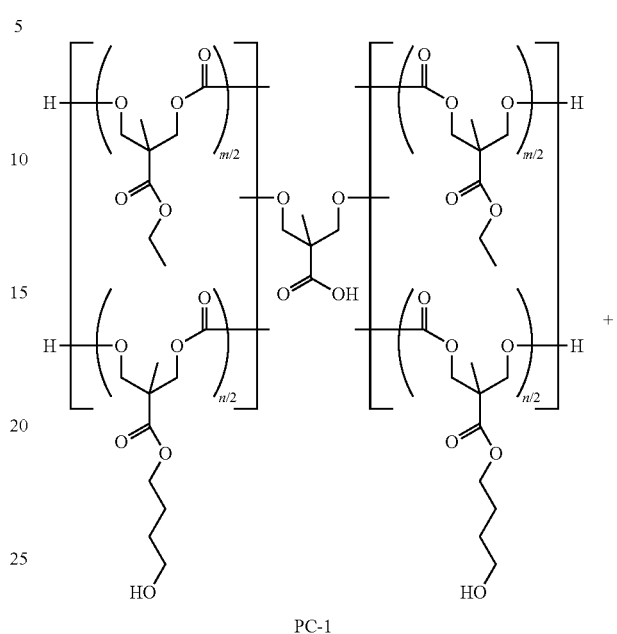

PC-1

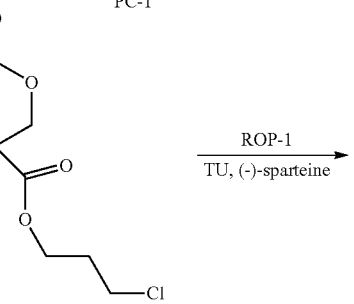

MTCOPrCl

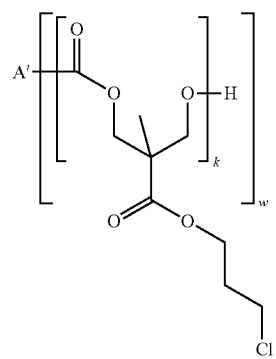

EG-3

In the structure above for EG-3, m=68, n=40, k=9, and w=42 (the average number of ROP initiating sites in PC-1). EG-3 was prepared as follows. The brackets subtended by w in the structure of EG-3 indicate there are w=42 polycarbonate chains (arms) independently linked to core structure A' (see Example 17). The starred bonds in core structure A' represents attachment points for the polycarbonate chains. The polymer was synthesized by charging a vial with PC-1 (0.05 g, 0.004 mmol), MTCOPrCl (0.20 g, 0.83 mmol), TU (0.04 g, 0.1 mmol) and DCM (0.6 mL). The polymerization was then initiated with the addition of sparteine (0.4 g, 0.17 mmol). Upon full conversion the reaction mixture was precipitated into 2-propanol yielding a white polymer, EG-3.

The following electrophilic linear polycarbonate copolymer, EL-1, was formed by ROP polymerization of a mixture of trimethylene carbonate (TMC) and MTCOBnCl initiated by pyrene butanol (PBOH).

Example 20. Preparation of Electrophilic Linear Random Polycarbonate Copolymer EL-1

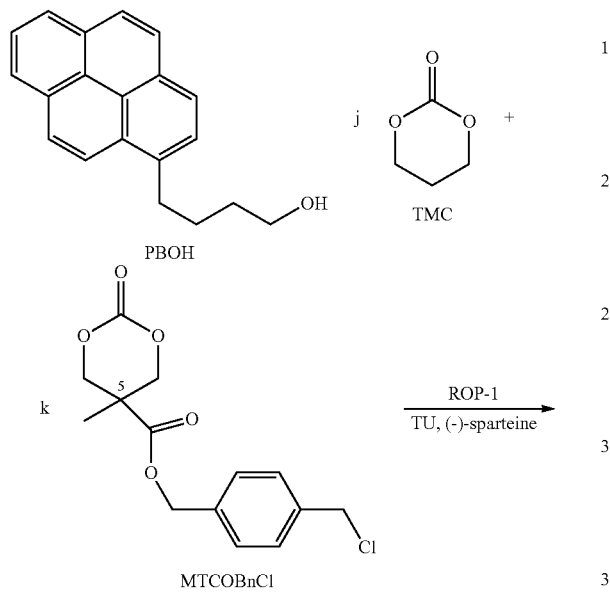

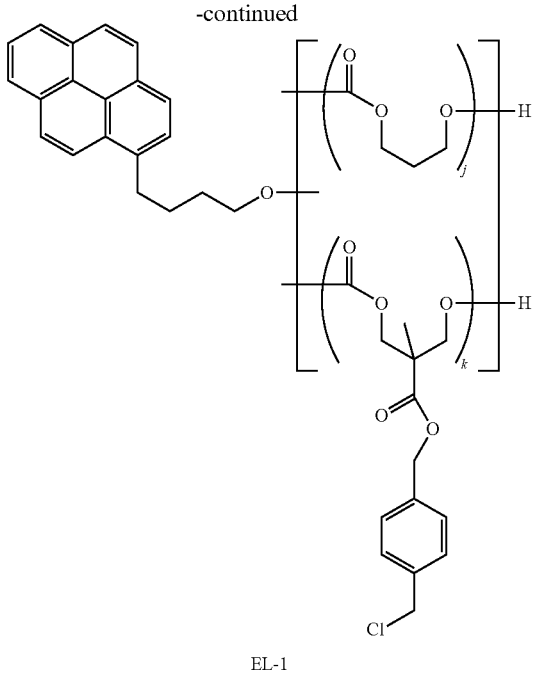

In the structure of EL-1, j=30, and k=10. EL-1 was prepared as follows: PBOH (0.045 g, 0.163 mmol), TMC (0.5 g, 4.9 mmol), MTCOBnCl (0.487 g, 1.63 mmol), TU (0.06 g, 0.163 mmol) and DCM (3 mL) were added to a vial. The polymerization was then initiated by adding (−)-sparteine (0.04 g, 0.163 mmol). Upon full conversion the reaction mixture was precipitated into MeOH yielding 0.93 g (90%).

Example 21. Preparation of Electrophilic Graft Polymer EG-4 Having Core Structure A'

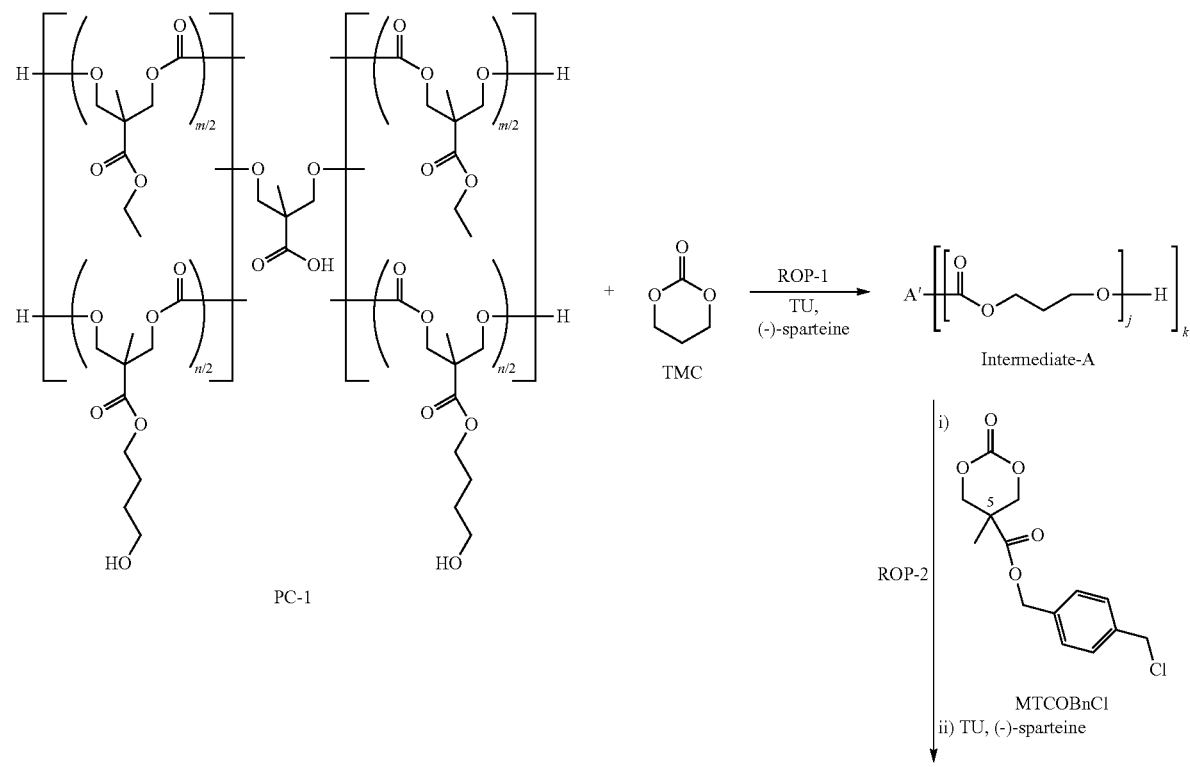

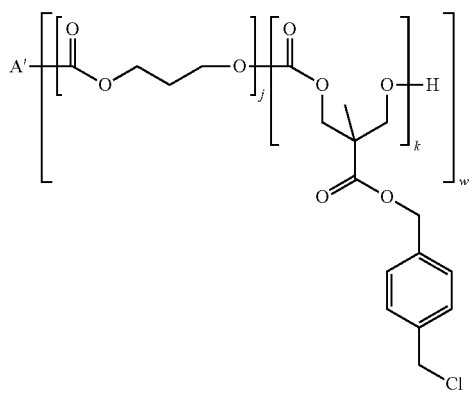

EG-4

In the above structure of EG-4, w=42 (the average number of ROP initiating sites in PC-1), m=68, n=40, j=9, and k=14. A' has the structure shown in Example 17. EG-4 was prepared by the procedure used in EG-1, substituting L-lactide with trimethylene carbonate (TMC). A vial was charged with PC-1 (0.05 g, 0.004 mmol), TMC (0.084 g, 0.83 mmol), TU (0.04 g, 0.1 mmol) and DCM (0.6 mL). The polymerization was then initiated with the addition of (−)-sparteine (0.4 g, 0.17 mmol). Upon full conversion the reaction mixture was precipitated into 2-propanol yielding a white polymer. This polymer was redissolved in DCM (1 mL) along with MTCOBnCl (0.747 g, 2.49 mmol) and TU (0.04 g, 0.1 mmol). The polymerization was then initiated by adding (−)-sparteine (0.45 g, 0.19 mmol). Upon full conversion the reaction mixture was precipitated into 2-propanol yielding 0.68 g (77%) white polymer.

The electrophilic polymers are summarized in Table 12.

dissolved in acetonitrile. The vial was then cooled to −78° C. and TMA gas was added. The vial was then warmed to room temperature and allowed to stir overnight. The reaction mixture was then precipitated into diethyl ether.

General procedure for quaternization with N,N,N',N'-tetramethylethylenediamine (TMEDA) and N,N-dimethylethanolamine (DMEA). Electrophilic polymer was added to a vial and dissolved in MeCN. To the vial was added TMEDA. The vial was then allowed to stir overnight at room temperature. The reaction mixture was precipitated into diethyl ether.

General procedure for quaternization with N,N-dimethylethanolamine (DMEA). Electrophilic polymer was added to a vial and dissolved in MeCN. To the vial was added DMEA. The vial was then allowed to stir overnight at room temperature. The reaction mixture was precipitated into diethyl ether.

TABLE 12

| Electrophilic Polymer | Core | Type | Initiator | ROP-1 Monomer(s) | ROP-2 Monomer | j (mol %) | k (mol %) |
|---|---|---|---|---|---|---|---|
| ES-1 | G' | star | G-1(OH)$_8$ | L-Lactide | MTCOBnCl | 20 (40%) | 30 (60%) |
| ES-2 | G'' | star | G-2(OH)$_{16}$ | L-Lactide | MTCOBnCl | 20 (40%) | 30 (60%) |
| ES-3 | G''' | star | G-3(OH)$_{32}$ | L-Lactide | MTCOBnCl | 20 (40%) | 30 (60%) |
| EG-1 | A' | graft | PC-1 | L-Lactide | MTCOBnCl | 9 (24.3%) | 28 (76.7%) |
| EG-2 | A' | graft | PC-1 | MTCOBnCl | | 0 | 9 (100%) |
| EG-3 | A' | graft | PC-1 | MTCOPrCl | | 0 | 9 (100%) |
| EG-4 | A' | graft | PC-1 | TMC | MTCOBnCl | 9 (40%) | 14 (60%) |
| EL-1 | none | linear | PBOH | TMC/ MTCOBnCl | | 30 (75%) (TMC) | 10 (25%) MTCOBnCl |

IV. Quaternization Reactions.

General procedure for quaternization with trimethylamine (TMA). The electrophilic polymer was added to a vial and In the following structures, G', G'', and G''' have the structures shown in Examples 14, 15, and 16, respectively. A' has the structure shown in Example 17.

Example 22. Preparation of Cationic Star Polymer CS-1 Having Core Structure G'

Example 24. Preparation of Cationic Star Polymer CS-3 Having Core Structure G'''

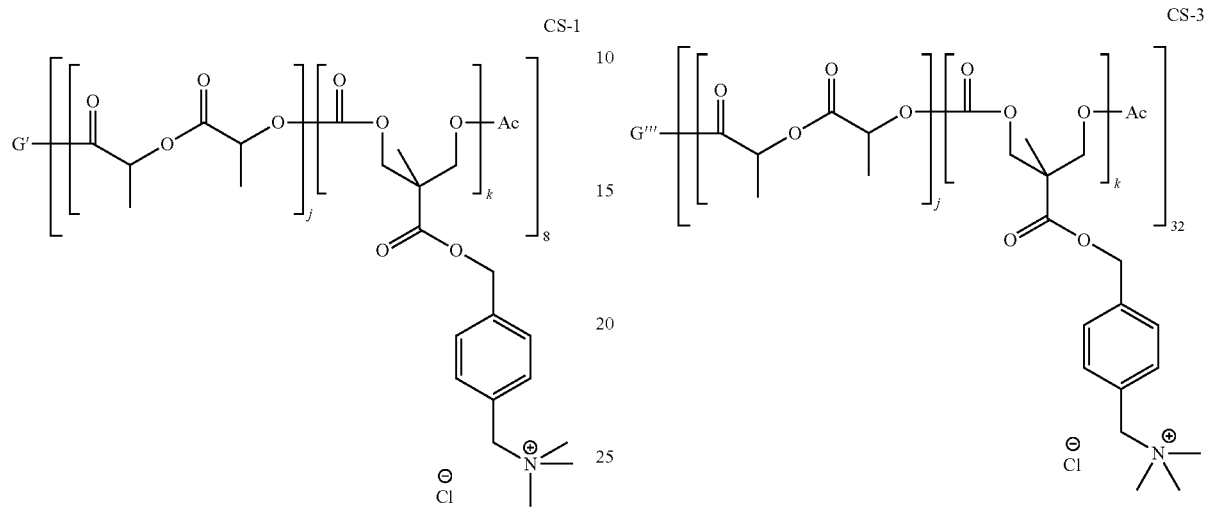

Following the general procedure described above ES-1 was quaternized using TMA, resulting in cationic star polymer CS-1 shown above. In the above structure of CS-1, j=20 and k=30.

Example 23. Preparation of Cationic Star Polymer CS-2 Having Core Structure G"

Following the general procedure described above, electrophilic star polymer ES-3 was quaternized using TMA to produce cationic star polymer CS-3 shown above. In the above structure of CS-3, j=20 and k=30.

Example 25. Preparation of Cationic Graft Polymer CG-1 Having Core Structure A'

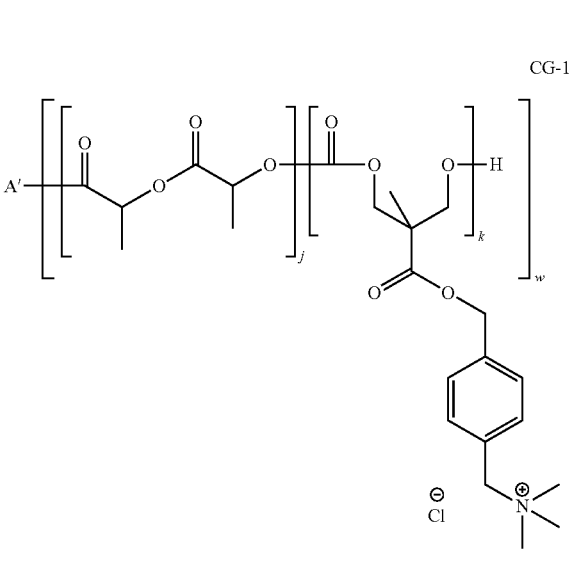

Following the general quaternization procedure described above, electrophilic star polymer ES-2 was quaternized using TMA to produce cationic star polymer CS-2 shown above. In the above structure of CS-2, j=20 and k=30.

Following the general procedure described above, electrophilic graft polymer EG-1 was quaternized using TMA to form cationic graft polymer CG-1 shown above. In the above structure of CG-1, w=42, j=10, k=30. In A' of CG-1, m=68 and n=40.

Example 26. Preparation of Cationic Graft Polymer CG-2 Having Core Structure A'

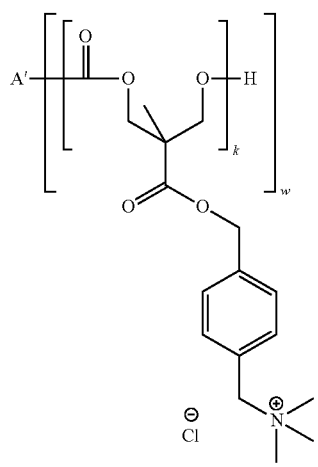

CG-2

Following the general procedure described above, electrophilic graft polymer EG-2 was quaternized using TMA, resulting in cationic graft polymer CG-2 shown above. In the above structure of CG-2, w=42, and k=10. In A' of CG-2, m=68 and n=40.

Example 27. Comparative

Preparation of Cationic Graft Polymer CG-3 Having Core Structure A'

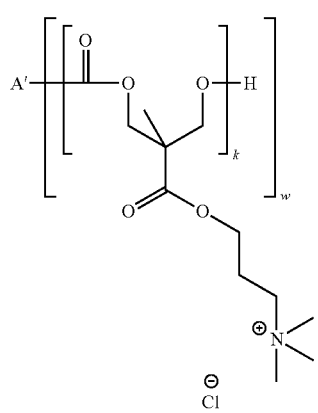

CG-3

Following the general procedure described above, electrophilic graft polymer EG-3 was quaternized using TMA, resulting in cationic graft polymer CG-3 shown above. In the above structure of CG-3, w=42 and k=10. In A' of CG-3, m=68 and n=40.

Example 28. Comparative

Preparation of Cationic Linear Random Copolymer CL-1

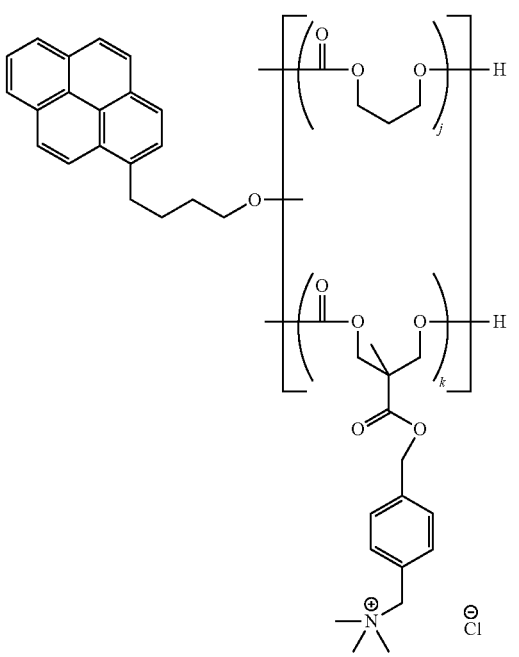

CL-1

Following the general procedure described above, electrophilic linear random polymer EL-1 was quaternized using TMA to form cationic linear random copolymer CL-1. In the above structure of CL-1, j=28.5 (3100 kDa) and k=6.8 (2340 kDa).

Example 29. Preparation of Cationic Star Polymer CS-4 Having Core Structure G'

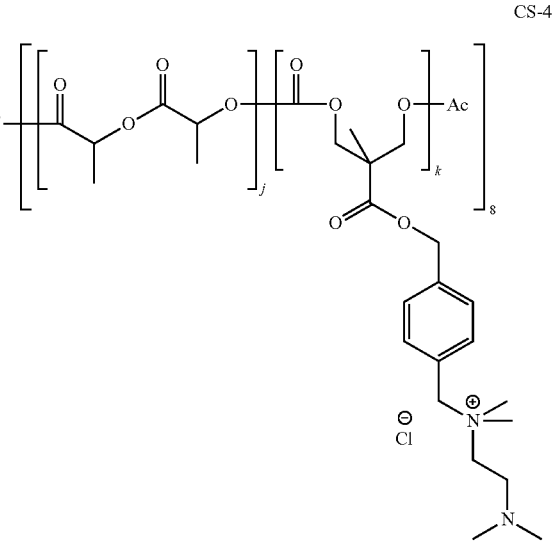

CS-4

Following the general procedure described above, ES-1 was quaternized using TMEDA, resulting in cationic star polymer CS-4 shown above. In the above structure of CS-4, j=20 and k=30.

Example 30. Preparation of Cationic Star Polymer CS-5 Having Core Structure G″

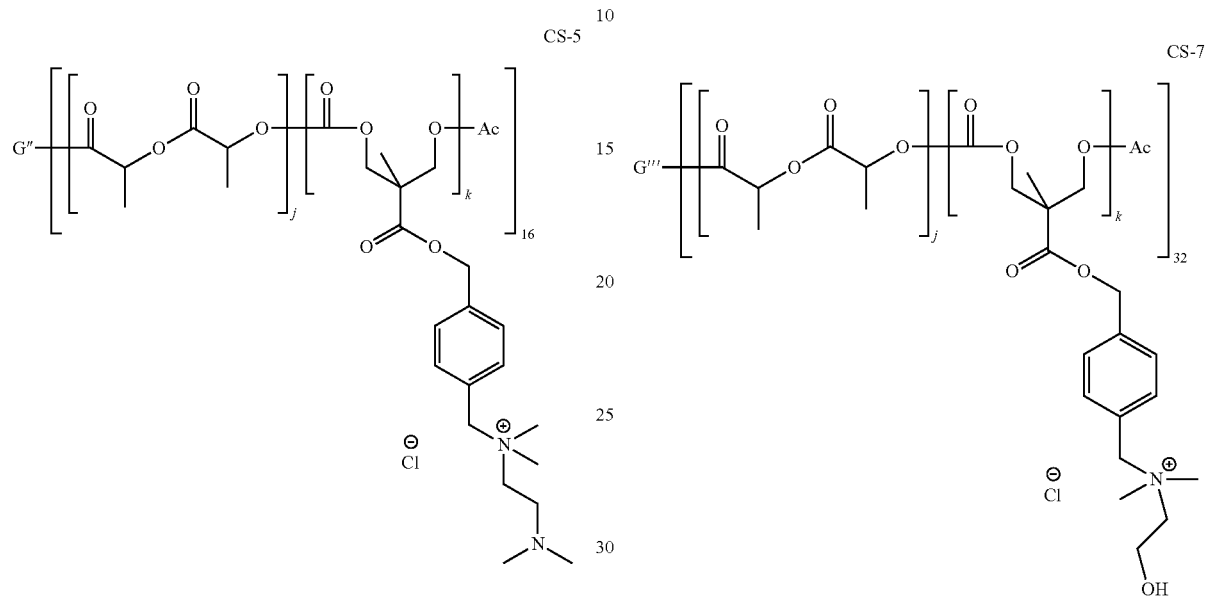

Following the general procedure described above, electrophilic star polymer ES-2 was quaternized using TMEDA, resulting in cationic star polymer CS-5 shown above. In the above structure of CS-5, j=20 and k=30.

Example 31. Preparation of Cationic Star Polymer CS-6 Having Core Structure G‴

Following the general procedure described above, electrophilic star polymer ES-3 was quaternized using TMEDA, resulting in cationic star polymer CS-6 shown above. In the above structure of CS-6, j=20 and k=30.

Example 32. Preparation of Cationic Star Polymer CS-7 Having Core Structure G‴ Shown Above The procedure for Example 10 was repeated using N,N-dimethylethanolamine for the quaternization, resulting in cationic star polymer CS-7 shown above. In the above structure of CS-7, j=20 and k=30.

Example 33. Preparation of Cationic Graft Polymer CG-4 Having Core Structure A′

Electrophilic graft polymer EG-4 was quaternized using TMA using the general procedure described above to prepare cationic graft polymer CG-4 shown above. In the above structure of CG-4, w=42, j=10, and k=30. In A' of CG-4, m=68 and n=40.

Example 34. Preparation of Cationic Graft Polymer CG-5 Having Core Structure A' Shown Above

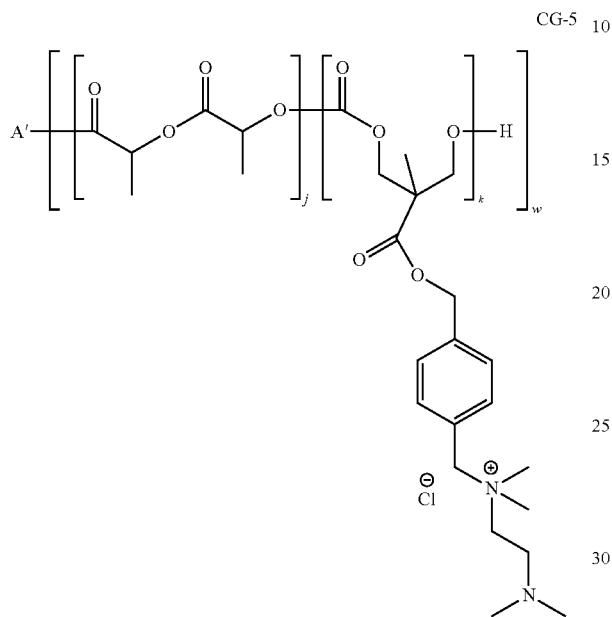

CG-5

Using the general procedure described above, electrophilic graft polymer EG-1 was quaternized using TMEDA to form cationic graft polymer CG-5 shown above. In the above structure of CG-5, w=42, j=10 and k=30. In A' of CG-5, m=68 and n=40.

Example 35. Preparation of Cationic Graft Polymer CG-6 Having Core Structure A' Shown Above

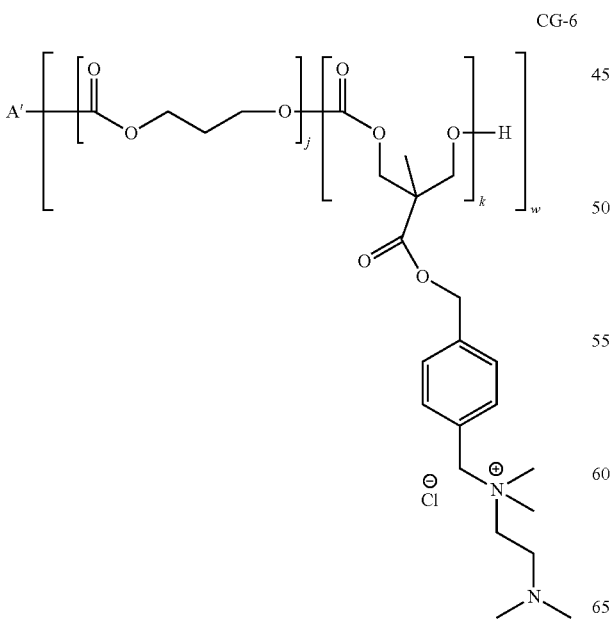

CG-6

Using the general procedure described above, electrophilic graft polymer EG-4 was quaternized using TMEDA to form cationic graft polymer CG-6 shown above. In the above structure of CG-6, w=42, j=10, and k=30. In A' of CG-6, m=68 and n=40.

Example 36. Preparation of Cationic Graft Polymer CG-7 Having Core Structure A' Shown Above

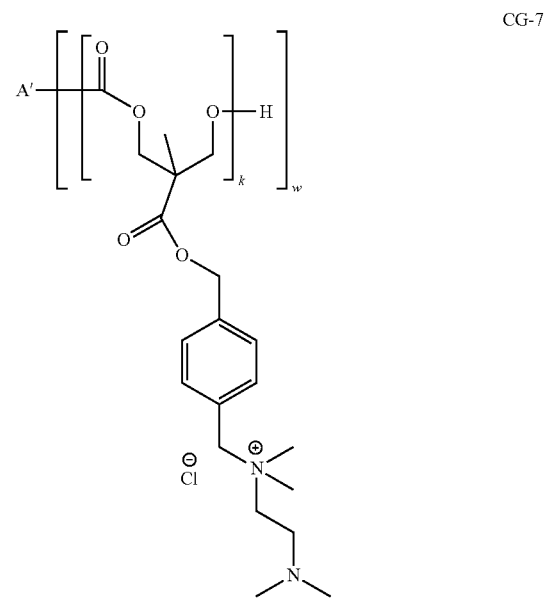

CG-7

Using the general procedure described above, electrophilic graft polymer EG-2 was quaternized using TMEDA to form cationic graft polymer CG-7 shown above. In the above structure of CG-7, w=42 and k=30. In A' of CG-7, m=68 and n=40.

The cationic polymers are summarized in Table 13. In each Example except Comparative Example 27 the quaternary nitrogen is directly covalently linked to a methylene group of a side chain benzyl moiety. That is, the quaternary nitrogen is indirectly covalently linked to the polymer backbone through the side chain benzyl group.

TABLE 13

| Example | Cationic Polymer | Core | Type | Initiator | ROP-1 Monomer | ROP-2 Monomer | Amine |
|---|---|---|---|---|---|---|---|
| 22 | CS-1 | G' | star | G-1(OH)$_8$ | L-Lactide | MTCOBnCl | TMA |
| 23 | CS-2 | G" | star | G-2(OH)$_{16}$ | L-Lactide | MTCOBnCl | TMA |
| 24 | CS-3 | G''' | star | G-3(OH)$_{32}$ | L-Lactide | MTCOBnCl | TMA |
| 25 | CG-1 | A' | graft | PC-1 | L-Lactide | MTCOBnCl | TMA |
| 26 | CG-2 | A' | graft | PC-1 | MTCOBnCl | | TMA |
| 27 (comp.) | CG-3 | A' | graft | PC-1 | MTCOPrCl | | TMA |
| 28 | CL-1 | | linear | PBOH | TMC/MTCOBnCl | | TMA |
| 29 | CS-4 | G' | star | G-1(OH)$_8$ | L-Lactide | MTCOBnCl | TMEDA |
| 30 | CS-5 | G" | star | G-2(OH)$_{16}$ | L-Lactide | MTCOBnCl | TMEDA |
| 31 | CS-6 | G''' | star | G-3(OH)$_{32}$ | L-Lactide | MTCOBnCl | TMEDA |
| 32 | CS-7 | G''' | star | G-3(OH)$_{32}$ | L-Lactide | MTCOBnCl | DMEA |
| 33 | CG-4 | A' | graft | PC-1 | TMC | MTCOBnCl | TMA |
| 34 | CG-5 | A' | graft | PC-1 | L-Lactide | MTCOBnCl | TMEDA |
| 35 | CG-6 | A' | graft | PC-1 | TMC | MTCOBnCl | TMEDA |
| 36 | CG-7 | A' | graft | PC-1 | MTCOBnCl | | TMEDA |

V. Minimal Inhibitory Concentration (MIC) measurements.

*Staphylococcus aureus* (*S. aureus*), *Escherichia coli* (*E. coli*), *Bacillus subtilis*, and *Pseudomonas aeruginosa* (*P. aeruginosa*) obtained from ATCC were re-constituted from the lyophilized form according to the manufacturer's protocol. Bacterial samples were cultured in Tryptic Soy Broth (TSB) solution at 37° C. under constant shaking of 100 rpm. The MICs of the polymers were measured using the broth microdilution method as reported previously. 100 microliters of TSB broth containing a polymer at various concentrations was placed into each well of a 96-well tissue culture plate (TCTP). An equal volume of bacterial suspension (3×10$^6$ CFU/mL) was added into each well. Prior to mixing, the bacterial sample was first inoculated overnight to enter its log growth phase. The concentration of bacterial solution was adjusted to give an initial optical density (O.D.) reading of approximately 0.07 at 600 nm on a microplate reader (TECAN, Switzerland), which corresponds to a cell concentration of 3×10$^8$ CFU/mL in accordance with McFarland turbidity standard 1 solution. The bacterial solution was further diluted by 100-fold to achieve an initial loading of 3×10$^6$ CFU/mL. The 96-well plate was kept in an incubator at 37° C. under constant shaking of 100 rpm for 18 hours. The MIC was taken as the concentration of the antimicrobial polymer at which no microbial growth was observed with unaided eyes and microplate reader (TECAN, Switzerland) at the end of 18 hours incubation. Broth containing microbial cells alone was used as negative control, and each test was carried out in 4 replicates.

MIC data is summarized in Table 14 in units of parts per million (ppm). A lower value indicates greater antimicrobial activity. The term "(comp.)" refers to a comparative example.

TABLE 14

| Ex. | Cationic Polymer | Initiator | ROP-1 Monomer | ROP-2 Monomer | Amine | MIC$^a$ (B. subtilis)$^b$ | MIC$^a$ (S. aureus)$^b$ | MIC$^a$ (E. coli)$^c$ | MIC$^a$ (C. albicans)$^b$ | MIC$^a$ (P. aeruginosa)$^b$ |
|---|---|---|---|---|---|---|---|---|---|---|
| 22 | CS-1 | G-1(OH)$_8$ | L-Lactide | MTCOBnCl | TMA | | 500 | | | |
| 23 | CS-2 | G-2(OH)$_{16}$ | L-Lactide | MTCOBnCl | TMA | | 250 | | | |
| 24 | CS-3 | G-3(OH)$_{32}$ | L-Lactide | MTCOBnCl | TMA | | 125 | 125 | | |
| 25 | CG-1 | PC-1 | L-Lactide | MTCOBnCl | TMA | | 125 | 500 | 63 | >1000 |
| 26 | CG-2 | PC-1 | MTCOBnCl | | TMA | | 250 | 125 | 63 | 500 |
| 27 (comp.) | CG-3 | PC-1 | MTCOPrCl | | TMA | | >1000 | >1000 | 1000 | 1000 |
| 28 (comp.) | CL-1 | PBOH | TMC/MTCOBnCl | | TMA | 500 (8 hr) | >500 (8 hr) | | | |
| 29 | CS-4 | G-1(OH)$_8$ | L-Lactide | MTCOBnCl | TMEDA | | 250 | | | |
| 30 | CS-5 | G-2(OH)$_{16}$ | L-Lactide | MTCOBnCl | TMEDA | | >1000 | | | |
| 31 | CS-6 | G-3(OH)$_{32}$ | L-Lactide | MTCOBnCl | TMEDA | | 500 | 500 | | |
| 32 | CS-7 | G-3(OH)$_{32}$ | L-Lactide | MTCOBnCl | DMEA | | >1000 | >1000 | | |
| 33 | CG-4 | PC-1 | TMC | MTCOBnCl | TMA | | 1000 | >1000 | 63 | >1000 |
| 34 | CG-5 | PC-1 | L-Lactide | MTCOBnCl | TMEDA | | 125 | 500 | 63 | >1000 |
| 35 | CG-6 | PC-1 | TMC | MTCOBnCl | TMEDA | | 250 | >1000 | 63 | >1000 |
| 36 | CG-7 | PC-1 | MTCOBnCl | | TMEDA | | 250 | 125 | 31 | 500 |

$^a$Minimum inhibitory concentration in mg/L: the concentration at which the growth of bacteria is completely inhibited.
$^b$Gram-positive.
$^c$Gram-negative.

The data in Table 14 demonstrate a significant improvement in the antimicrobial activity (indicated by lower MIC values) when the quaternary amine group has benzyl substituent (compare Example 26 (CG-2) with Comparative Example 27 (CG-3)). Further, both graft and star cationic polymers having a benzyl substituted quaternary amine had higher activity against *S. aureus* compared to a linear polymer having a benzyl substituted quaternary amine (compare Examples 24 (CS-3), 26 (CG-2) and 36 (CG-7) with comparative Example 28 (CL-1).

Cationic star polymer Example 24 (CS-3), and cationic graft polymer Examples 26 (CG-2) and 36 (CG-7) prepared from TMA, TMA and TMEDA, respectively, had the strongest antimicrobial activity against *S. aureus* (MIC 125 mg/L to 250 mg/L) and against *E. coli* (MIC 125 mg/L to 250 mg/L).

Comparing the mol % values for j and k in Table 12 with the MIC data in Table 14, chains P' can comprise the cationic repeat unit having a benzyl substituted quaternary amine group in an amount of about 60 mol % to 100 mol %, more preferably 70 mol % to 100 mol %, based on total moles of repeat units in chains P'.

Comparative Examples 37-39

Cationic linear polymers CL-2, CL-3 and CL-4 were prepared according to the described procedures in "ANTIMICROBIAL POLYMERS AND METHODS OF MANUFACTURE THEREOF", published US patent application 2011/0150977 A1 to J. Hedrick, et al., and tested against Gram-negative *E. coli*.

Comparative Example 37

CL-2. a=60.

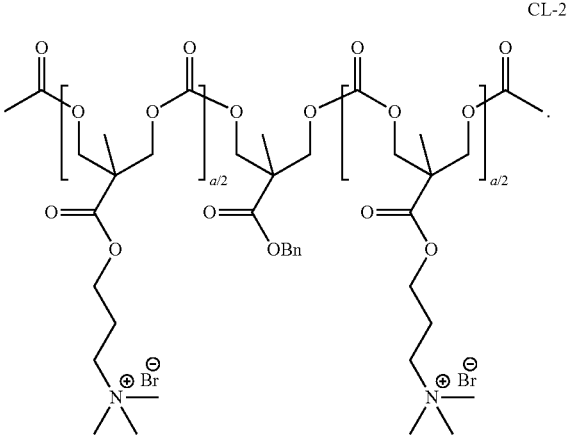

Comparative Example 38

CL-3. a=40, b=60.

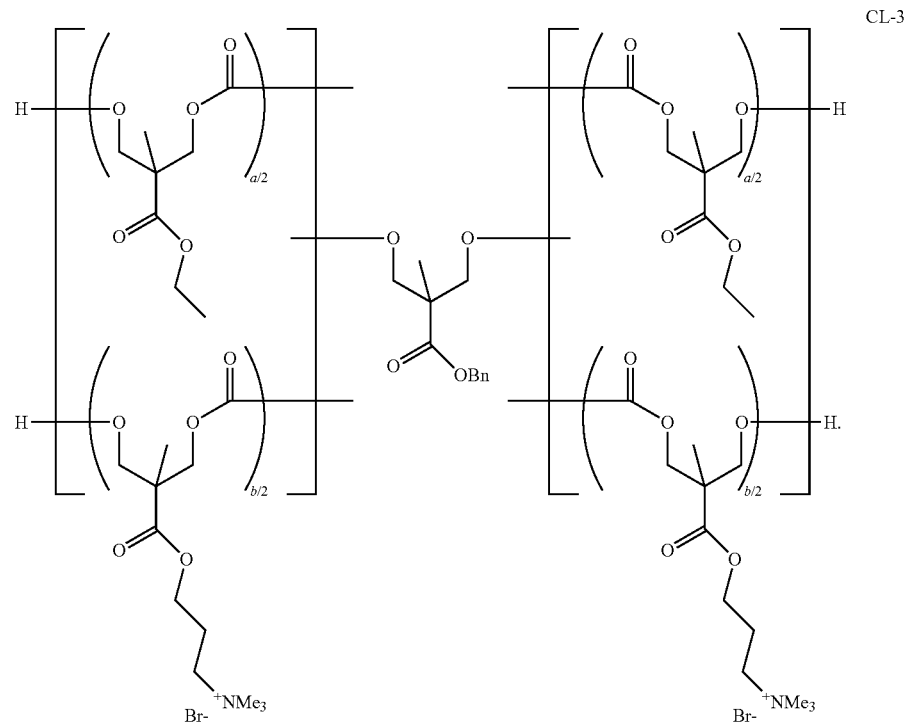

Comparative Example 39

CL-4. Mn=11000; a=2.1, b=10.3, n=10.

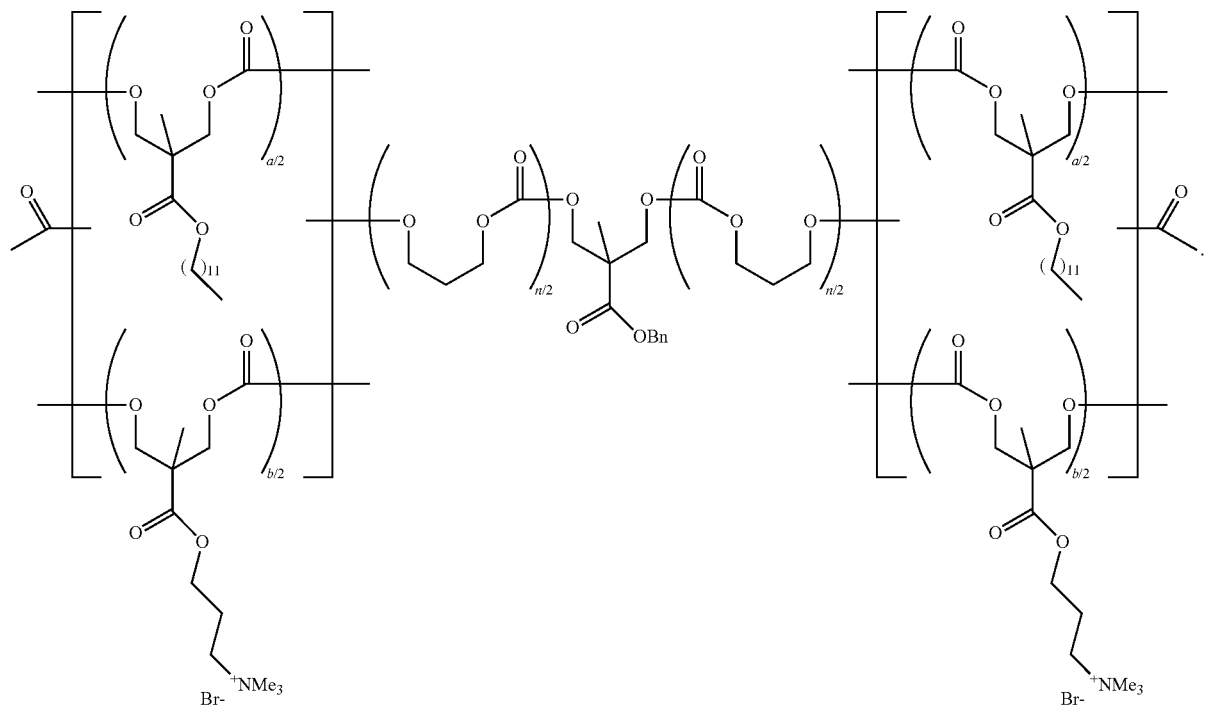

Comparative Example 40

Preparation of CL-5. m=17 (2850 Da), n=3.5 (1190 Da).

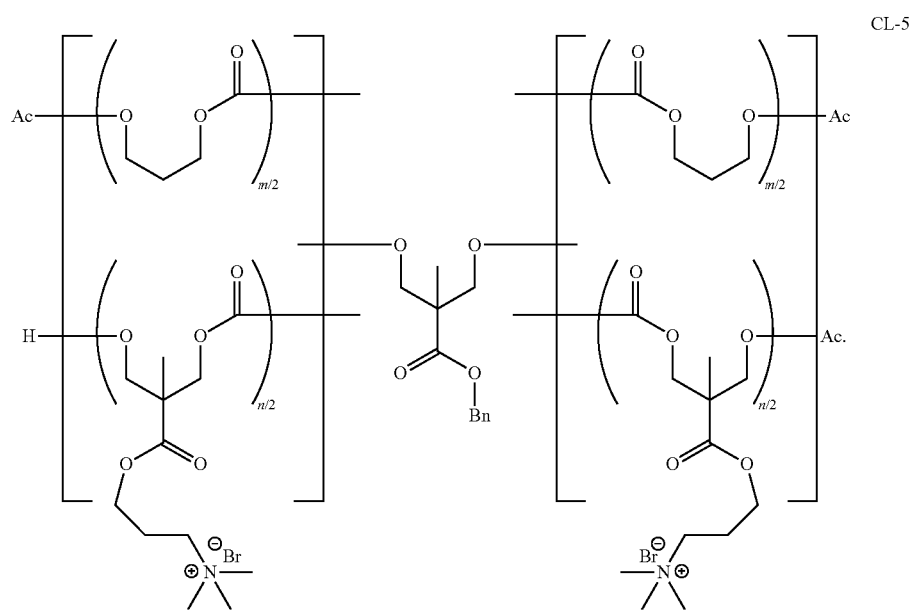

A vial was charged with BnMPA initiator (0.036 g, 0.163 mmol), TMC (0.5 g, 4.9 mmol), MTCOPrBr (0.46 g, 1.63 mmol), TU (0.121 g, 0.32 mmol), DCM (3.0 g) and a stir bar. The polymerization was initiated by the addition of (−)-sparteine (0.077 g, 0.032 mmol) and stirred at ambient temperature. Upon complete monomer conversion the polymer product was endcapped with acetyl chloride and precipitated into cold 2-propanol yielding 0.80 g amorphous polymer. The endcapped intermediate polymer was treated with trimethylamine in acetonitrile followed by stirring at 50° C. for 16 hours to produce CL-5.

Example 41. Preparation of 5-methyl-5-(3-bromopropyl)oxycarboxyl-1,3-dioxan-2-one, (MTCOPrBr), MW 281.10

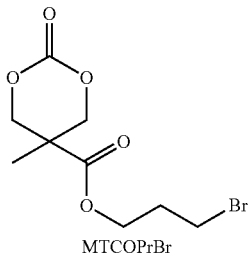

MTCOPrBr

MTCOPrBr was prepared by the procedure of Example 1 on a 45 mmol scale using 3-bromo-1-propanol as the alcohol. The product was purified by column chromatography, and subsequently recrystallized to yield white crystals (6.3 g, 49%). $^1$H NMR (400 MHz, CDCl$_3$): delta 4.69 (d, 2H; CH$_2$OCOO), 4.37 (t, 2H; OCH$_2$), 4.21 (d, 2H; CH$_2$OCOO), 3.45 (t, 2H; CH$_2$Br), 2.23 (m, 2H; CH$_2$), 1.33 (s, 3H; CH$_3$). $^{13}$C NMR (100 MHz, CDCl$_3$): delta 171.0, 147.3, 72.9, 63.9, 40.2, 31.0, 28.9, 17.3.

Example 42. Preparation of 5-methyl-5-(2-iodoethyl)oxycarboxyl-1,3-dioxan-2-one, (MTCOEtI), MW 314.08

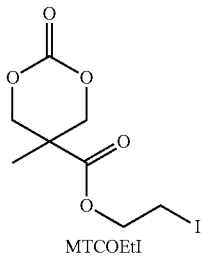

MTCOEtI

MTCOEtI was prepared by the procedure of Example 1 on a 45 mmol scale, using 2-iodoethanol as the alcohol, and was purified by column chromatography and subsequent recrystallization to yield yellowish crystals (7.7 g, 54%). $^1$H NMR (400 MHz, CDCl$_3$): delta 4.73 (d, 2H; CH$_2$OCOO), 4.45 (t, 2H; OCH$_2$), 4.22 (d, 2H; CH$_2$OCOO), 3.34 (t, 2H; CH$_2$I), 1.38 (s, 3H; CH$_3$). $^{13}$C NMR (100 MHz, CDCl$_3$): delta 170.5, 147.3, 72.8, 65.6, 40.3, 17.5, −0.3.

The MIC data for Comparative Examples 37-39 against *E. coli* are summarized in Table 15. Table 15 also includes MIC data against Gram-positive *Bacillus subtilis* (*B. subtilis*) previously reported for Comparative Examples 37-39 (see Table 10, Examples 20, 22, and 24 in published U.S. patent application 2011/0150977 A1 to J. Hedrick, et al.). A lower value indicates greater antimicrobial activity. Comparative Example 40, CL-5, was tested only against *S. aureus* and *B. subtilis*.

TABLE 15

| Ex. | Cationic Polymer | MIC[a] (*B. subtilis*[b]) (mg/L) | MIC[a] (*S. aureus*[b]) (mg/L) | MIC[a] (*E. coli*[c]) (mg/L) |
| --- | --- | --- | --- | --- |
| 37 (comp.) | CL-2 | 62.5[d] | | >500 |
| 38 (comp.) | CL-3 | 31.3[d] | | >500 |
| 39 (comp.) | CL-4 | 62.5[d] | | ~500 |
| 40 (comp.) | CL-5 | 250 | >500 | |

[a]Minimum inhibitory concentration: a concentration, at which the growth of bacteria is completely inhibited.
[b]Gram-positive.
[c]Gram-negative.
[d]From US 2011/0150977 A1.

As seen in Table 15, Comparative Examples 37-40 were active against Gram-positive *B. subtilis*, and only weakly active or not active against Gram-negative *E. coli*. A concentration of about 500 mg/L or more was needed to inhibit growth of *E. coli*.

VI. Hemolytic Activity Assay.

The undesired biological activity of the polymers against mammalian cells was tested using freshly drawn rat red blood cells (rRBCs) obtained from AHU, BRC, Singapore. Thus, rRBCs were subjected to 25× volumetric dilutions in phosphate buffered saline (PBS) to achieve 4% blood content (by volume) as reported previously. Antimicrobial solutions were prepared by dissolving polymers in PBS at concentrations ranging from 0 mg/L to 2000 mg/L. Equal volumes of antimicrobial solutions (100 microliters) were then mixed with the diluted blood suspension (100 microliters). The mixtures were then incubated at 37° C. for 1 hour to allow for the interactions between rRBC and the polymers to take place. Following the incubation, the mixture was subjected to centrifugation (3000 g for 5 minutes), after which, the supernatant (100 mL) was transferred into a 96-well microplate. The hemoglobin release was measured spectrophotometrically by measuring the absorbance of the samples at 576 nm using a microplate reader (TECAN, Switzerland). Two control groups were provided for this assay: untreated rRBC suspension (as negative control), and rRBC suspension treated with 0.1% Triton-X (as positive control). Each assay was performed in 4 replicates and repeated 3 times to ensure reproducibility of the experiments. Percentage of hemolysis was as follows: Hemolysis (%)=[(O.D$_{576nm}$ of the treated sample−O.D$_{576nm}$ of the negative control)/(O.D$_{576nm}$ of positive control−O.D$_{576nm}$ of negative control)]×100%, where O.D$_{576nm}$ means optical density at 576 nm.

FIG. 1 is a graph of the % hemolysis as a function of concentration in ppm of cationic star copolymers CS-3 (Example 24, TMA), CS-6 (Example 31, TMEDA) and CS-7 (Example 32, DMEA), each having a G′″ core and differing only in the amine used for the quaternization. The % hemolysis was about 25% using TMA, about 12% using TMEDA, and less than 1% using DMEA at a concentration of 250 ppm. This indicates that the hydroxyl group present in DMEA significantly reduced hemolysis.

Figure 2:
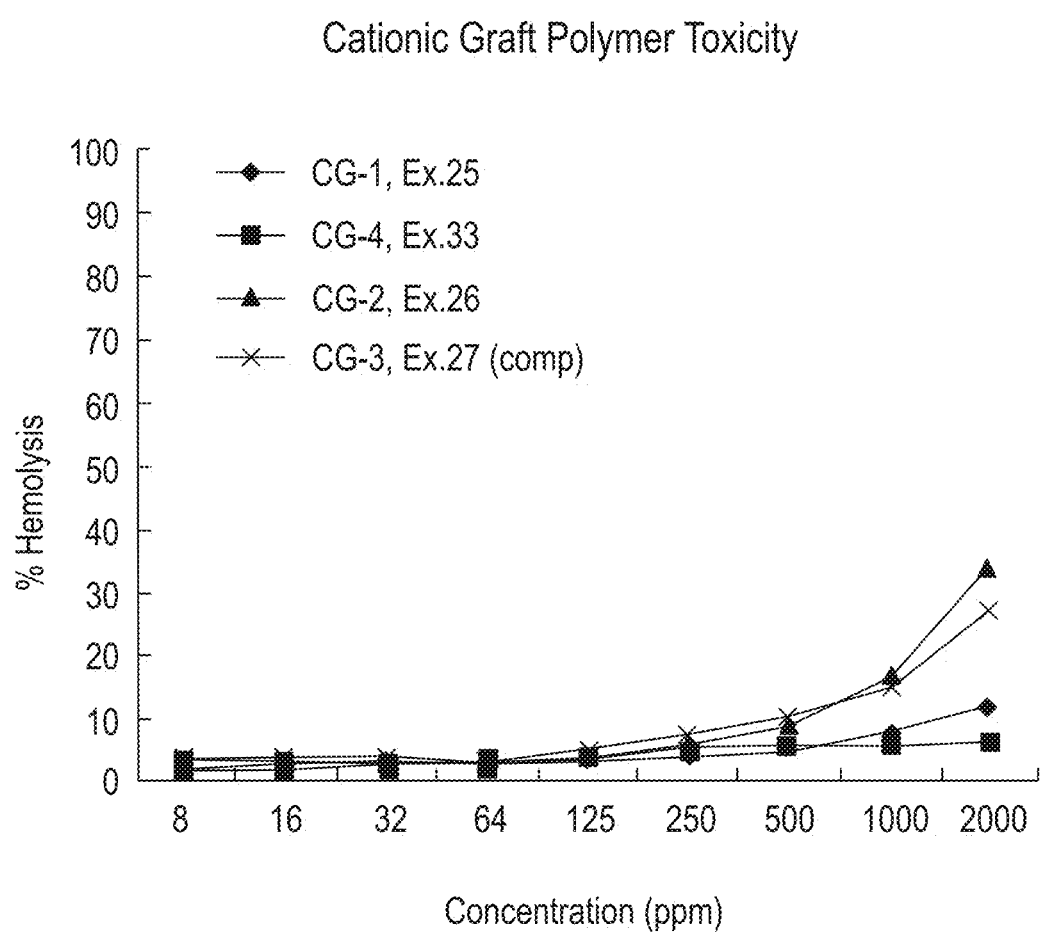
FIG. 2 is a graph of % hemolysis as a function of concentration in ppm of cationic graft copolymers CG-1 (Example 25), CG-2 (Example 26), CG-3 (comparative Example 27), and CG-4 (Examples 33), each quaternized with trimethylamine.

FIG. 2 is a graph of the % hemolysis as a function of concentration in ppm of cationic graft copolymer CG-1 (Example 25), CG-2 (Example 26), CG-3 (comparative Example 27), and CG-4 (Example 33), each quaternized with TMA. In the range of 125 ppm to 250 ppm suitable for antimicrobial use, the % Hemolysis was less than 10% for each cationic polymer. The results demonstrated that the cationic graft polymers had excellent selectivity towards microbes over mammalian cells, and were therefore promising antimicrobials with broad-spectrum activities.

The % hemolysis using cationic linear polymers CL-1 (Example 28) and CL-5 (Example 40) was less than 10% for cationic polymer concentrations in a range of 50 mg/L to 500 mg/L.

VII. Gene Delivery and DNA Expression.

Plasmid DNA encoding the 6.4 kb firefly luciferase gene driven by the cytomegalovirus (CMV) promoter was obtained from Carl Wheeler, Vical (U.S.A.), amplified in *Escherichia coli* DH5a and purified using Endofree Giga plasmid purification kit from Qiagen.

Preparation of DNA complexes with star and graft cationic polycarbonates and control polymer polyethyleneimine (PEI). The polycarbonate polymer or PEI was first dissolved in 10 mM phosphate buffer (pH 6.0) and HPLC grade water. To form the DNA complex, an equivolume solution of DNA was added dropwise to the polycarbonate polymer or PEI solution to achieve the intended N/P ratio (molar ratio of ammonium (N) content in the polymer to phosphorous (P) content in the DNA) under gentle vortexing for approximately 10 seconds. The mixture was equilibrated at room temperature for 30 min to allow for complete electrostatic interaction between the DNA molecule and polymer (PEI, star or graft cationic polycarbonate), before being used for subsequent studies.

Gel retardation assay. Various formulations of polymer/DNA complexes were prepared with various N/P ratios. Post-equilibration, the complexes were electrophoresed on 0.7% agarose gel (stained with 5 microliters of 10 mg/mL ethidium bromide per 50 mL of agarose solution) in 0.5× TBE buffer at 80V for 50 min. The gel was then analyzed under an UV illuminator (Chemi Genius, Evolve, Singapore) to reveal the relative position of the complexed DNA to the naked DNA.

Figure 3:
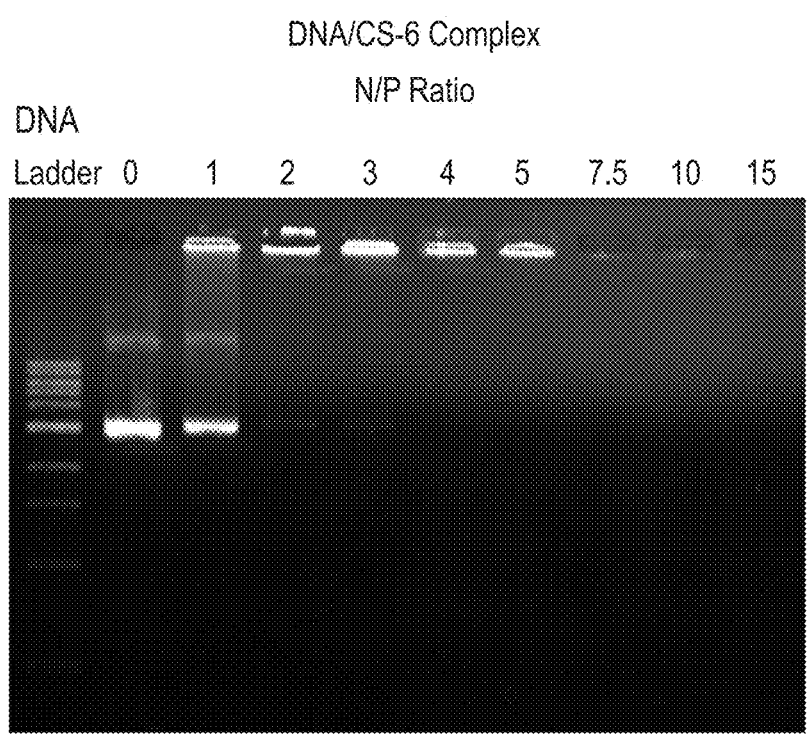
FIG. 3 is a black and white photograph of a DNA mobility test at different N/P ratios for a DNA complex of cationic star polymer CS-6 (Example 31, 32 arms). The photograph shows a UV illuminated agarose gel plate after gel electrophoresis. The complete retardation of DNA mobility in the gel electrophoresis assay was achieved at N/P ratio of 4. N/P ratio is the molar ratio of nitrogen content in the CS-6 polymer to phosphorus in the DNA.

The cationic star polymer CS-6 (Example 31) having 32 arms efficiently condensed DNA (FIG. 3, a black and white photograph of the UV illuminated agarose gel plate after electrophoresis). The complete retardation of DNA mobility in the gel electrophoresis assay was achieved at N/P ratio of 4, where N/P ratio is the molar ratio of nitrogen content in the CS-6 polymer to phosphorus in the DNA.

Figure 4:
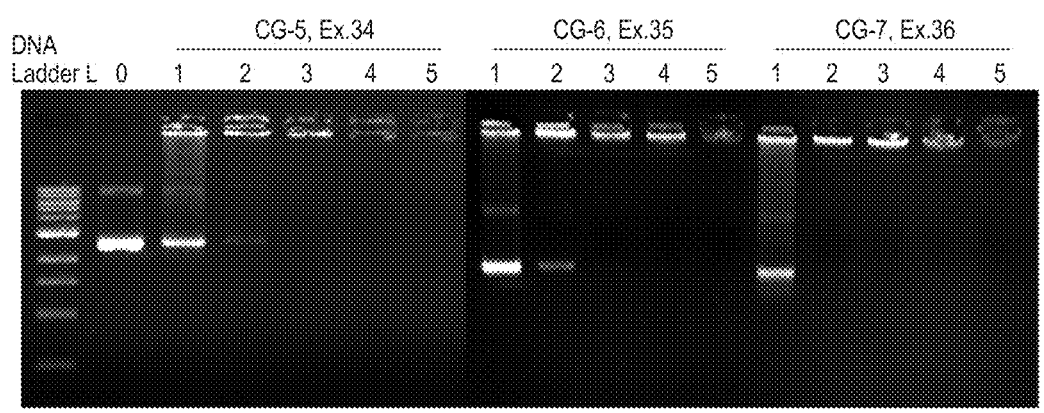
FIG. 4 is a black and white photograph of a DNA mobility test for DNA complexes of cationic graft polymers CG-5 (Example 34), CG-6 (Example 35), and CG-7 (Example 36). The photograph shows UV illuminated agarose gel plates after gel electrophoresis. The complete retardation of DNA mobility in the gel electrophoresis assay was achieved at N/P ratios of 3, 3, and 2, with CG-5, CG-6, and CG-7, respectively.

The cationic graft polymers polyalcohol polymers, CG-5 (Example 34), CG-6 (Example 35), and CG-7 (Example 36) also efficiently condensed DNA (FIG. 4, a black and white photograph of the UV illuminated agarose gel plate after electrophoresis). The complete retardation of DNA mobility in the gel electrophoresis assay was achieved at N/P ratios of 3, 3 and 2, respectively.

In vitro gene expression. HepG2 cells were maintained in MEM growth medium, while 4T1 cells were cultured in RPMI-1640 growth medium. All growth media used were supplemented with 10% FBS, 1 mM sodium pyruvate, 100 U/mL penicillin and 100 mg/mL streptomycin and cultured at 37° C., under an atmosphere of 5% $CO_2$ and 95% humidified air. The reporter gene used was the 6.4 kb firefly luciferase gene driven by the cytomegalovirus (CMV) promoter (Carl Wheeler, Vical, U.S.A.). The in vitro gene transfection efficiency of the cationic polymer or PEI/DNA complexes was investigated using HepG2 and 4T1 cell lines. Cells were seeded onto 24-well plates at a density of $8 \times 10^4$ and $5 \times 10^4$ cells per well respectively. After 24 hours, the plating media was replaced with 0.5 mL of fresh growth media (containing 10% FBS), followed by the addition of 50 microliters of complex solution (containing 2.5 micrograms DNA). Following 4 hours of incubation, free complexes were removed by replacing the media in each well. After a further 68 hours of incubation, the cell culture media in each well was removed and the cells rinsed once with 0.5 mL of PBS before 0.2 mL of reporter lysis buffer (purchased from Promega (U.S.A.)) was added to each well. The cell lysate collected after two cycles of freezing (−80° C., 30 min) and thawing was cleared by centrifugation at 14,000 rpm for 5 min, after which, 20 microliters of supernatant was mixed with 100 microliters of luciferase substrate for the determination of relative light units (RLU) using a luminometer (Lumat LB9507, Berthold, Germany). The RLU readings were normalized against the protein concentration of the supernatant determined using the BCA protein assay to give the overall luciferase expression efficiency. In all in vitro gene expression experiments, naked DNA was used as a negative control and PEI/DNA complexes prepared at the optimal N/P ratio (i.e., 10) were used as the positive control. At N/P=10, PEI induced high gene expression efficiency and provided close to or more than 50% cell viability. Data are expressed as mean standard deviations of four replicates.

Figure 5:
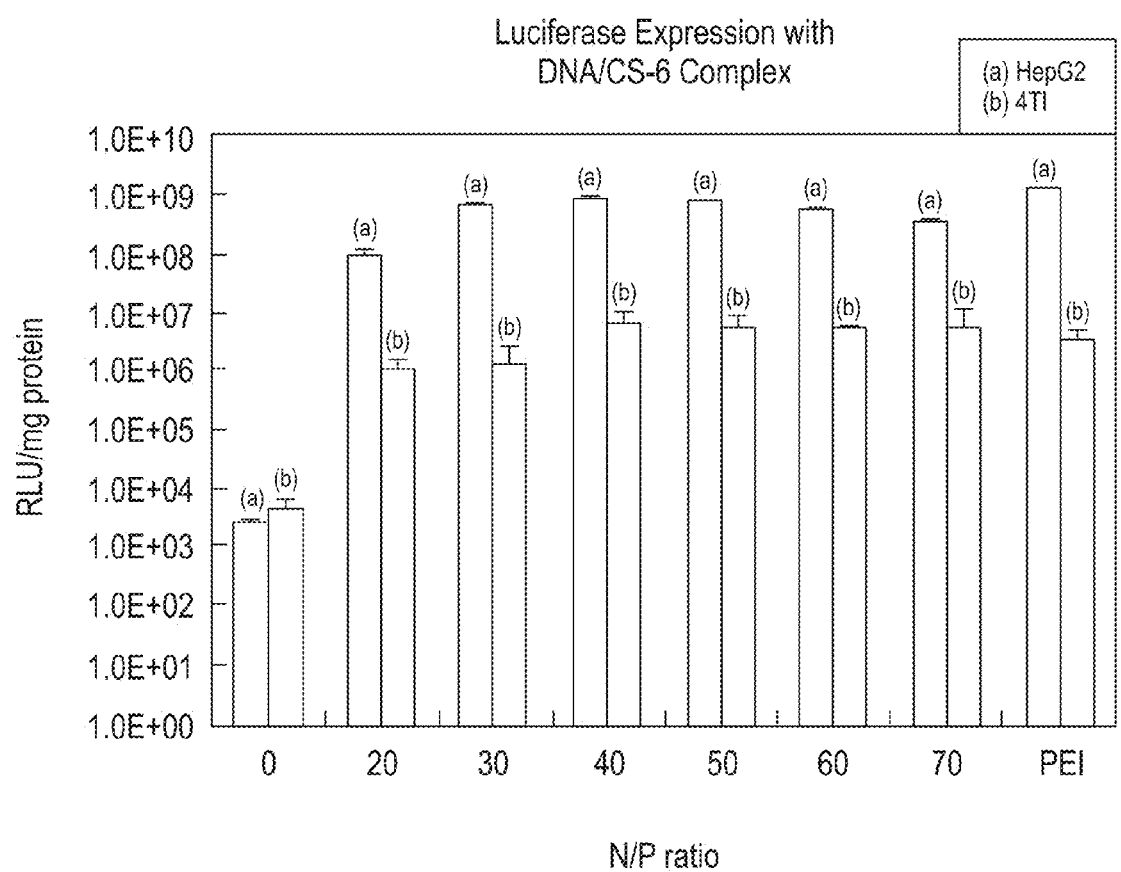
FIG. 5 is bar chart of luciferase expression in relative light units (RLU) as a function of N/P ratio for a DNA complex of cationic star polymer CS-6 (Example 31) in HepG2 and 4T1 cell lines. At N/P 40, the efficiency of luciferase expression with CS-6 was comparable to the efficiency of the control PEI at its optimal N/P ratio of 10, a standard for in vitro gene expression.

High luciferase expression efficiency was achieved with cationic star polymer CS-6 (Example 31) at N/P 40 in HepG2 and 4T1 cell lines (FIG. 5, bar chart). The efficiency of CS-6 was comparable to the efficiency of PEI at its optimal N/P 10, the standard for in vitro gene expression. Cationic star polymer CS-6 was more efficient in gene transfection than previously reported linear polycarbonates (Z. Y. Ong, et al., Journal of Controlled Release, 152 (2011), pg 120-126).

Figure 6:
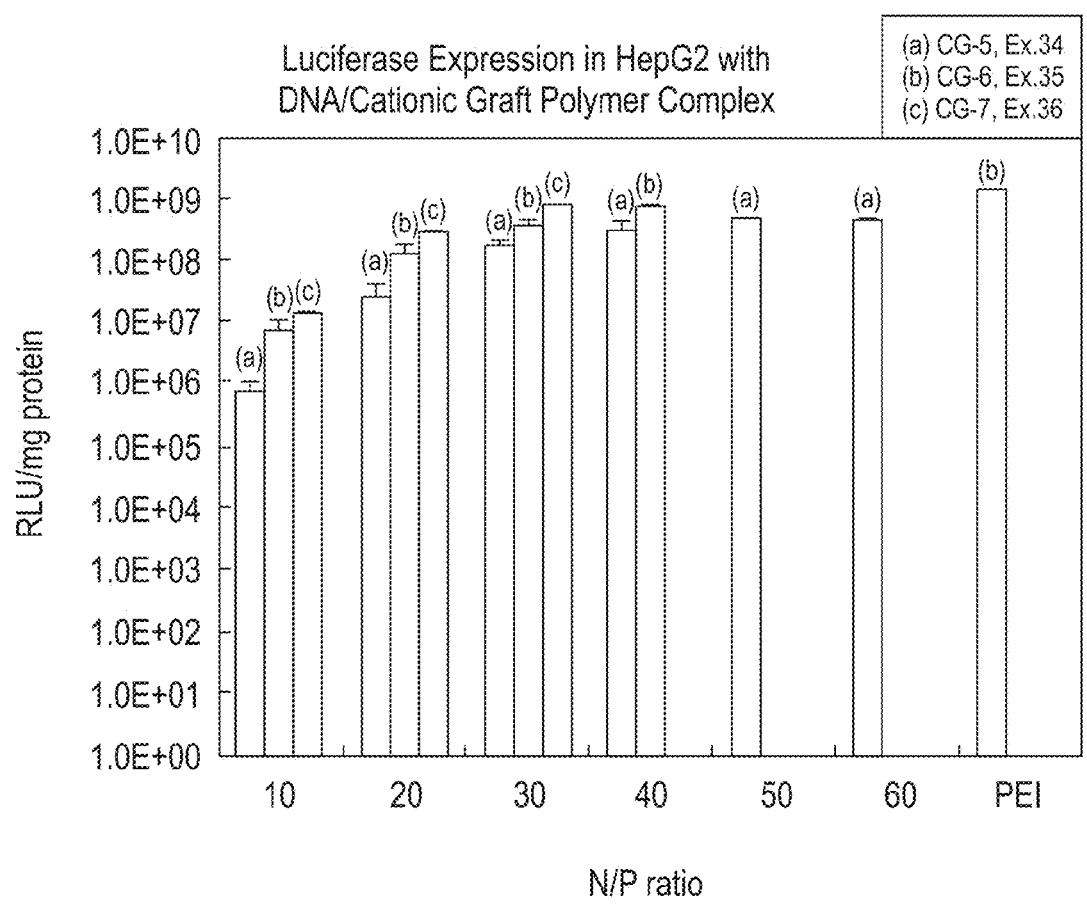
FIG. 6 is bar chart of luciferase expression in relative light units (RLU) versus N/P ratio for DNA complexes of cationic graft polymers CG-5 (Example 34), CG-6 (Example 35), and CG-7 (Example 36) in HepG2 cell line. Optimal N/P ratios for CG-5, CG-6 and CG-7 were 50, 20 and 20 respectively. These cationic graft polymers mediated lower gene expression efficiency as compared to the cationic star polymer CS-6 (Example 31).

Cationic graft polymers CG-5 (Example 34), CG-6 (Example 35) and CG-7 (Example 36) also induced high luciferase expression at N/P ratios that gave rise to more than 80-90% cell viability (i.e., N/P 50, 20 and 20 for CG-5, CG-6 and CG-7, respectively) (FIG. 6, bar chart). However, the luciferase expression levels yielded by DNA complexes with CG-5, CG-6 and CG-7 at the optimal N/P ratios 50, 20 and 20, respectively) was still 5 times lower than that mediated by PEI/DNA complexes. The cationic graft polymers also mediated lower gene expression efficiency compared to the cationic star polymer CS-6 (Example 31).

VIII. Cytotoxicity of Cationic Polymers Formed with TMEDA.

The cytotoxicity of the cationic polymer/DNA complexes was studied using the standard MTT assay protocol. HepG2 and 4T1 cells were seeded onto 96-well plates at densities of 10000 and 6000 cells per well respectively and allowed to grow to 60-70% confluency before treatment. Cationic polymer/DNA complexes at various N/P ratios were prepared in 10 mM phosphate buffer (pH 6.0) as described above. The cells in each well were then incubated with sample-containing growth media comprising of 10 microliters of polymer/DNA complexes and 100 microliters fresh media for 4 hours at 37° C. Following incubation, the wells were replaced with fresh growth media and incubated further for 68 hours. Subsequently, 100 microliters of growth media and 10 microliters of MTT solution (5 mg/mL in PBS) were then added to each well and the cells were incubated for 4 hours at 37° C. according to the manufacturer's directions. Resultant formazan crystals formed in each well were solubilized using 150 microliters of DMSO upon removal of growth media. A 100 microliter aliquot from each well was then transferred to a new 96-well plate for determination of absorbance using a microplate spectrophotometer at wavelengths of 550 nm and 690 nm. Relative cell viability was expressed as $[(A_{550nm}-A_{690nm})Sample/((A_{550nm}-A_{690nm})Control] \times 100\%$, where $(A_{550nm}-A_{690nm})$Sample is the Sample absorbance at 550 nm minus the Sample absorbance at 690 nm, and $(A_{550nm}-A_{690nm})$Control is the Control absorbance at 550 nm minus the Control absorbance at 690 nm. Data are expressed as mean±standard deviations of at least eight replicates per N/P ratio.

Figure 7:
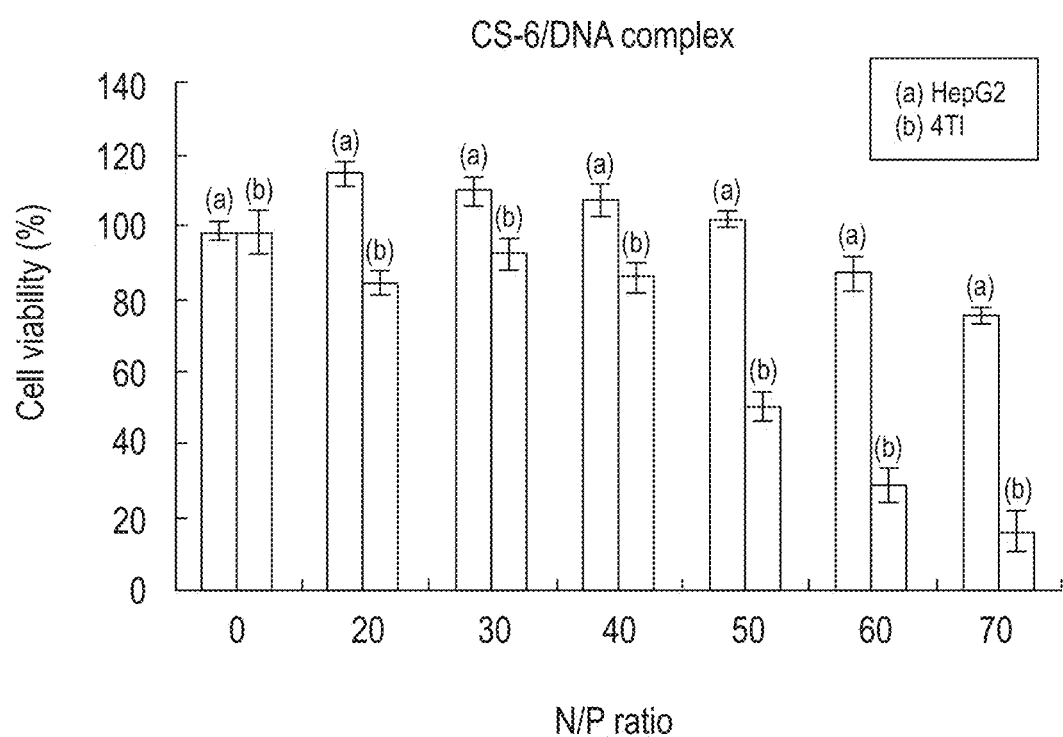
FIG. 7 is bar chart of cell viability in percent of HepG2 and 4T1 cells as a function of N/P ratio of a DNA complex with cationic star polymer CS-6 (Example 31). At the optimal N/P ratio (i.e., N/P=40) for gene expression, CS-6 (Example 31) was not significantly toxic.

At the optimal N/P ratio (i.e., N/P=40), the DNA complex of cationic star polymer CS-6 (Example 31) was not significantly toxic to HepG2 and 4T1 cells (FIG. 7, bar chart). The viability of HepG2 and 4T1 cells was more than 85% after incubation with CS-6/DNA complex.

Figure 8:
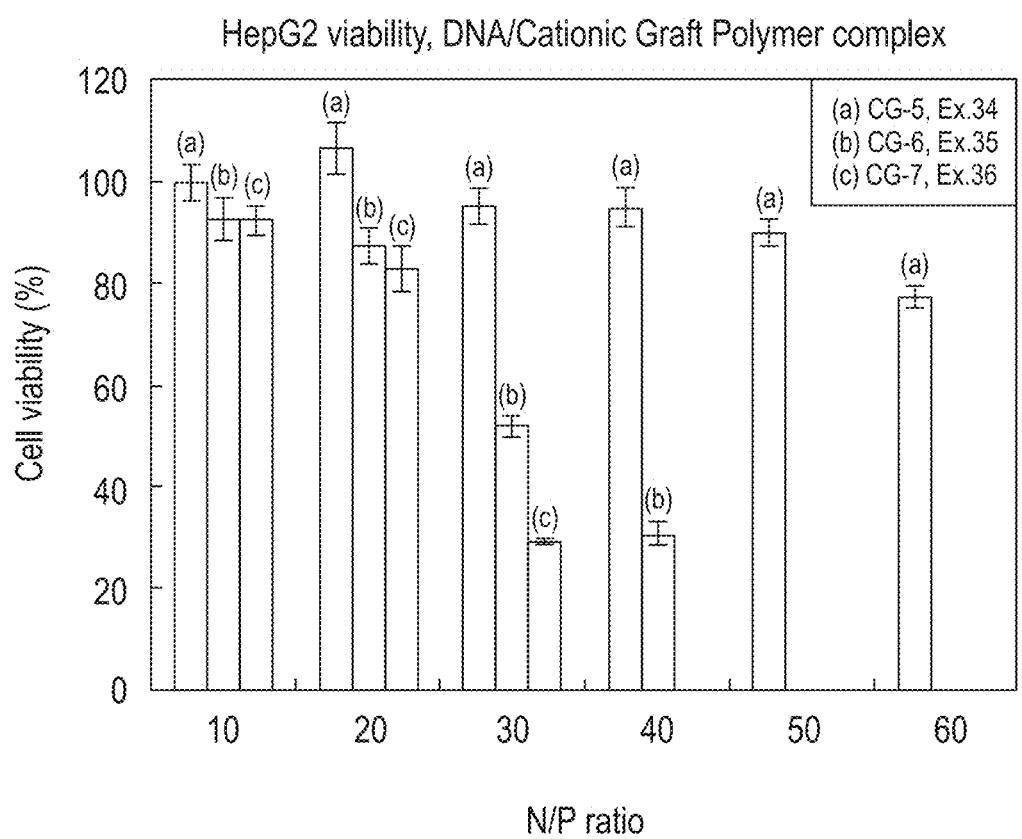
FIG. 8 is bar chart of cell viability in percent of HepG2 cells as a function of N/P ratio of a DNA complexes made with cationic graft polymers CG-5 (Example 34), CG-6 (Example 35) and CG-7 (Example 36). More than 80-90% cell viability was achieved with CG-5, CG-6 and CG-7 at N/P=50, 20 and 20, respectively.

More than 80-90% cell viability was achieved after incubating HepG2 cells with the DNA complexes of cationic graft polymers CG-5 (Example 34), CG-6 (Example 35) and CG-7 (Example 36) at N/P=50, 20 and 20, respectively (FIG. 8, bar chart).

IX. Degradability of Dendritic Phenolic Esters.

U.S. patent application Ser. No. 13/077,005 discloses G-2(OH)$_{12}$, shown below, which has 12 nucleophilic hydroxy groups capable of initiating ring opening polymerization of one or more cyclic carbonyl monomers (e.g., L-lactide, D-lactide, cyclic carbonates, lactones, and the like) to form a ROP star polymer comprising 12 polymer arms, such as SP12 (Scheme A).

Scheme A.

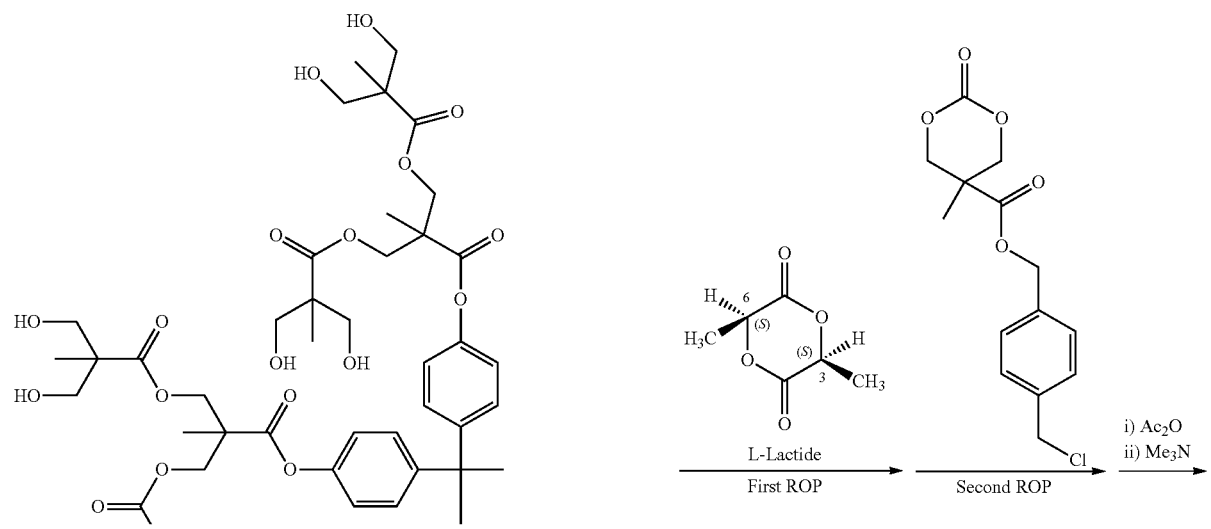

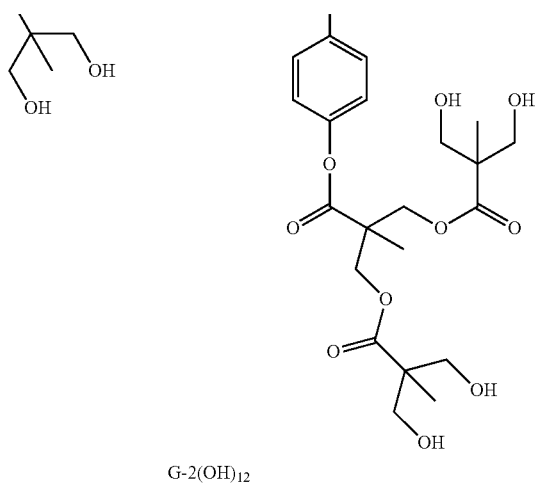

G-2(OH)$_{12}$

SP12

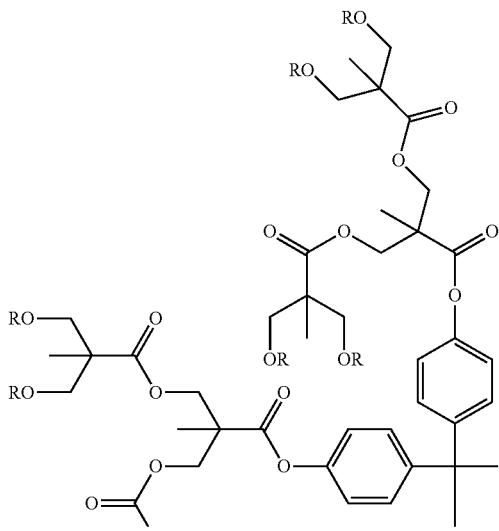

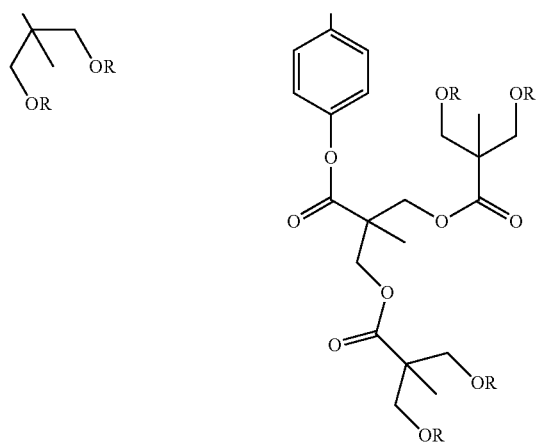

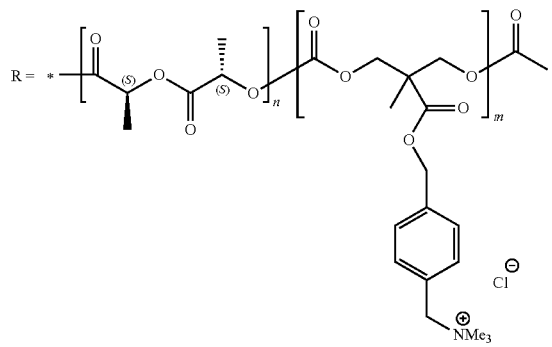

The starred bond represents the point of attachment of each R group (a polymer arm) to an oxygen in the SP12 structure. Thus, SP12 has 12 polymer arms, each polymer arm independently comprising an inner hydrophobic poly(L-lactide) block attached to a core structure derived from G-2(OH)$_{12}$, and a peripheral cationic polycarbonate block attached to the poly(L-lactide) block. The order of the foregoing ring opening polymerizations can be reversed, resulting in a star polymer having a peripheral hydrophobic block, as shown in SP13 below.

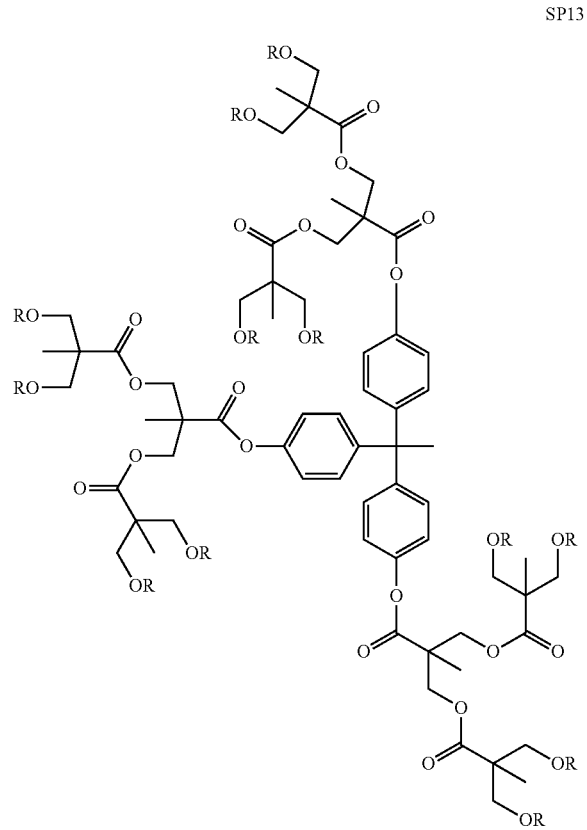

The L-lactide can be substituted with D-lactide in the ring opening polymerization to form a star polymer having opposite stereospecificity if desired.

In the above structures of SP12 and SP13, n=10 and m=15.

The following example demonstrates the instability of the phenolic ester in D-1.

A vial was charged with D-1 (0.1 g, 0.153 mmol), DBU (0.0186 g, 0.122 mmol), MeOH-$d_4$ (2 mL) and a stir bar. The reaction mixture was stirred at ambient temperature and observed every hour for degradation. After 1 hour, significant loss of the phenolic ester group was observed.

The following example demonstrates the stability of the aliphatic ester in G-1(OH)$_8$ (Example 14 further above). A vial was charged with G-1(OH)$_8$, DBU (0.0186 g, 0.122 mmol), MeOH-$d_4$ (2.66 mL) and stir bar. The reaction mixture was stirred at ambient temp and observed every hour for degradation. No change in the structure of G1-(OH)$_8$ was detected after 6 hours using NMR.

The MIC of SP12 was not determined because the phenolic ester groups hydrolyzed too easily. Instead, a linear ROP block copolymer was prepared having the same polymer chain block structure as the R chain of SP12. This linear block copolymer was tested for antimicrobial activity using the same protocol as described above for unimolecular cationic star polymers having a G', G", or G'" core structure. The MIC against *S. aureus* was >500 mg/L for the linear block copolymer. This demonstrates that core I' groups containing repeat units that include carboxylic esters of phenolic alcohols are less preferred for I' due to their hydrolytic instability. This also demonstrates the inferior antimicrobial properties of a linear ROP copolymer having a similar cationic arm structure as star polymers CS-1, CS-2, CS-3. That is, the quaternary amine group comprising a benzyl moiety was not sufficient alone to achieve enhanced antimicrobial properties. The greatest antimicrobial activity was observed with the cationic polymers having a hydrophobic branched core group and a quaternary amine group comprising a benzyl moiety.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A cationic star polymer of formula (1):

$$I'-[P']_{w'}, \quad (1)$$

wherein w' is a positive number greater than or equal to 3,

I' is a dendritic polyester core comprising carboxylic ester repeat units of aliphatic alcohols, wherein I' is free of carboxylic esters of phenolic alcohols, and I' comprises 3 or more peripheral ester repeat units, the cationic star polymer comprises w' independent peripheral cationic polymer chains P', wherein each of the chains P' is covalently linked to a respective one of the peripheral ester repeat units, each of the chains P' independently comprises a cationic repeat unit comprising i) an aliphatic carbonate backbone functional group and ii) a side chain comprising a quaternary amine group, and the quaternary amine group comprises a divalent methylene group directly covalently linked to i) a positive charged nitrogen and ii) an aromatic ring.

2. The cationic star polymer of claim 1, wherein I' is G':

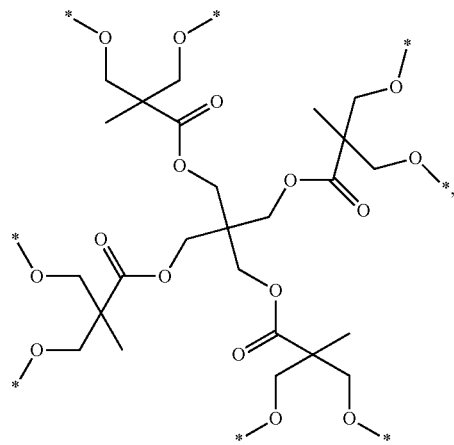

wherein the oxygens having starred bonds of G' are linked to respective P' groups or hydrogens.

3. The cationic star polymer of claim 1, wherein I' is G":

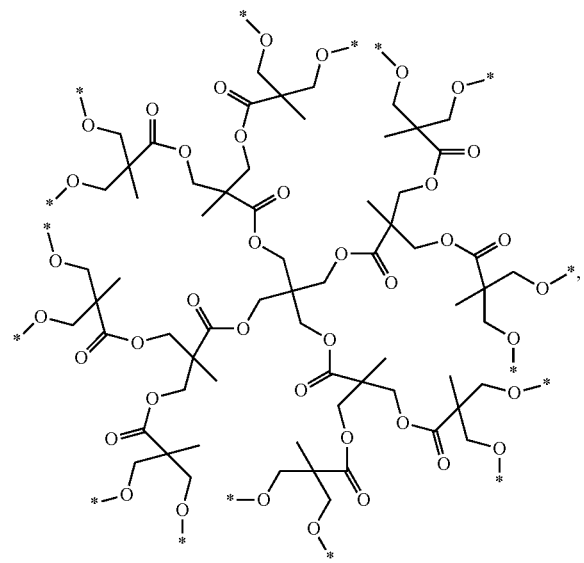

wherein the oxygens having starred bonds of G" are linked to respective P' groups or hydrogens.

4. The cationic star polymer of claim 1, wherein I' is G''':

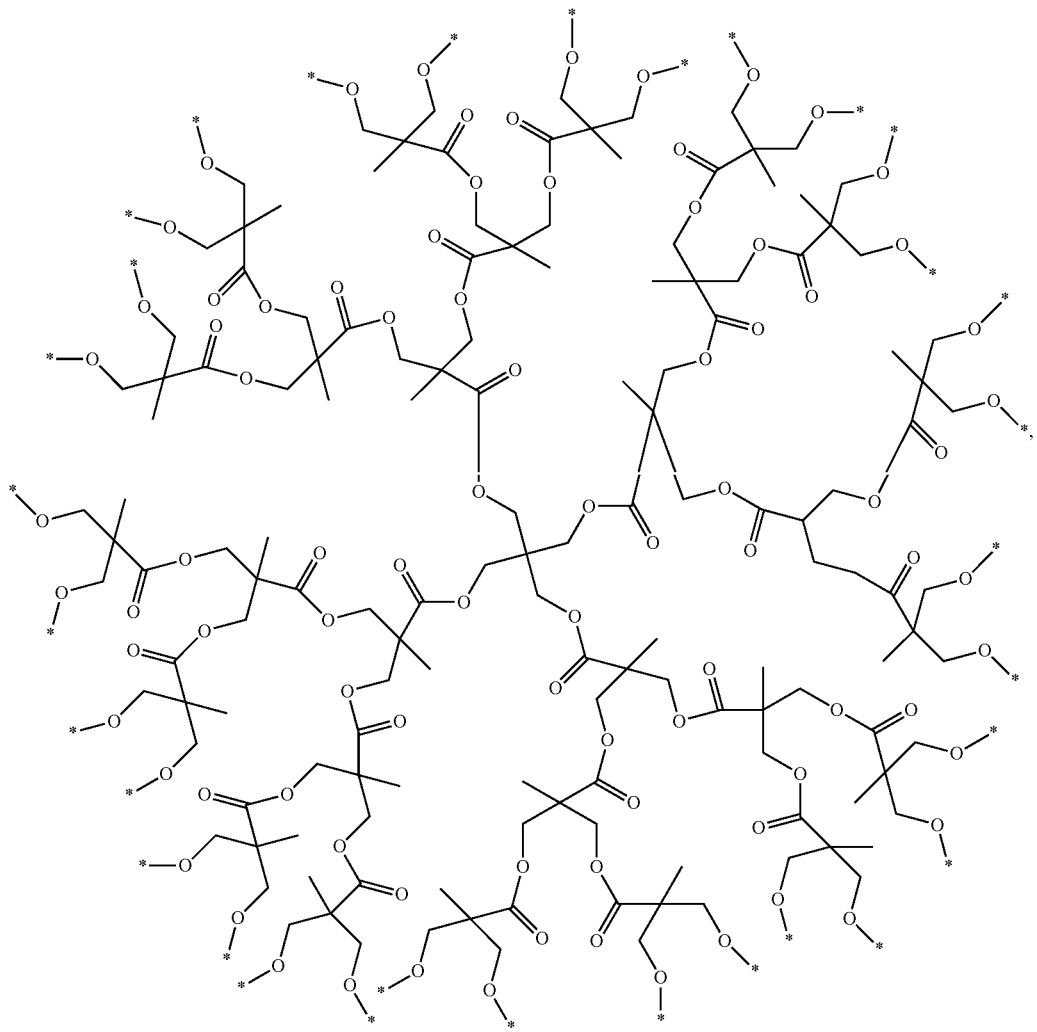

wherein the oxygens having starred bonds of G''' are linked to respective P' groups or hydrogens.

5. The cationic star polymer of claim 1, wherein each P' is a diblock copolymer chain comprising a polyester block and a polycarbonate block, wherein the polyester block comprises i) a first end group linked to an end group of the polycarbonate block and ii) a second end group linked to I'.

6. The cationic star polymer of claim 1, wherein the cationic star polymer is biocompatible and/or enzymatically biodegradable.

7. A method of forming the cationic star polymer of claim 1, comprising:
   forming a mixture containing i) an organocatalyst, ii) an optional accelerator, iii) a solvent, iv) a dendritic polyester initiator comprising 3 or more peripheral nucleophilic initiator groups for ring opening polymerization (ROP), wherein the ester repeat units of the initiator are carboxylic ester repeat units of aliphatic alcohols, and the initiator is free of carboxylic esters of phenolic alcohols, and v) a cyclic carbonate monomer comprising a pendant electrophilic group capable of reacting with a tertiary amine to form a quaternary amine;
   agitating the mixture, thereby forming an electrophilic polymer by ROP;
   optionally endcapping the electrophilic polymer, thereby forming an endcapped electrophilic polymer; and
   treating the electrophilic polymer and/or the endcapped electrophilic polymer with the tertiary amine, thereby forming the cationic star polymer.

8. The method of claim 7, wherein each P' is a diblock copolymer chain.

9. The method of claim 7, wherein the initiator is selected from the group consisting of $G\text{-}1(OH)_8$, $G\text{-}2(OH)_{16}$, and $G\text{-}3(OH)_{32}$.

10. The method of claim 7, wherein the tertiary amine is selected from the group consisting of trimethylamine (TMA), TMEDA, and combinations thereof.

11. The method of claim 7, wherein the initiator is $G\text{-}3(OH)_{32}$ and the tertiary amine is trimethylamine (TMA).

12. The method of claim 7, wherein the initiator is $G\text{-}1(OH)_8$ and the tertiary amine is TMEDA.

13. The method of claim 7, wherein each P' is a diblock copolymer chain comprising a polyester block and a polycarbonate block, wherein the polycarbonate block consists essentially of a homopolymer of cationic repeat unit selected from the group consisting of

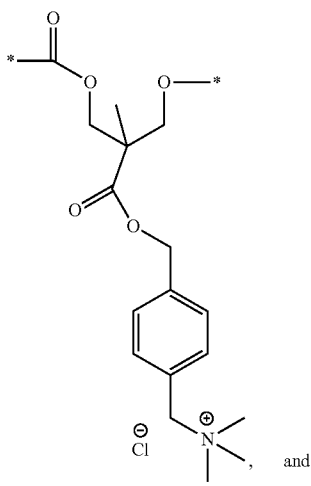, and

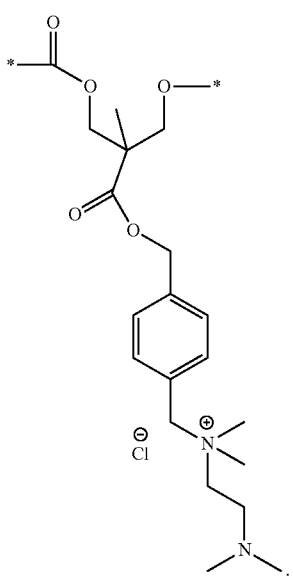

14. A cationic star polymer comprising: 3 or more independent peripheral monovalent linear cationic polymer chains P', wherein each of the chains P' is covalently linked to a respective one of the ester repeat units of a dendritic polyester core I', and wherein each of the chains P' independently comprises a cationic repeat unit of the general formula (11):

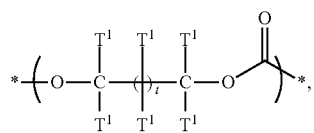

wherein I) t is an integer from 0 to 6, II) each $T^1$ is a monovalent radical independently selected from the group consisting of hydrogen, and functional groups comprising 1 to 30 carbons, and III) at least one $T^1$ group comprises a quaternary amine group, the quaternary amine group comprising a divalent methylene group that is directly covalently linked to i) a positive charged nitrogen and ii) an aromatic ring, and wherein the ester repeat units of I' are carboxylic ester repeat units of aliphatic alcohols, wherein I' is free of carboxylic esters of phenolic alcohols.

15. A method of killing a microbe comprising contacting the microbe with the cationic star polymer of claim 1.

16. An injectable composition comprising an aqueous mixture of the cationic star polymer of claim 1.

17. A method of treating a cell comprising contacting the cell with a composition comprising i) the cationic star polymer of claim 1 and ii) a gene and/or a drug.

18. An article, comprising the cationic star polymer of claim 1 disposed on a surface of a medical device.

19. The article of claim 18, wherein the medical device is selected from the group consisting of swabs, catheters, sutures, stents, bedpans, gloves, facial masks, absorbent pads, absorbent garments, internal absorbent devices, insertable mechanical devices, wound dressings, and surgical instruments.

20. A cationic star polymer comprising i) a dendritic polyester core I' comprising carboxylic ester repeat units of aliphatic alcohols, wherein I' is free of carboxylic esters of phenolic alcohols, and I' comprises three or more peripheral ester repeat units and ii) 3 or more independent monovalent cationic polymer chains P', wherein each of the peripheral ester repeat units is linked to a respective end unit of one of the polymer chains P', each of the polymer chains P' independently comprises a homopolymer of a cationic repeat unit selected from the group consisting of

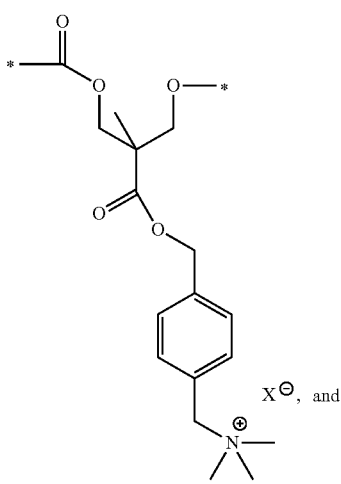

-continued

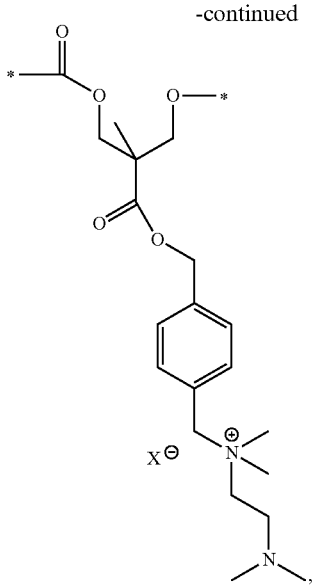

wherein $X^{\ominus}$ is a negative charged counterion, and the cationic star polymer is an effective antimicrobial agent against a Gram-positive microbe and/or a Gram-negative microbe.

21. A cationic star polymer, comprising:

a multivalent hydrophobic dendritic polyester core I' comprising carboxylic ester repeat units of aliphatic alcohols, wherein I' is free of carboxylic esters of phenolic alcohols, and I' comprises 3 or more peripheral ester repeat units covalently linked to respective independent peripheral monovalent cationic polymer chains P', each of the polymer chains P' independently comprises a cationic repeat unit comprising i) an aliphatic carbonate backbone functional group and ii) a side chain comprising a quaternary amine group, and the quaternary amine group comprises a divalent methylene group directly covalently linked to i) a positive charged nitrogen and ii) an aromatic ring.

* * * * *